(12) United States Patent
Altmann et al.

(10) Patent No.: US 6,387,927 B1
(45) Date of Patent: May 14, 2002

(54) EPOTHILONE DERIVATIVES AND THEIR USE AS ANTITUMOR AGENTS

(75) Inventors: Karl-Heinz Altmann, Reinach; Guido Bold, Gipf-Oerfrick; Giorgio Caravatti, Bottmingen; Andreas Flörsheimer, Möhlin, all of (CH)

(73) Assignee: Novatis AG, Basel (CH)

( * ) Notice: Subject to any disclaimer, the term of this patent is extended or adjusted under 35 U.S.C. 154(b) by 0 days.

(21) Appl. No.: 09/871,860

(22) Filed: Jun. 1, 2001

Related U.S. Application Data

(63) Continuation of application No. PCT/EP99/10129, filed on Dec. 20, 1999.

(30) Foreign Application Priority Data

Dec. 22, 1998 (CH) .............................................. 2530/98

(51) Int. Cl.⁷ .................... A61K 31/428; C07D 235/08; A61P 43/00
(52) U.S. Cl. .................. 514/311; 514/314; 514/367; 514/374; 514/375; 514/395; 548/305.1; 548/310.1; 548/180; 548/159; 548/217; 546/174
(58) Field of Search ............................. 548/305.1, 159, 548/217; 546/174; 514/311, 314, 367, 374

(56) References Cited

FOREIGN PATENT DOCUMENTS

WO    WO 99/01124    1/1999
WO    WO 99/02514    1/1999

OTHER PUBLICATIONS

End, et al, 1999, Proc. ECSOC–3, Proc. ECSOC–4, 1431–1442.*

Altmann, et al, 2000, Bioorg. Med. Chem. Lett., 10(24), 2765–2768.*

Dai–Shi Su et al., Angewandte Chemie International Edition vol. 36, No. 19, Oct. 17, 1997.

* cited by examiner

*Primary Examiner*—Floyd D. Higel
*Assistant Examiner*—Andrew D'Souza
(74) *Attorney, Agent, or Firm*—George R. Dohmann

(57) ABSTRACT

The invention relates to anti-tumour-effective compounds of formula (I), wherein the radicals have the meanings given in the description.

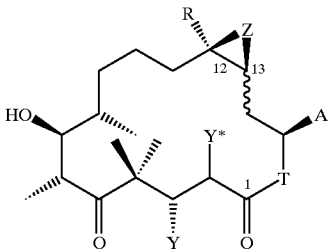

(I)

16 Claims, No Drawings

EPOTHILONE DERIVATIVES AND THEIR USE AS ANTITUMOR AGENTS

This is a continuation of International Application No. PCT/EP99/10129, filed Dec. 20, 1999, the contents of which are incorporated herein by reference.

SUMMARY OF THE INVENTION

The invention relates to a new class of epothilone derivatives, the production of these compounds and new intermediates, pharmaceutical preparations containing these compounds, and the use of these compounds in the treatment of warm-blooded animals, such as humans, or their use in the production of pharmaceutical preparations for the treatment of warm-blooded animals, such as humans.

BACKGROUND TO THE INVENTION

Epothilones A and B represent a new class of microtubule-stabilising cytotoxic agents (see Gerth, K. et al., J. Antibiot. 49, 560–3 (1966)) of the formulae:

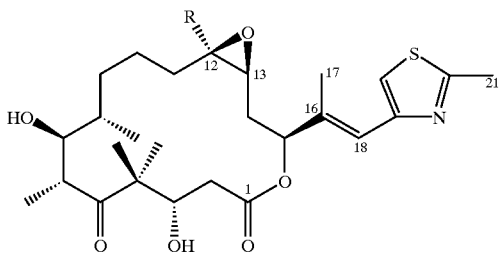

wherein R means hydrogen (epothilone A) or methyl (epothilone B).

These compounds have advantages over Taxol®, a branded product already introduced for the treatment of tumours, that has the same mechanism of action but has however a series of disadvantages, such as very poor water solubility, making the preparation of pharmaceutical formulations very difficult (at present, such formulations are normally characterised by the toxic side effects of the carrier materials), and inefficacy on a series of tumours. The advantages are as follows:

a) They have better water-solubility and are thus more readily accessible for formulations.

b) It has been reported that, in cell culture experiments, they are also active against the proliferation of cells, which, owing to the activity of the P-glycoprotein efflux pump making them "multidrug resistant", show resistance to treatment with other chemotherapy agents including Taxol® (see Bolag, D. M., et al., "Epothilones, a new class of microtubule-stabilizing agents with a Taxol-like mechanism of action", Cancer Research 55, 2325–33 (1995)). And c) it could be shown that they are still very effective in vitro against a Taxol®-resistant ovarian carcinoma cell line with modified β-tubulin (see siehe Kowalski, R. J., et al., J. Biol. Chem. 272(4), 2534–2541 (1997)).

Pharmaceutical application of the epothilones, for example for tumour treatment, is possible in an analogous manner to that described for Taxol, see for example U.S. Pat. No. 5.641.803; U.S. Pat. No. 5.496.804; U.S. Pat. No. 5.565.478). One disadvantage of the epothilones is the relatively low therapeutic index, i.e. the dosage range between the necessary dose and the maximum tolerable dose is very small.

In the meantime, a series of epothilone derivatives have been published in the search for new, more effective and more versatile products.

Up until now, all epothilones described in the literature contain a methyl group shown in the above formula at C-16. This methyl group (C-17) was hypothesized to be necessary in order Ws to force the heterocycle (in the case of epothilones A and B a methylthiazolyl ring) out of the plane of the conjugated double bond between C-16 and C-18, and this was postulated to be necessary for efficacy.

It is an objective of the invention to provide a new class of epothilone derivatives, which have a new type of structure and which, through their advantageous biological and pharmacological properties, enable the armamentarium for the control of, in particular, proliferative diseases such as tumours to be expanded. Also, compounds must be found which have an improved therapeutic index compared with epothilones A and B.

DETAILED DESCRIPTION OF THE INVENTION

Surprisingly, a new class of epothilone derivatives has been found, which are pharmacologically highly effective, despite the absence of the methyl group on C-16 of the epothilones and even though the resulting heterocyclic ring lies on the plane of the C-16/C-18 double bond.

The invention relates to this new class of epothilone derivatives. The compounds in question are compounds of formula I,

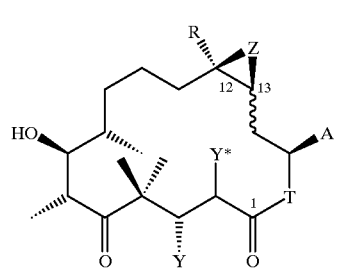

(I)

wherein

T is O, NH or N(alkyl), wherein alkyl is alkyl, especially lower alkyl;

as A is a radical of formula Ia

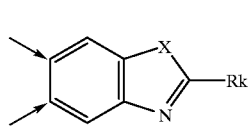

(Ia)

which is bonded to the radical of the molecule according to formula I by one of the two carbon atoms marked with an arrow, especially by the lower carbon atom (the one nearer to the nitrogen in the fused heterocyclic ring or para to the atom X), and wherein X is S; O; NH; N(alk); wherein alk is alkyl, hydroxy-lower alkyl, unsubstituted or substituted amino-lower alkyl or carbamoyl-lower alkyl; N(ar), wherein ar is aryl; C(Rk*)=N, N=C(Rk*) or C(Rk*)=C(Rk**), wherein Rk* and Rk**, independently of one another, are H, alkyl (especially lower alkyl), unsubstituted or substituted amino-lower alkyl, carbamoyl-lower alkyl, or in particular halogen-lower alkyl or hydroxy-lower alkyl, or further aminolower alkyl; and Rk is H, alkyl (especially lower alkyl), unsubstituted or substituted amino-lower alkyl, carbamoyl-lower alkyl, or in particular halogen-lower alkyl or hydroxy-lower alkyl;

either Y is OH and Y* is hydrogen, or —Y and —Y* together form a bond (so that together with the adjoining bond connecting the two —Y and —Y* bearing carbon atoms they form a double bond);

R is hydrogen, lower alkyl or halogen-lower alkyl;

and Z is O, or —Z— is a bond between the two binding carbon atoms;

or salts thereof.

These compounds have advantageous pharmaceutical properties. For example, they are active against multidrug-resistant cell lines and tumours and/or they have an improved therapeutic index over natural epothilones.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either unbranched or branched with single or multiple branching.

Where the plural form is used for compounds, salts, and the like, this is taken to mean also a single compound, salt, or the like ("a" as an indefinite article or as a numeral meaning "one").

Asymmetric carbon atoms that are optionally present in the substituents may exist in the (R), (S) or (R,S) configuration, preferably in the (R) or (S) configuration. Substituents on a double bond or on a ring, for example on the carbon atoms to which Z in formula I is bonded, may be present in cis- (=Z-) or trans- (=E-) form. The present compounds may thus exist as mixtures of isomers or as pure isomers, preferably as pure diastereoisomers.

T is either O, NH or N(alkyl), especially either O or NH, preferably O.

The radical A is bonded to the radical of the molecule of formula I by one of the two carbon atoms marked by an arrow in formula Ia. Bonding is preferably effected via the carbon atom of the benzene ring portion of A which is in para position to X.

Alkyl is preferably an alkyl radical with 1 to 10 carbon atoms, preferably lower alkyl, especially methyl.

Lower alkyl is unbranched or has mono- or multiple-branching and is in particular methyl or ethyl.

Aryl is preferably an aromatic radical with 6 to 14 carbon atoms, especially phenyl, naphthyl, fluorenyl or phenanthrenyl, whereby the said radical is unsubstituted or is substituted by one or more substituents, preferably up to three, primarily one or two substituents, especially those selected from amino; lower alkanoylamino, especially acetylamino; halogen, especially fluorine, chlorine or bromine; lower alkyl, especially methyl or also ethyl or propyl; halogen-lower alkyl, especially trifluoromethyl; hydroxy; lower alkoxy, especially methoxy or also ethoxy; phenyl-lower alkoxy, especially benzyloxy; nitro, cyano, $C_8$–$C_{12}$-alkoxy, especially n-decyloxy, carbamoyl, lower alkyl-carbamoyl, such as N-methyl- or N-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halogen-lower alkyl-mercapto, such as trifluoromethylmercapto, hydroxy-lower alkyl, such as hydroxymethyl or 1-hydroxymethyl, lower alkanesulphonyl, such as methanesulphonyl, halogen-lower alkane-sulphonyl, such as trifluoromethanesulphonyl, phenylsulphonyl, dihydroxybora (-B(OH)$_2$), 2-methyl-pyrimidin-4-yl, oxazol-5-yl, 2-methyl-1,3-dioxolan-2-yl, 1H-pyrazol-3-yl, 1-methyl-pyrazol-3-yl; and lower alkylenedioxy which is bonded to two adjacent carbon atoms, such as methylenedioxy.

Halogen is especially fluorine, chlorine, bromine, or iodine, in particular fluorine or chlorine.

Halogen lower alkyl is methyl or ethyl that is substituted in particular by halogen, such as fluorine or chlorine, especially fluoromethyl or also chloromethyl.

Hydroxy lower alkyl is in particular lower alkyl that is terminally substituted by hydroxy, preferably hydroxymethyl or hydroxyethyl, especially 2-hydroxyethyl.

Unsubstituted or substituted amino lower alkyl is in particular lower alkyl that is terminally substituted by amino or substituted amino, whereby preferably one or two lower alkyl radicals are present as amino substituents; aminomethyl, 2-aminoethyl, N-methylamino-methyl, 2-(N-methylamino)ethyl, N,N-dimethylaminomethyl or 2-(N,N-dimethylamino)ethyl are preferred.

Carbamoyl lower alkyl is in particular lower alkyl that is terminally substituted by —C(O)NH$_2$, preferably carbamoylmethyl or 2-carbamoylethyl.

Where these radicals are present, one of radicals Rk, Rk* and Rk** is preferably hydrogen and the others are also each hydrogen, or preferably one is lower alkyl, such as methyl, halogen-lower alkyl, such as methyl fluoride, or hydroxy-lower alkyl, such as hydroxymethyl or -ethyl, and the other is hydrogen, or one is unsubstituted or substituted amino lower alkyl, especially aminoethyl, 2-aminoethyl, N-methylaminomethyl, 2-(N-methylamino)ethyl, N,N-dimethylaminomethyl or 2-(N,N-dimethylamino)ethyl, and the other is hydrogen, —Y and —Y* either form a bond, so that a double bond exists together with the bond linking the Y and Y* bearing carbon atoms; or preferably Y is hydroxy and Y* is hydrogen.

Where present, one of radicals Rk, Rk* and Rk** is preferably methyl or hydroxymethyl, and the other(s) is or are hydrogen, or one of radicals Rk, Rk* and Rk** is 2-hydroxyethyl, aminomethyl, 2-aminoethyl, N,N-dimethylaminomethyl or carbamoylmethyl, and the other(s) is or are hydrogen.

If Rk* and Rk** are not present, Rk is preferably hydrogen, methyl or hydroxymethyl, or ethyl.

R is preferably hydrogen, methyl or fluoromethyl, also ethyl.

Z is either O, whereupon an oxirane is formed with the binding carbon atoms, or —Z— is a bond, so that a double bond is produced together with the already existing bond between the two carbon atoms to which Z is bonded.

The wavy line of the bond to the Z-bearing carbon atom is to indicate that the compound of formula I, in respect of the epoxide ring or the double bond formed by Z and the two adjacent carbon atoms, may be present in the Z- (=cis-)form or in the E- (=trans-)form, furthermore as a mixture of these forms, the Z-form being preferred.

Salts are primarily the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, hydrohalic acids, such as hydrochloric acid, sulphuric acid, or phosphoric acid. Suitable organic acids are, for example, carboxylic, phosphonic, sulphonic or sulphamic acids, for example acetic acid, propionic acid, octanoic acid, decanoic acid, dodecanoic acid, glycolic acid, lactic acid, 2-hydroxybutyric acid, gluconic acid, glucose-monocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, maleic acid, hydroxymaleic acid, methylmaleic acid, cyclohexanecar-boxylic acid, benzoic acid, salicylic acid, 1- or 3-hydroxy-naphthyl-2-carboxylic acid, 3,4,5-trimethoxybenzoic acid, 2-phenoxybenzoic acid, 2-aceto-xybenzoic acid, 4-aminosalicylic acid, phthalic acid, phenylacetic acid, glu-curonic acid, galacturonic acid, methane- or ethane-sulphonic acid, 2-hydroxyethanesulfonic acid, ethane-1,2-disulphonic acid, benzenesulphonic acid, 2-naphthalenesulphonic acid, 1,5-naphthalene-disulphonic acid, N-cyclohexylsulphamic acid, N-methyl-, N-ethyl- or N-propyl-sulphamic acid, or other organic protonic acids, such as ascorbic acid.

For isolation or purification purposes it is also possible to use pharmaceutically unacceptable salts, for example picrates or perchlorates. Only the pharmaceutically acceptable salts or free compounds (if the occasion arises, in the form of pharmaceutical preparations) attain therapeutic use, and these are therefore preferred.

In view of the close relationship between the novel compounds in free form and in the form of their salts, including those salts that can be used as intermediates, for example In the purification or identification of the novel compounds, hereinbefore and hereinafter any reference to the free compounds is to be understood as referring also to the corresponding salts, as appropriate and expedient.

The compounds of formula I have valuable pharmacological properties, as described hereinbefore and hereinafter.

The efficacy of the compounds of formula I as inhibitors of microtubule depolymerisation may be proved as follows:

Stock solutions of the test compounds (10 mM) are prepared in DMSO and stored at −20° C. Microtubule protein is extracted from pigs' brain by two cycles of temperature-dependent depolymerisation/polymerisation, as known (see siehe Weingarten et al., Biochemistry 1974; 13: 5529–37). Working stock solutions of microtubule protein (i.e. tubulin plus microtubule-associated proteins) are stored at −70° C. The degree of test-compound-induced polymerisation of microtubule protein is determined basically as already known (see Lin et al., Cancer Chem. Pharm. 1996; 38:136–140). To summarise, 5 µl stock solution of the test compound in 20 times the desired final concentration are admixed with 45 µl of water at room temperature and then placed on ice. A working aliquot strain of pigs' brain microtubule protein is rapidly thawed and then diluted to 2 mg/ml in ice-cold 2×MEM buffer (200 ml MES, 2 mM EGTA, 2 mM $MgCl_2$, pH 6.7) [MES=2-morpholinoethanesulphonic acid, EGTA=ethylene glycol-bis-2(2-aminoethyl)-tetraacetic acid]. The polymerisation reaction is started by adding 50 µl if of each diluted microtubule protein to the test compound, followed by incubation of the sample for 5 minutes in a water bath at room temperature. Then, the reaction mixtures are placed in an Eppendorf microcentrifuge and incubated for a further 15 minutes at room temperature. The samples are then centrifuged for 20 minutes at 14,000 rpm at room temperature, in order to separate polymerised from unpolymerised microtubule protein. As an indirect measure of tubulin polymerisation, the protein concentration of the supernatant (which contains the remaining non-polymerised, soluble microtubule protein) is determined by the Lowry method (CD Assay Kit, Bio-Rad Laboratories, Hercules, Calif.), and the optical density (OD) of the colour reaction is measured at 750 nm using a spectrometer (SpectraMax 340, Molecular Devices, Sunnydale, Calif.). The difference in OD's between samples treated with a test compound and vehicle-treated controls is compared with that obtained with incubations containing 25 µM epothilon B (positive control). The degree of polymerisation induced by a test compound is expressed relatively to the positive control (100%). By comparing the activity of several concentrations, the EC50 (concentration at which 50% of the maximum polymerisation occurs) can be determined. For compounds of formula I, the EC50 lies in the range of 1 to 100, preferably in the range of 1 to 50, especially from 1 to 10 µM.

The efficacy against tumour cells may be demonstrated in the following way:

Stock solutions of the test compounds (10 mM) are prepared in DMSO and stored at −20° C. Human KB-31 and (multidrug-resistant, P-gp170 expressing) KB-8511 epidermoid carcinoma cells originate from Dr. M. Baker, Roswell Park Memorial Institute (Buffalo, N.Y., USA) (description: see also Akiyama et al., Somat. Cell. Mol. Genetics 11 117–120 (1985) and Fojo A., et al., Cancer Res. 45, 3002–3007 (1985)—KB-31 and KB-8511 are both derivatives of the KB cell line (ATCC) and are human epidermis carcinoma cells. KB 31 cells may be cultivated in monolayers using Dulbecco's modified Eagle's medium (D-MEM) with 10% foetal calf serum (M.A. Bioproducts), L-glutamine (Flow), penicillin (50 units/ml) and streptomycin (50 µg/ml (Flow); they then grow at a duplication time of ca. 22 hours, and their relative plating efficiency it ca. 60%. KB-8511 is a variant derived from the KB-31 cell line, which was obtained using colchichine treatment cycles, and has an approximately 40 times relative resistance to colchichine compared with KB-31 cells. The cells are incubated at 37° C. in an incubator with 5% v/v $CO_2$ and at 80% relative humidity with MEMAlpha medium which contains ribonucleosides and desoxyribonucleosides (Gibco BRL), complemented with 10 IU penicillin, 10 µg/ml streptomycin and 5% foetal calf serum. The cells are seeded in a quantity of $1.5 \times 10^3$ cells/well in 96-well microtitre plates, and incubated over night. Serial dilutions of the test compounds in culture medium are added on day 1. The plates are then incubated for a further 4 days, after which the cells are fixed with 3.3% v/v glutaraldehyde, washed with water and dyed with 0.05% w/v methylene blue. After washing, the dye is eluted with 3% HCl and the optical density measured at 665 nm with a SpectraMax 340 (Molecular Devices, Sunnyvale, Calif.). IC50 values are determined by adaptation of mathematical curves, using the SofrPro2.0 programme (Molecular Devices, Sunnyvale, Calif.) and using the formula [(OD treated)—(OD start) [/](OD control)—(OD start)]×100. The IC50 is defined as the concentration of a test compound at the end of the incubation period, which led to 50% of the cell count per well compared with the control (concentration at semi-maximum inhibition of cell growth). Compounds of formula I thus preferably show an IC50 in the range of $0.1 \times 10^{-9}$ to $500 \times 10^{-9}$ M, preferably between 0.2 and 50 nM.

Tests on other tumour cells lines can also be carried out in a comparable manner. The ranges of the $IC_{50}$ values (the ranges measured for compounds of the formula I, especially for the preferred compounds of formula I) are given in the square parentheses. A459 (lungs; ATCC CCL 185) [preferred IC$_{50}$ 0.01×10$^{-9}$ to 500×10$^{-9}$M, preferably between 0.01 and 100 nM], NClH460 (lungs) [preferred IC$_{50}$ 0.01×10$^{-9}$ to 500×10$^{-9}$M, preferably between 0.02 and 200 nM], HCT-15 (colon; ATCC CCL 225—ATCC= American Type Culture Collection (Rockville, Mass., USA)) [preferred IC$_{50}$ 0.01×10$^{-9}$ to 500×10$^{-9}$M, preferably between 0.05 and 500 nM], HCT-116 (colon) [preferred IC$_{50}$ 0.01×10$^{-9}$ to 500×10$^{-9}$M, preferably between 0.05 and 200 nM], Du145 (prostate; ATCC No. HTB 81; see also Cancer Res. 37, 4049–58 [1978]) [preferred IC50 0.01×10$^{-9}$ to 500×10$^{-9}$M, preferably between 0.05 and 500 nM], PC-3M (prostate—hormone-insensitive derivative, obtained from Dr. I. J. Fidler (MD Anderson Cancer Center, Houston, Tex., USA) and derived from PC-3, a cell line that is obtainable from the ATCC (ATCC,CRL 1435)) [preferred IC$_{50}$ 0.01× 10$^{-9}$ to 500×10$^{-9}$M, preferably between 0.05 and 500 nM], MCF-7 (breast; ATCC HTB 22) [preferred IC$_{50\ 0.01\times 10}$$^{-9}$ to 500×10$^{-9}$M, preferably between 0.02 and 200 nM], MCF-7/ADR (breast, multidrug-resistant; see also Blobe G.C.et al., J. Biol. Chem. (1983), 658–664; the cell line is to a large extent resistant (360- to 2400-fold) to doxorubicin and vinca alkaloids in comparison with MDR-7 "wild-type" cells)) [preferred IC$_{50}$ 0.01×10$^{-9}$ to 500×10$^{-9}$M, preferably between 0.1 and 1000 nM], or MDA231.

The in vivo efficacy may be demonstrated as follows: The models used are xeno-transplants of tumours, such as KB-31 or KB-8511 epidermoid tumours, in mice. The anti-tumour efficacy of the test compounds may be measured in female BLB/c nu/nu mice for example against the corresponding subcutaneously transplanted cell line. To this end, tumour fragments of about 25 mg are implanted into the left side of each of the mice (for example 6 animals per dose). The test compound is administered for example on day 11 after transplantation in different dosages (for example 0.1; 0.5; 1; 5 and 10 mg/kg), if desired repeating the administration, if required several times, after between two days and two weeks. The volumes of the tumours are determined for example after about 2 to 4 weeks (e.g. two weeks after the start of treatment). The tumour volumes are calculated by measuring the tumour diameter along two vertically arranged axes and according to published methods (see Evans et al., Brit. J. Cancer 45, 466–8 (1982)). The anti-tumour efficacy is determined as the mean increase in tumour volume of the treated animals divided by the mean Increase in tumour volume of the untreated animals (controls) and, after multiplication by 100, is expressed as T/C %. Tumour regression (given in %) is calculated as the smallest mean tumour volume (Vt) in relation to the mean tumour volume at the start of treatment (Vo) according to the formula $$\% \text{ regression} = [1-(Vt/Vo)] \times 100.$$

In this case also, other cell lines can be used, for example those named above in the demonstration of efficacy against tumour cells.

Owing to these properties, the compounds are suitable for the treatment of proliferative diseases, especially tumour diseases, including metastases; for example solid tumours such as lung tumours, breast tumours, colorectal tumours, prostate tumours, melanomas, brain tumours, pancreas tumours, neck tumours, bladder tumours, neuroblastomas, throat tumours, but also proliferative diseases of blood cells, such as leukaemia; also for the treatment of other diseases which respond to treatment with microtubule depolymerisation inhibitors, such as psoriasis.

A compound of formula I can be administered alone or in combination with one or more other therapeutic agents; possible combination therapy taking the form of fixed combinations or the administration of a compound of the invention and one or more other therapeutic agents being staggered or given independently of one another, or the combined administration of fixed combinations and one or more other therapeutic agents. A compound of formula I can besides or in addition be administered for tumour therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemopreventive therapy, for example in patients at risk.

Therapeutic agents for possible combination are especially one or more antiproliferative, cytostatic or cytotoxic compounds, for example one or more chemotherapeutic agent(s) selected from the group comprising the classical chemotherapeutic agents, an inhibitor of polyamine biosynthesis, an inhibitor of protein kinase, especially of serine/threonine protein kinase, such as protein kinase C, or of tyrosine protein kinase, such as epidermal growth factor receptor protein tyrosine kinase, a cytokine, a negative growth regulator, such as TGF-β or IFN-β, an aromatase inhibitor, and a classical cytostatic.

Compounds according to the invention are not only for the (prophylactic and preferably therapeutic) treatment of humans, but also for the treatment of other warm-blooded animals, for example of commercially useful animals, for example rodents, such as mice, rabbits or rats, or guinea-pigs. They may also be used as a reference standard in the test systems described above to permit a comparison with other compounds.

A compound of formula I may also be used for diagnostic purposes, for example with tumours that have been obtained from warm-blooded animal "hosts", especially humans, and implanted into mice to test them for decreases in growth after treatment with such a compound, in order to investigate their sensitivity to the said compound and thus to improve the detection and determination of possible therapeutic methods for neoplastic diseases in the original host.

Within the groups of preferred compounds of formula I mentioned hereinafter, definitions of substituents from the general definitions mentioned hereinbefore may reasonably be used, for example, to replace more general definitions with more specific definitions or especially with definitions characterized as being preferred; the definitions characterised as being preferred, or exemplary ("e.g.", "such as", "for example", are preferred.

Preference is given to a compound of formula I, wherein

T is O or NH;

A is a radical of formula Ia, which is bonded to the radical of the molecule of formula I by one of the two carbon atoms marked by an arrow, preferably by the carbon atom in p-position to X; and wherein X is S; O; NH; N(alk); wherein alk is alkyl, (especially lower alkyl), hydroxy-lower alkyl, unsubstituted or substituted amino-lower alkyl or carbamoyl-lower alkyl; C(Rk*)=N, N=C(Rk*) or C(Rk*)=C (Rk**), wherein Rk* and Rk**, independently of one another, are H, Alkyl (especially lower alkyl), halogen-lower alkyl or hydroxy-lower alkyl, or also substituted or unsubstituted amino-lower alkyl or carbamoyl-lower alkyl; and Rk is H, lower alkyl, halogen-lower alkyl or hydroxy-lower alkyl or also unsubstituted or substituted amino-lower alkyl or carbamoyl-lower alkyl;

either Y is OH and Y* is hydrogen, or —Y and —Y* together form a bond;

R is hydrogen, lower alkyl or halogen lower alkyl;

and Z is O, or —Z— is a bond between the two binding carbon atoms;

or salts thereof.

Preference is also given to a compound of formula I wherein

T is O;

A is a radical of formula Ia

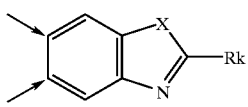

(Ia)

which is bonded to the radical of the molecule according to formula I by one of the two carbon atoms marked with an arrow, and wherein X is S; O; NH; N(alk); wherein alk is alkyl; N(ar), wherein ar is aryl; C(Rk*)=N, N=C(Rk*) or C(Rk*)=C(Rk**), wherein Rk* and Rk**, independently of one another, are H, alkyl (especially lower alkyl), halogen-lower alkyl or hydroxy-lower alkyl; and Rk is H, alkyl (especially lower alkyl), halogen-lower alkyl or hydroxy-lower alkyl;

either Y is OH and Y* is hydrogen, or —Y and —Y* together form a bond (so that they form a double bond together with the adjoining bond connecting the two —Y and —Y* bearing carbon C atoms);

R is hydrogen, lower alkyl or halogen-lower alkyl;

and Z is O, or —Z— is a bond between the two binding carbon atoms;

or salts thereof.

Special preference is given to a compound of formula I wherein

T is NH or especially O;

A is a radical of formula Ia, which is bonded to the radical of the molecule according to formula I by one of the two carbon atoms marked with an arrow, and wherein X is S, O, NH, N(CH$_3$), N(CH$_2$CH$_2$OH), N(CH$_2$CH$_2$NH$_2$), N(CH$_2$CH$_2$N(CH$_3$)$_2$), N(CH$_2$C(O)NH$_2$), C(Rk*)=N or CH=C(Rk*), wherein Rk* is H, methyl, hydroxymethyl, (CH$_2$CH$_2$OH), (CH$_2$CH$_2$NH$_2$), (CH$_2$CH$_2$N(CH$_3$)$_2$), (CH$_2$C(O)NH$_2$), or also fluoromethyl;

and

Rk is hydrogen, methyl, ethyl, hydroxymethyl, hydroxyethyl, aminomethyl, aminoethyl, dimethylaminomethyl, carbamoylmethyl or also fluoromethyl;

R is hydrogen, methyl, ethyl or fluoromethyl; and

Z is O, or —Z— is a bond between the two binding carbon atoms;

or salts thereof; whereby the bond characterised by a wavy line means that the compound of formula I is present in cis- or trans-form, preferably in cis-form.

Special preference is given to a compound of formula I wherein

T is NH or especially O;

A is a radical of formula Ia, which is bonded to the radical of the molecule according to formula I by one of the two carbon atoms marked with an arrow, add wherein X is S, O, NH, N(CH$_3$) or N(CH$_2$CH$_2$OH), or isC(Rk*)=N or CH=C(Rk*), wherein Rk* is H, methyl or hydroxymethyl, or also fluoromethyl;

and

Rk is hydrogen, methyl or hydroxymethyl, or also fluoromethyl, or ethyl;

R is hydrogen, methyl, ethyl or fluoromethyl; and

Z is O, or —Z— is a bond between the two binding carbon atoms;

or salts thereof; whereby the bond characterised by a wavy line means that the compound of formula I is present in cis- or transform, preferably in cis-form.

Particular preference is given to a compound of formula I wherein

T is NH or especially O;

A means a radical of formula Ia, which is bonded to the radical of the molecule according to formula I by one of the two carbon atoms marked with an arrow, and wherein X is S; or is further selected from the group consisting of NCH$_3$ and CH=CH and in a broader aspect of the invention O and N(CH$_2$CH$_2$OH);

and

Rk is H, methyl, ethyl, hydroxymethyl, hydroxyethyl, especially 2-hydroxyethyl, aminomethyl, aminoethyl, especially 2-aminoethyl, or carbamoyl, preferably methyl;

R is hydrogen, lower alkyl or halogen lower alkyl; and

Z is O, or —Z— is a bond between the two binding carbon atoms, or a salt thereof.

Particular preference is given to a compound of formula I wherein

T is O;

A means a radical of formula Ia, which is bonded to the radical of the molecule according to formula I by one of the two carbon atoms marked with an arrow, and wherein X is S; or is further selected from the group consisting of O, NCH$_3$, CH=CH and N(CH$_2$CH$_2$OH);

and

Rk is H, methyl or hydroxymethyl, or ethyl, preferably methyl;

R is hydrogen, lower alkyl or halogen lower alkyl; and

Z is O, or —Z— is a bond between the two binding carbon atoms, or a salt thereof.

Of the compounds and (where appropriate) groups including the compounds, as mentioned hereinbefore and hereinafter, the following are preferred in particular (the free compounds being understood to mean also the corresponding salts):

(a) compounds of formula I, wherein X is S;

(b) compounds of formula I, wherein X is O;

(c) compounds of formula I, wherein X is NH;

(d) compounds of formula I, wherein X is N—CH$_3$;

(e) compounds of formula I, wherein X is CH=C(Rk*), in which Rk* meansCH$_3$ or CH$_2$OH;

(f) compounds of formula I, wherein X is C(Rk)=N, in which Rk means CH$_3$ or CH$_2$OH;

(g) compounds of formula I, wherein Z is O [also provided that they fall within one of the definitions (a) to (f)];

(h) compounds of formula I, wherein —Z— is a bond [also if they fall within one of the definitions (a) to (f)];

(i) compounds of formula I, wherein the bond characterised by a wavy line is present in such a way that the compound of formula I is in cis-form;

(j) compounds of formula I, wherein Y is OH and Y* is hydrogen; as well as, furthermore (k) compounds of formula I, wherein X is N(CH$_2$CH$_2$OH);

(l) compounds of formula I, wherein X is N(CH$_2$CH$_2$NH$_2$);

(m) compounds of formula I, wherein X is N(CH$_2$C(O)NH$_2$); further (n) compounds of formula I, wherein X is C(Rk*)=CH, in which Rk* means CH3 or CH$_2$OH;

(o) compounds of formula I, wherein T is O;

(p) compounds of formula I, wherein T is NH;

(q) compounds of formula I, wherein X is CH=C(Rk*), in which Rk* means H; or (r) compounds of formula I, wherein X is C(Rk)=N, in which Rk means H.

In the compounds named under the above definitions (a) to (r), the remaining radicals respectively have the meanings given hereinbefore and hereinafter for compounds of formula I, especially those characterised as being preferred meanings. Of the compounds of formula I and their salts falling within definitions (a) to (r), particular preference is given to those in which the radical A of formula Ia is linked by the bond in para position to X (i.e. ◀A is a radical of formula

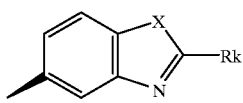

wherein the radicals X and Rk have the meanings given for compounds of formula I).

Very preferred is a compound of formula I, in which T is NH or especially O; ◀A is a radical of formula

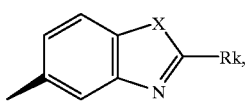

wherein X is sulphur and Rk is methyl, Z is oxygen or —Z— is a bond, and Y* and Y* or —Y and —Y* have the above meanings, especially either Y is hydroxy and Y* is hydrogen, or especially —Y and —Y* together form a bond, or a salt thereof.

Particular preference is also given to a compound of formula I wherein

T is NH or especially O; ◀A means a radical selected from the radicals of formulae

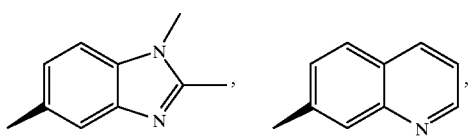

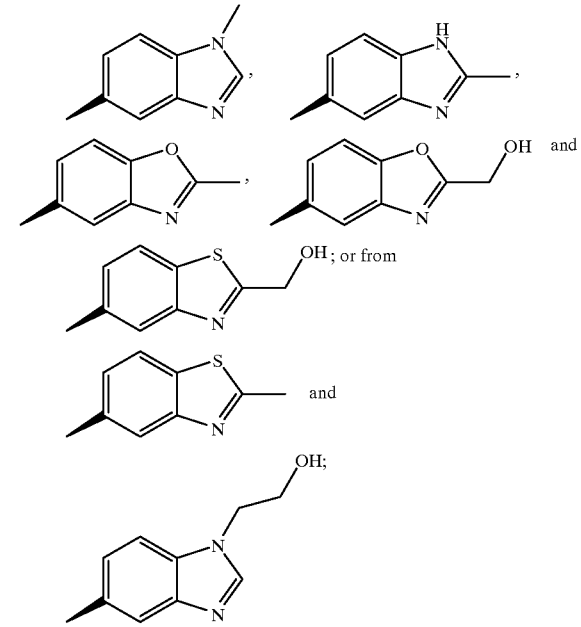

Z is oxygen or —Z— is a bond, and Y and Y* or —Y and —Y* are defined as hereinbefore or hereinafter, especially either Y is hydroxy and Y* is hydrogen, or —Y and —Y* together form a bond, or a salt thereof.

Especially preferred are the compounds named in the examples, or salts thereof (especially pharmaceutically acceptable salts), provided that a salt-forming group is present.

The compounds of formula I may be prepared by methods known per se preferably in that a) an acid of formula II,

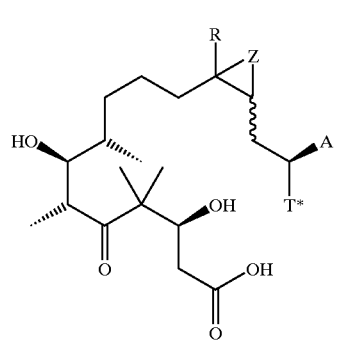

(II)

wherein T* is hydroxy, NH$_2$, NH(alkyl) or N$_3$ and (alkyl), A, Z and R have the meanings given for compounds of formula I, and wherein functional groups that should not participate in the reaction (especially the two OH groups at C-3 and C-6) are present if necessary in protected form, is cyclised, if T*=N$_3$, this taking place after reduction of the azide group, and then if necessary any protecting groups are removed, and, if desired, an obtainable compound of formula I is converted into a different compound of formula I; an obtainable free compound of formula I is converted into a salt; an obtainable salt of a compound of formula I is converted into another salt or the free compound of formula I; and/or obtainable isomeric mixtures of compounds of formula I are separated into the individual isomers;

DETAILED DESCRIPTION OF THE PREFERRED PROCESS VARIANTS

In the following description of the detailed process conditions, the starting products and the reactions, if not otherwise stated, T, A, X, Y, Z, R, Rk and Rk* have the meanings given for compounds of formula I.

Process a):

A compound of formula II may be present in free form, or if the reaction of functional groups which should not participate in the reaction is to be prevented, in a form in which the functional groups that do not participate are present in protected form.

If one or more other functional groups, for example hydroxy or amino, in a compound of formula II are or need to be protected, because they should not take part in the reaction, these are those usually used in the synthesis of peptide compounds, and also of cephalosporins and penicillins, as well as nucleic acid derivatives and sugars. The protecting groups may already be present in precursors and should protect the functional groups concerned against unwanted secondary reactions, such as acylations, etherifications, esterifications, oxidations, solvolysis, and similar reactions. The protecting groups for functional groups in starting materials whose transformation should be avoided, in particular hydroxy or amino groups, include especially the conventional protecting groups that are normally used in the synthesis of peptide compounds, cephalosporins, penicillins or nucleic acid derivatives and sugars. In certain cases, the protecting groups may, in addition to this protection, effect a selective, for example stereoselective, course of reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable for the reactions mentioned hereinabove and hereinafter.

The protection of functional groups by such protecting groups, the protecting groups themselves, and their removal reactions are described for example in standard reference works, such as J. F. W. McOmie, "Protective Groups in Organic Chemistry", Plenum Press, London and New York 1991, in T. W. Greene, P. G. M. Wuts, "Protective Groups in Organic Synthesis", $2^{nd}$ edition, John Wiley & Son Inc., 1981, in "The Peptides"; Volume 3 (E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Protecting groups are preferably used analogously to the groups named in the examples (especially hydroxy protecting groups of the tri-lower alkylsilyl type), and introduced analogously to the methods described therein, and removed if necessary.

Cyclisation may be effected under conventional conditions. If T* is a hydroxy group, then cyclisation corresponds to macrolactonisation. If T* is $NH_2$ or NH(alkyl), then it corresponds to lactam formation. If T* is an azide group ($N_3$), then first of all it must be reduced, and subsequently lactam formation is also effected. Alternatively, treatment of the azido acid with $Ph_3P$ may directly lead to the macrolactam.

The lactonisation (formation of a lactone of formula I or of a protected derivative thereof with T=O) from a compound of formula II (or from a protected derivative thereof) preferably takes place in the presence of a coupling medium, for example a compound that can convert the free acid of formula II into an activated form, for example by forming an anhydride or an acid halide, especially by a reaction with an acid halide such as an arylcarbonyl halide, especially arylcarbonyl chloride, whereby aryl means phenyl in particular, which is unsubstituted or is substituted once or many times, preferably up to three times, by a substituent preferably selected from halogen such as chlorine, nitro, lower alkoxy, lower alkoxy-carbonyl and cyano, and if necessary in the presence of a base, possibly a tertiary nitrogen base, such as a tri-lower alkylamine, e,g, triethylamine, and/or a di-lower alkylaminopyridine, such as N,N-dimethylaminopyridine, at preferred temperatures of between −10 and 100° C., preferably between 0 and 75° C. The reaction may also be carried out in such a way that first of all an activated form of the acid of formula II is produced, for example an anhydride, and then this anhydride is reacted to the corresponding lactone, whereby both reactions can also follow one another in one and the same reaction mixture. The reactions are preferably effected in suitable solvents or solvent mixtures, such as ethers, e.g. tetrahydrofuran, or aromatic hydrocarbons such as benzene or toluene.

The lactam formation (macro-lactamisation) is effected under conditions which are customary for linking carboxylic acid amide bonds, whereby coupling reagents conventional in peptide chemistry, such as DCC/HOBt, HBTU, TPTU, HATU inter alia may be employed. It may also take place using for example diphenylphosphoryl azide or bromotripyrrolidino-phosphonium hexafluorophosphate.

The reduction of the azide group (if T*=$N_3$) takes place by methods known per se, in particular using triphenylphosphine or by catalytic hydrogenation (see also WO 99/02514, where known methods are described).

Reactions:

In the additional process steps, carried out as desired, functional groups of the starting compounds which should not take part in the reaction may be present in unprotected form or may be protected for example by one or more of the protecting groups mentioned hereinabove under process a). The protecting groups are then wholly or partly removed according to one of the methods described under process a).

The compounds of formula I, in which Z is O, may be produced from those compounds of formula I in which —Z— is a bond which forms a double bond together with the adjacent bond, by means of epoxidation according to methods known per se, for example with a peroxide such as m-chloroperbenzoic acid or preferably dimethyl dioxirane $H_2O_2$ in the presence of catalytic amounts of $CH_3ReO_3$, or methyl-trifluoromethyl dioxirane, under conventional conditions, for example by reacting in a suitable solvent, such as a hydrocarbon, e.g. benzene, an ester such as ethyl acetate, a halogenated hydrocarbon, such as dichloromethane, a ketone such as acetone, a nitrile such as acetonitrile, water, or mixtures thereof, if desired in the presence of a complexing agent such as an ethylene diamine tetraacetate, e.g. disodium ethylene diamine tetraacetate, and/or a base such as a metal carbonate or metal hydrogen carbonate, e.g. sodium hydrogen carbonate, at a reduced temperature, for example in the range −80 to +10° C., preferably from −50 to +5° C.

Compounds of formula I in which Y is hydroxy and Y* is hydrogen may be converted, by eliminating water, into those compounds of formula I in which —Y and —Y* together form a bond that forms a double bond together with the bond present between the two binding carbon atoms. To do this, free OH groups (especially at C-3 and C-7) are preferably formylated with the assistance of the mixed anhydride of formic acid and acetic acid; subsequently, the formyl derivative is treated with DBU {1,8-diazabicyclo[2.2.2]undec-7-ene (1.5-5)} in dichloroethane, which leads to elimination of formic acid and the formation of a double bond between C-2 and C-3. Finally, the formyl protecting group is removed from the OH group at C-7 and from any further OH groups, for example with $NH_3$/methanol.

Compounds of formula I, wherein T is O, may be converted into the corresponding compounds of formula I in which T is NH or N(alkyl), by reacting the compound with T=O by forming a pi-allylpalladium complex, for example using palladium tetrakis triphenylphosphine, followed by treatment with a corresponding primary amine [$NH_3$ or $H_2N$(alkyl), or $NaN_3$] and subsequent lactam formation as described under process a).

Salts of compounds of formula I with a salt-forming group may be prepared in a manner known per se. Acid addition salts of compounds of formula I may thus be obtained e.g. by treatment with an acid or with a suitable anion exchange reagent.

Salts can usually be converted to free compounds, e.g. by treating with suitable basic agents, for example with alkali metal carbonates, -hydrogencarbonates, or -hydroxides, typically potassium carbonate or sodium hydroxide.

Stereoisomeric mixtures, e.g. mixtures of diastereoisomers, can be separated into their corresponding isomers in a manner known per se by means of suitable separation methods. Diastereoisomeric mixtures may thus be separated into their individual diastereoisomers by means of fractionated crystallization, chromatography, solvent distribution, and similar procedures. This separation may take place either at the stage of one of the starting compounds or in a compound of formula I itself. Enantiomers may be separated through the formation of diastereoisomeric salts, for example by salt formation with an enantiomer-pure chiral acid, or by means of chromatography, for example by HPLC, using chromatographic substrates with chiral ligands. (Enantiomer separation is normally effected at the intermediate stage).

Starting Materials:

The starting materials are known, may be produced by known processes or are commercially available, or they may be produced as described in the following:

In the following preparation processes for intermediates, functional groups which are to be in protected form can be protected if necessary at suitable stages, whereby selective protection or deprotection is also possible. The protecting groups and the methods of introducing and/or removing them correspond to those named above under process a), especially those named in the above-mentioned standard reference works or, in particular, in the examples. As a rule, protecting groups are not mentioned in the following; the following examples show where the usage of the protecting groups is appropriate or necessary and can therefore be regarded as a preferred instruction as to when protecting groups should be used and if compounds should be produced with other radicals. In the following, protecting groups are not mentioned at all the points where they are appropriately used. The person skilled in the art is clear as to where this usage ought to or must occur.

For example, compounds of formula II, wherein T* is OH, are obtained whereby an

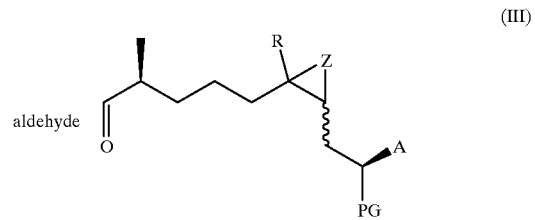

(III)

wherein A, R and Z have the meanings given for compounds of formula I and PG is a protected hydroxy group, especially tri-lower alkylsilyloxy, such as tert-butyl dimethylsilyloxy, is reacted in the presence of a strong base, such as lithium diisopropylamide, in a suitable solvent such as an ether, e.g. tetrahydrofuran, at preferred temperatures of between −80 and 25° C., preferably between −80 and 0° C., with a carboxylic acid of formula IV

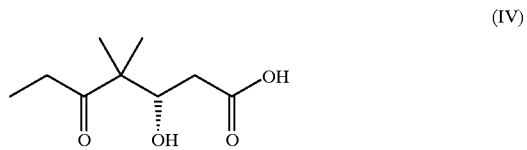

(IV)

wherein the OH group is in protected form (for example as ten-butyl dimethylsilyloxy ether) [if necessary, the protecting group is removed from the protected hydroxy groups either subsequently or later in the reaction sequence, as described above or analogously to the examples].

A compound of formula III may be produced, whereby an alcohol of formula V,

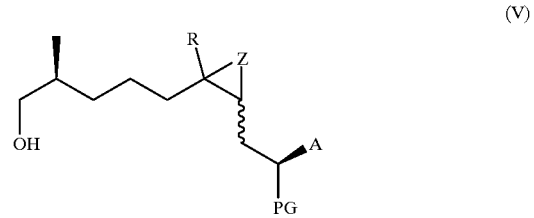

(V)

wherein A, R and Z have the meanings given for compounds of formula I and PG has the meanings given for compounds of formula III, is oxidised under conditions that are generally known for the oxidation of primary alcohols to aldehydes, for example using oxalyl chloride, acetanhydride, trifluoroacetanhydride, dicyclohexylcarbodiimide, preferably oxalyl chloride and dimethyl sulphoxide, in a suitable solvent such as a halogenated hydrocarbon, e.g. dichloromethane, at a temperature of between −100 and 0° C., preferably between −80 and −20° C.

A compound of formula V may be obtained by reacting a compound of formula VI,

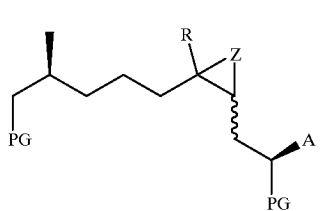

(VI)

wherein R, Z and A have the meanings given for compounds of formula I and the radicals PG, independently of one another, mean protected hydroxy, by means of removal of the protecting group from the primary OH group, for example as described above or analogously to the methods described in the examples.

A compound of formula VI may be obtained in that a compound of formula VII,

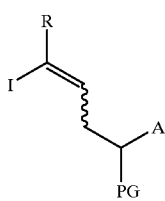

(VII)

(protected if required) wherein R and A have the meanings given for compounds of formula I and PG means protected hydroxy, is reacted with a compound of formula VIII,

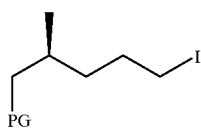

(VIII)

wherein PG means a protected hydroxy group. In this reaction, a Cu/Zn pair is preferably prepared in a suitable solvent such as an aromatic hydrocarbon, e.g. benzene, in the presence of ethylene bromide and a tri-lower alkylsilyl halide such as trimethylsilyl chloride, at an elevated temperature, e.g. between 30 and 90° C., preferably at 90° C.; after adding the compound of formula VIII in a suitable solvent, e.g. a dimethylacetamide/benzene mixture, and afterwards adding a tri-lower alkylsilyl triflate, such as trimethylsilyl triflate, and optionally further dimethylacetamide, at a temperature of between 30 and 90° C., especially 60 to 70° C., the reaction continues; then, tetrakis(triphenylphosphine)-palladium is added, and finally the compound of formula VII is added, if necessary with further solvent such as benzene, and the reaction is completed at preferred temperatures of between 30 and 90° C., especially at 60° C., whereby a compound of formula VI is obtained, in which —Z— is a bond (if desired, this can be convened into the corresponding compound of formula VI in which Z is O under conditions analogous to those given below for the epoxidation reactions).

A compound of formula VII may be obtained in that an aldehyde of formula IX,

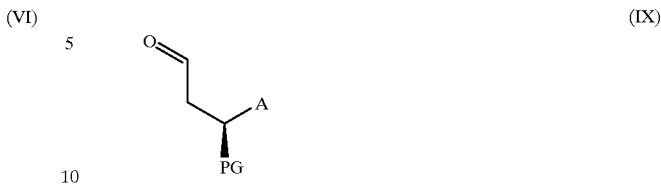

(IX)

(protected if required), wherein A and PG have the meanings given for compounds of formula VI, is reacted with a suspension of [Ph$_3$PCHIR]$^+$I$^-$ (in which R has the meanings given for R in formula I), to which is added sodium hexamethyl disilazide (NaHMDS) which is dissolved in a suitable solvent such as a cyclic ether, e.g. tetrahydrofuran; the mixture is then stirred at temperatures of between −80 and −20° C., and the compound of formula IX is added (preferably dissolved in the same solvent, e.g. tetrahydrofuran) and reacted in the same temperature range to form the compound of formula VII.

The aldehyde of formula IX is preferably obtained in that a compound of formula X

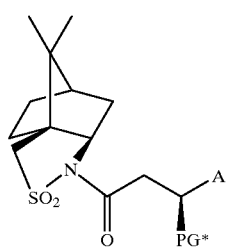

(X)

(protected if required), wherein A has the meanings given for compounds of formula I and PG* is a hydroxy group (in which case an appropriate protecting group is added first of all, e.g. tri-lower alkylsilyl) or PG is protected hydroxy, is reacted with a hydride, especially with diisobutyl aluminium hydride, in a suitable solvent such as a halogenated hydrocarbon, especially dichloromethane, at preferred temperatures of between −20 and −90° C., e.g. at −78 to −40° C.

A compound of formula X may be preferably obtained in that an aldehyde compound of formula XI,

A—CHO    (XI)

(protected if required),wherein A has the meanings given for compounds of formula I, is reacted with a reagent which is obtained, in particular, firstly by preparing a solution of a trilower alkylborane, such as triethylborane, in a suitable solvent such as a hydrocarbon, e.g. hexane, adding a sulphonic acid such as trifluoromethanesulphonic acid, then maintaining firstly temperatures of between 10 and 50° C., and after adding a suitable halogenated hydrocarbon, such as dichloromethane, again maintaining the same temperature range, and finally mixing with (2R)-acetylbornane-10,2-sultam and preferably a base dissolved in the same solvent, especially a tri-lower alkylamine, such as Hünig's base; at a temperature of −80 to 0° C., and then the aldehyde of formula XI is added, preferably dissolved in a suitable solvent such as a halogenated hydrocarbon, for example dichloromethane, and reacted in the latter temperature range.

Compounds of formula IV, formula VIII and aldehydes of formula XI are known, may be produced by processes known per se or are commercially available.

An alternative and preferred process for the production of a compound of formula II (especially a hydroxy-protected compound), wherein T* is OH and the remaining radicals have the meanings given for the compounds of formula I [in particular, wherein R means methyl, Prot means tert-butyldimethylsilyl, Y is hydroxy (or in protected form tert-butyl-dimethylsilyloxy) and Y* is hydrogen], starts with the following educts (with the respectively mentioned meanings, especially the preferred meanings):

By reacting a compound of formula XII,

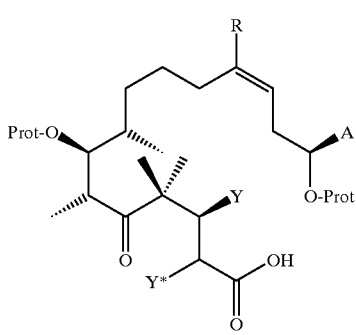

(XII)

wherein Prot means a hydroxy protecting group, especially tert-butyldimethylsilyl, and the remaining radicals have the meanings given for compounds of formula I (protected if required), and removing the primary hydroxy protecting group, for example with tetrabutyl-ammonium fluoride in an ether such as tetrahydrofuran, at preferred temperatures of 0 to 50° C., especially at room temperature, the corresponding protected compound of formula II is obtained.

The compound of formula XII is preferably obtained in that an ester of formula XII*,

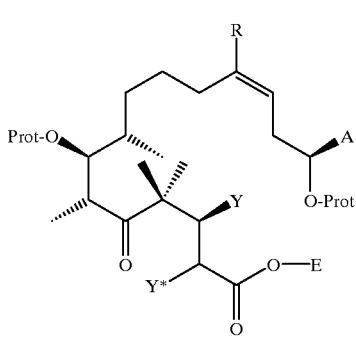

(XII*)

wherein the radicals have the above-mentioned meanings and E is alkyl, especially lower alkyl, such as methyl, or also aryl or aryl lower alkyl, is saponified, preferably with an alkali metal hydroxide, such as LiOH, in an alcohol such as isopropanol, in the presence of water and at temperatures of ca. 25 to 75° C., especially 50° C.

The compound Of formula XII* is preferably obtained by reacting an olefin of formula XIII

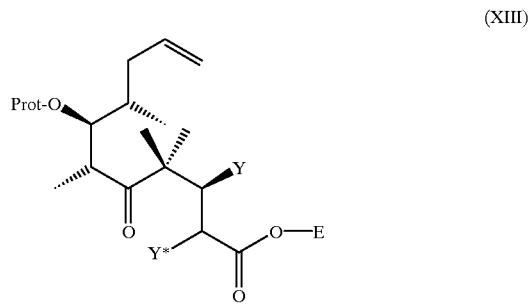

(XIII)

wherein E has the meanings given for compounds of formula XII* and the remaining radicals have the meanings given for compounds of formula XII, with a halide of formula XIV,

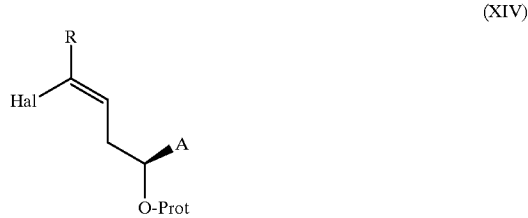

(XIV)

wherein Hal is halogen, especially iodine, Prot is a hydroxy protecting group and the remaining radicals have the meanings given for compounds of formula I, whereby preferably first of all the olefin is reacted with 9-borabicyclononane (9-BBN) in a suitable solvent, such as an ether, e.g. tetrahydrofuran, at temperatures of between 0 and 50° C., especially at room temperature, and then the solution of the resulting trialkylborane is added to a mixture of a carbonate, especially cesium carbonate, in the presence of PdCl$_2$(dppf)$_2$ (dppf= diphenylphosphinylferrocen), triphenylarsine and XIV in a suitable solvent, such as dimethylformamide, and the reaction takes place at temperatures of between −25 and 30° C., especially between −10° C. and room temperature, to form the compound of formula XII*.

The compound of formula XIV is analogous to the compound of formula VII and may be produced in the same way (especially if Hal=I).

The compound of formula XII) is produced in that a compound of formula XV,

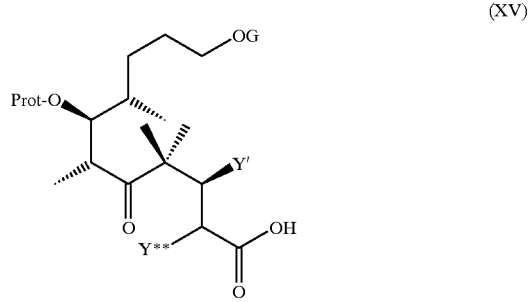

(XV)

wherein G is a protecting group, especially benzyl, and Y** is hydrogen and Y' is protected hydroxy is firstly reacted with dicyclohexyl carbodiimide in the presence of dimethylaminopyridine and an alcohol E—OH, wherein E has the meanings given for compounds of formula XII* and means methyl in particular, if necessary, also in the presence of one or more further suitable solvents such as dichloromethane, at temperatures of between −30 and 40° C., especially between −20 and 25° C.; removal of the protecting group G from the product obtained, if G=benzyl this is effected with hydrogen (preferably at atmospheric pressure) in the presence of a catalyst, such as palladium on carbon, in a suitable solvent such as methanol or ethanol, preferably at temperatures of 0 to 50° C., such as at room temperature, leads to the free alcohol; this is reacted with 2-NO$_2$PhSeCN (Ph=phenyl) in the presence of tributylphosphine at 0 to 50° C., preferably at room temperature, and is then treated with a base such as a carbonate, e.g. sodium hydrogen carbonate, and an oxidation agent such as hydrogen peroxide, at the same temperature.

The compound of formula XV may be preferably produced from a compound of formula XVI,

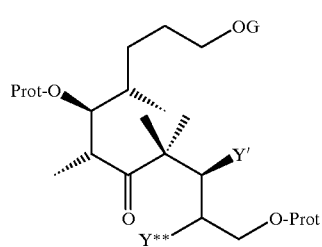

(XVI)

wherein O-Prot has the meanings given for compounds of formula XII and the remaining radicals have the meanings given for compounds of formula XV, whereby first of all the protecting group Prot on the primary OH is removed, if Prot=tert-butyldimethylsilyl e.g. by treatment with camphorsulphonic acid in a suitable solvent, for example, a mixture of an alcohol such as methanol with a chlorinated hydrocarbon such as methylene chloride, at temperatures of between −10 and 25° C., especially at 0° C.; then the resulting alcohol is initially oxidised to the aldehyde, e.g. with (COCl)$_2$ in dimethylsulphoxide in the presence of a base such as triethylamine, and in a chlorinated hydrocarbon such as methylene chloride, at a reduced temperature, preferably between −80 and −50° C., especially at −78° C.; then the aldehyde obtained is oxidised with NaClO$_2$ in the presence of isobutene in a solvent mixture, such as tetrahydrofuran/tert-butanol/phosphate buffer pH 7 at temperatures of between 0 and 50° C., especially at room temperature, to form the acid.

If a compound of formula XII* in which —Y and —Y* together form a bond is desired, this may be produced by eliminating the elements of water (if necessary after removing the protecting groups) from the obtained intermediate of formula XIII, in which Y is hydroxy (optionally protected) and Y* means hydrogen. In order to allow for elimination, in a compound of formula XIII wherein Y is protected hydroxy the protecting group has to be removed first.

A compound of formula XVI is preferably produced from a compound of formula XVII,

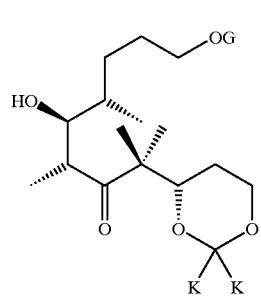

(XVII)

wherein K means lower alkyl, especially methyl, or hydrogen, or the two groups K together form a 5- or six-membered alicyclic ring together with the binding carbon atom, and the remaining radicals have the meanings given for compounds of formula XVI, whereby first of all this compound is reacted with pyridinium-p-toluenesulphonate in a suitable solvent such as methanol, at temperatures of between 0 and 50° C., especially at room temperature, and then the obtainable product is reacted by introducing the protecting group "Prot", for example with a trialkylsilyl trifluoromethane sulphonate, such as tert-butylsilyl-dimethylsilyl-O-trifluoromethane sulphonate.

The compound of formula XVII is produced in that a compound of formula XVIII,

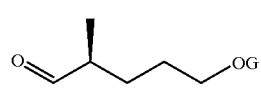

(XVIII)

wherein G has the significance given for compounds of formula XV, but especially means benzyl, is added to the enolate of a compound of formula XIX

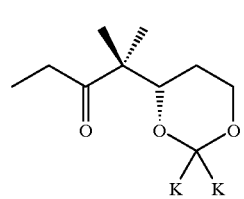

(XIX)

which is formed at a temperature of preferably −80 to −50° C., especially at −78° C., by adding a strong base, such as LDA in a suitable solvent (LDA= lithium diisopropylamide), in which compound K is lower alkyl, especially methyl, or hydrogen, or the two groups K together form a 5- or six-membered alicyclic ring together with the binding carbon atom, and reacted with lithium diisopropylamide in a suitable solvent such as tetrahydrofuran, at the said temperatures, especially at −78° C.

Compounds of formula XIX, especially those in which K means methyl, are known, see e.g. Chem. Eur. J. 2(11), 1477–1482 (1996).

A compound of formula XVIII is preferably produced by oxidation of an alcohol of formula XX,

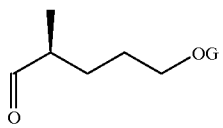

(XX)

wherein G means a protecting group, such as benzyl.

Compounds of formula XX (for example with G=benzyl) are known or may be produced by known processes (see Synlett 1998, 861–864).

An alternative procedure for the preparation of a compound of the formula XIII is by reaction of a compound of the formula XXVII,

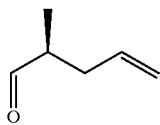

(XXVII)

with a compound of the formula XIX as defined above, which results in a compound of the formula XVII*

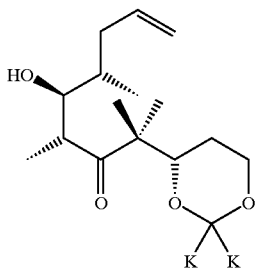

(XVII*)

wherein K and K is defined as described for compounds of the formula XIX. The compound of formula XVII* can then be converted to XIII by the same sequence of reactions as described for XVII except that removal of the protecting group G present in XVII and the following olefin-forming reaction are not necessary.

A compound of formula II, wherein T* is NH or N(alkyl), may be produced as follows:

Starting from a compound of formula X*

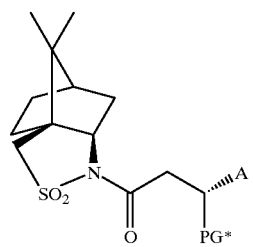

(X*)

which is obtained as a by-product in the preparation of the compound of formula X (see above), in which PG* is a hydroxy group and A has one of the meanings given for compounds of formula I, first of all the OH group is converted into a leaving group (e.g. tosylate, mesylate, inflate). This is then followed by a reaction with a source of azide, for example $NaN_3$ or $Bu_3SnN_3$. A compound of formula XXI is obtained,

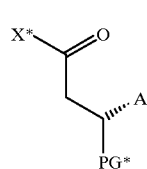

(XXI)

wherein X* is the radical of formula

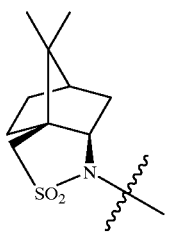

and A has the meanings given for compounds of formula I. This is converted into a protected amino compound by reduction followed by direct introduction of an amino protecting group or by alkylation and subsequent introduction of an amino protecting group to that a group NH—PR or N(alkyl)-PR is obtained, in which PR is an amino protecting group; or it is further handled in the form of the azide group.

The reduction of the azide to the amino group may take place e.g. with triphenylphosphine or by catalytic hydrogenation, and the introduction of the protecting group or alkyl group PR then follows.

A compound of formula XXII is obtained,

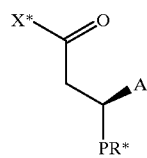

(XXII)

wherein PR* is NH—PR or N(alkyl)-PR as defined above, or is $N_3$ (identical to the compound of formula XXI), and A has the meanings given for compounds of formula I.

These are subsequently reacted to form the corresponding aldehyde of formula XXIII,

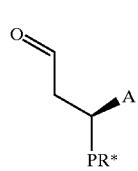

(XXIII)

wherein the radicals have the meanings given for compounds of formula XXII, e.g. with diisobutyl aluminium hydride.

An aldehyde of formula XXIII can also be obtained by initial reaction of (2S)-acetylbornane-1,2-sultam with an aldehyde A-CHO (XI) to provide the enantiomer of a compound of formula X (X**), which is then processed into XXIII in analogy to compound X*. Aldehyde XXIII is then converted to the corresponding vinyl halide with [RCHl-PPh₃]⁺ I⁻ (analogously to the preparation of the analogous oxygen of formula VII, see above; R is as defined under formula I).

The iodide of formula XXIV thus obtained,

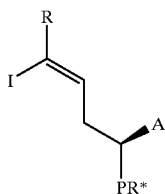

(XXIV)

wherein in the radicals have the meanings given for compounds of formula XXII, is then reacted with the above-described compound of formula XIII, wherein the radicals have the meanings given therein, whereby a compound of formula XXV is obtained,

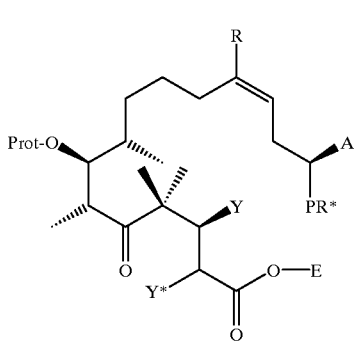

(XXV)

in which PR* has the meanings given for compounds of formula XXII and the remaining radicals have the meanings given for compounds of formula XII*. The reaction takes place analogously to that of the compound of formula XIII to form the compound of formula XII* (alkyl Suzuki coupling).

This is then followed by ester saponification to form a compound of formula XXVI,

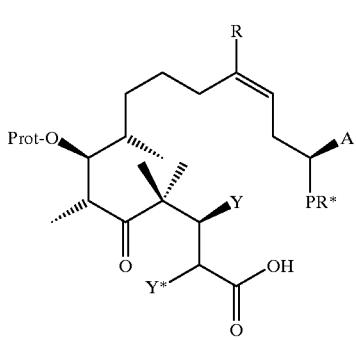

(XXVI)

wherein the radicals have the meanings given for compounds of formula XXV. The reaction takes place under analogous conditions to those for the reaction of compounds of formula XII* to form those of formula XII.

Finally, macro-lactamisation follows. In this, coupling reagents that are customary in peptide chemistry may be used, for example DCC/HOBt, HBTU, TPTU, HATU inter alia [see also under process a)].

In this process, (i) where PR* is a protected amino group, the protecting group must be already removed (in the case of tert-butoxycarbonyl e.g. with trifluoroacetic acid or HF/pyridine); alternatively, the N- and O-protecting groups may be removed simultaneously, or (ii) where PR* is N₃, the azide group must be reduced prior to macro-lactamisation, e.g. with triphenylphosphine or by catalytic hydrogenation.

In both cases, the corresponding compound of formula II is obtained, whereby according to (l), T*, NH or N(alkyl) is present, and according to (ii), NH is obtained.

Alternatively, the azidocarboxylic acid may be converted directly into the macrolactam through the action of triphenylphosphine at an elevated temperature.

Where present, hydroxy as Y in the above-mentioned compounds of formulae XII bis is preferably protected, for example as Prot-O, especially as tert-butyldimethylsilyloxy.

In compounds of formula II and their precursors, in which Z is present, —Z— is preferably a bond (forms a double bond together with the adjacent bond), Compounds of formula I, in which Z is O, are then obtained preferably from the corresponding compounds of formula II, in which —Z— is a bond.

In compounds of formula II, III, V, VI and/or VII, the bond indicated by a wavy line is understood to mean that the cis- or trans-form may exist, or a mixture thereof, the cis-form being preferred.

General Process Conditions

All process steps described here can be carried out under known reaction conditions, preferably under those specifically mentioned, in the absence of or usually in the presence of solvents or diluents, preferably those that are inert to the reagents used and able to dissolve them, in the absence or presence of catalysts, condensing agents or neutralising agents, for example ion exchangers, typically cation exchangers, for example in the H+ form, depending on the type of reaction and/or reactants at reduced, normal, or elevated temperature, for example in the range from –100° C. to about 190° C., preferably from about –80° C. to about 150° C., for example at –80 to 60° C., at room temperature, at –20 to 40° C. or at the boiling point of the solvent used, under atmospheric pressure or in a closed vessel, if required under pressure, and/or in an inert, for example an argon or nitrogen, atmosphere.

Salts may be present in all starting compounds and intermediates, if these contain salt-forming groups. Salts may also be present during the reaction of such compounds, provided that the reaction is not thereby disturbed.

At all reaction stages, isomeric mixtures that occur can be separated into their individual isomers, e.g. diastereoisomers or enantiomers, or into any mixtures of isomers,.e.g. racemates or diastereoisomeric mixtures, for example analogously to methods described under "Additional process steps".

In certain cases, typically in dehydrogenation or aldol reactions, it is possible to achieve stereoselective reactions, allowing for example easier recovery of individual isomers.

The solvents from which those can be selected which are suitable for the reaction In question include for example water, esters, such as lower alkyl-lower alkanoate, e.g ethyl acetate, ethers, such as aliphatic ethers, e.g. diethylether, or cyclic ethers, e.g. tetrahydrofuran, liquid aromatic hydrocarbons, such as benzene or toluene, alcohols, such as methanol, ethanol or 1- or 2-propanol, nitrites, such as acetonitrile, halogenated hydrocarbons, such as methylene chloride, acid amides, such as dimethylformamide, bases, such as heterocyclic nitrogen bases, e.g. pyridine, carboxylic acids, such as lower alkanecarboxylic acids, e.g. acetic acid, carboxylic acid anhydrides, such as lower alkane acid anhydrides, e.g. acetic anhydride, cyclic, linear, or branched hydrocarbons, such as cyclohexane, hexane, or isopentane, or mixtures of these solvents, e.g. aqueous solutions, unless otherwise stated in the description of the process. Such solvent mixtures may also be used in working up, for example by chromatography or partitioning.

The invention relates also to those embodiments of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention under the process conditions therein, and further processes the said compound in situ. In the preferred embodiment, one starts from those starting materials which lead to the compounds described hereinabove as preferred, particularly as especially preferred, primarily preferred, and/or preferred above all.

In particular, the invention also relates to intermediate products of formulae II, III, V, VI, VII, X and furthermore IX and XI, and also intermediate compounds of formulae XII*, XIII, XIV, XV, XVI and especially XXV and XXVI, wherein the radicals are respectively defined as mentioned, and especially have the preferred meanings for compounds of formula I; whereby instead of PG, if present, a free hydroxy group may also exist.

In the preferred embodiment, compounds of formula I are prepared analogously to the processes and process steps defined in the examples.

The compounds of formula I, including their salts, are also obtainable in the form of hydrates, or their crystals may include for example the solvent used for crystallisation (present as solvates).

Pharmaceutical Preparations, Methods, and Uses

The present invention relates also to pharmaceutical preparations that contain a compound of formula I as active ingredient and that can be used especially in the treatment of the diseases mentioned above. Preparations for enteral administration, such as nasal, buccal, rectal or, especially, oral administration, and for parenteral administration, such as intravenous, intramuscular or subcutaneous administration, to warm-blooded animals, especially humans, are especially preferred. The preparations contain the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical preparations for use in a method for the prophylactic or especially therapeutic treatment of the human or animal body, to a process for the preparation thereof (especially in the form of compositions for the treatment of tumours) and to a method of treating the above-mentioned diseases, primarily neoplastic diseases, especially those mentioned above.

The invention relates also to processes and to the use of compounds of formula I for the preparation of pharmaceutical preparations which contain compounds of formula I as active component (active ingredient).

Preference is given to a pharmaceutical composition that is suitable for administration to a warm-blooded animal, especially a human or commercially useful mammal, suffering from a disease that is responsive to the inhibition of microtubule depolymerisation, for example psoriasis or especially a neoplastic disease, comprising a correspondingly effective amount of a compound of formula I, or a pharmaceutically acceptable salt thereof when salt-forming groups are present, together with at least one pharmaceutically acceptable carrier.

A pharmaceutical composition for the prophylactic or especially therapeutic treatment of neoplastic and other proliferative diseases of a warm-blooded animal, especially a human or a commercially useful mammal requiring such treatment, especially suffering from such a disease, comprising a new compound of formula I, or a pharmaceutically acceptable salt thereof, as active ingredient in a quantity that is prophylactically or especially therapeutically active against said diseases, is likewise preferred.

Pharmaceutical preparations contain from about 0.000001% to 95% of the active ingredient, whereby single-dose forms of administration preferably have from approximately 0.00001% to 90% and multiple-dose forms of administration preferably have from approximately 0.0001 to 0.5% in the case of preparations for parenteral administration or 1% to 20% active ingredient in the case of preparations for enteral administration. Unit dose forms are, for example, coated and uncoated tablets, ampoules, vials, suppositories or capsules. Further dosage forms are, for example, ointments, creams, pastes, foams, tinctures, lipsticks, drops, sprays, dispersions, etc. Examples are capsules containing from about 0.0002 g to about 1.0 g active ingredient.

The pharmaceutical preparations of the present invention are prepared in a manner known per se, for example by means of conventional mixing, granulating, coating, dissolving or lyophilising processes.

Preference is given to the use of solutions of the active ingredient, and also suspensions or dispersions, especially isotonic aqueous solutions, dispersions or suspensions which, for example in the case of lyophilised preparations which contain the active ingredient on its own or together with a carrier, for example mannitol, can be made up before use. The pharmaceutical preparations may be sterilised and/or may contain excipients, for example preservatives, stabilisers, wetting agents and/or emulsifiers, solubilisers, salts for regulating the osmotic pressure and/or buffers and are prepared in a manner known per se, for example by means of conventional dissolving or lyophilising processes. The said solutions or suspensions may contain viscosity-increasing agents, typically sodium carboxymethylcellulose, carboxymethylcellulose, dextran, polyvinylpyrrolidone, or gelatin, or also solubilisers, for example ®Tween 80 [polyoxyethylene(20)sorbitan mono-oleate; trademark of ICI Americas, Inc, USA].

Suspensions in oil contain as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E; β-carotene or 3,5-di-tert-butyl-4-hydroxytoluene. The alcohol component of these fatty acid esters has a maximum of 6 carbon atoms and is a mono- or polyhydric, for example a mono-, di- or trihydric, alcohol, for example methanol, ethanol, propanol, butanol or pentanol or the isomers thereof, but especially glycol and glycerol. As fatty acid esters, therefore, the following are mentioned: ethyl oleate, isopropyl myristate, isopropyl palmitate, "Labrafil M 2375" (polyoxyethylene glycerol trioleate from Gattefossé, Paris), "Labrafil M 1944 CS" (unsaturated polyglycolised glycerides prepared by alcoholysis of apricot seed oil and consisting of glycerides and polyethylene glycol ester; Gattefossé, France), "Labrasol" (saturated polyglycolised glycerides prepared by alcoholysis of TCM and consisting of glycerides and polyethylene glycol ester; Gattefossé, France), and/or "Miglyol 812" (triglyceride of saturated fatty acids of chain length $C_8$ to $C_{12}$ from Hüls AG, Germany), but especially vegetable oils such as olive oil, cottonseed oil, almond oil, castor oil, sesame oil, soybean oil and more especially groundnut oil.

The manufacture of injectable preparations is usually carried out under sterile conditions, as is the filling, for example, into ampoules or vials, and the sealing of the containers.

Pharmaceutical compositions for oral administration can be obtained, for example, by combining the active ingredient with one or more solid carriers, if need be granulating a resulting mixture, and processing the mixture or granules, if desired, to form tablets or tablet cores, If need be by the inclusion of additional excipients.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, nice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores may be provided with suitable, if need be enteric, coatings, using inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Orally administrable pharmaceutical compositions also include hard capsules consisting of gelatin, and also soft, sealed capsules consisting of gelatin and a plasticiser, such as glycerol or sorbitol. The hard capsules may contain the active ingredient in the form of granules, for example in admixture with fillers, such as corn starch, binders, and/or glidants, such as talc or magnesium stearate, and if need be stabilisers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilisers and detergents, for example of the polyoxyethylene sorbitan fatty acid ester type, may also be added.

Suitable rectally administrable pharmaceutical preparations are, for example, suppositories that consist of a combination of the active ingredient and a suppository base. Suitable suppository bases are, for example, natural or synthetic triglycerides, paraffin hydrocarbons, polyethylene glycols or higher alkanols.

The formulations suitable for parenteral administration are primarily aqueous solutions ([or example in physiological saline, obtainable by diluting solutions in polyethylene glycol, such as polyethylene glycol (PEG) 300 or PEG 400] of an active ingredient in water-soluble form, e.g. a water-soluble salt, or aqueous injectable suspensions containing viscosity-increasing agents, e.g. sodium carboxymethyl cellulose, sorbitol and/or dextran, and where appropriate stabilisers. The active ingredient, if need be together with excipients, can also be in the form of a lyophilisate and can be made into a solution before parenteral administration by the addition of suitable solvents.

Solutions such as those used, for example, for parenteral administration can also be employed as infusion solutions.

Preferred preservatives are, for example, antioxidants, such as ascorbic acid, or microbicides, such as sorbic acid or benzoic acid.

The invention similarly relates to a process or a method for the treatment of one of the above-mentioned pathological conditions, especially a disease which responds to an inhibition of microtubule depolymerisation, especially a corresponding neoplastic disease. A compound of formula I can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a bodyweight of about 70 kg the dose administered is from approximately 0.1 mg to approximately 1 g, preferably from approximately 0.5 mg to approximately 200 mg, of a compound of the present invention. Administration is preferably effected e.g. every 1 to 4 weeks, for example weekly, every two weeks, every three weeks or every 4 weeks.

The present invention also relates in particular to the use of a compound of formula I, or a pharmaceutically acceptable salt thereof, especially a compound of formula I named as a preferred compound, or a pharmaceutically acceptable salt thereof, as such or in the form of a pharmaceutical formulation containing at least one pharmaceutically employable carrier, for the therapeutical and also prophylactic treatment of one or more of the above diseases.

The present invention also relates in particular to the use of a compound of formula I, or a pharmaceutically acceptable salt thereof, especially a compound of formula I named as a preferred compound, or a pharmaceutically acceptable salt thereof, for the preparation of a pharmaceutical formulation for the therapeutical and also prophylactic treatment of one or more of the above diseases.

The preferred dose quantity, composition, and preparation of pharmaceutical formulations (medicines) which are to be used in each case are described above.

The following examples illustrate the invention, but are not intended to restrict their scope in any way.

Temperatures are measured in degrees celsius. Unless otherwise indicated, the reactions take place at room temperature.

Abbreviations Used:

| | |
|---|---|
| DMF | N,N-dimethylformamide |
| DIBAL-H | diisobutyl aluminum hydride |
| DMSO | dimethyl sulphoxide |
| EA | ethyl acetate |
| ESI-MS | Electro-Spray Ionisation Mass Spectroscopy |
| ether | diethyl ether |
| FC | flash chromatography on silica gel (0.04–0.63 mm, Fluka, Buchs, Switzerland) |
| Fp | melting point |
| sat. | saturated |
| Hünig's base | ethyl diisopropylamine |
| NaHMDS | sodium hexamethyl disilazide |
| Ph | phenyl |
| RT | room temperature |
| tert | tertiary |
| TBS or TBDMS | tert-butyl-dimethylsilyl |
| THF | tetrahydrofuran |
| TMS | tetramethylsilane |
| aqu. | aqueous |

EXAMPLE 1

4,8-Dihydroxy-5,5,7,9,13-pentamethyl-16-(2-methyl-benzothiazol-5-yl)-oxacyclohexadec-13-en-2,6-dione (19)

formula:

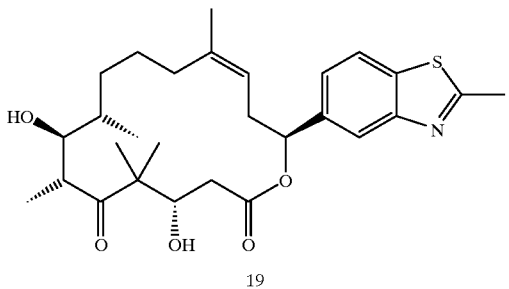

19

0.175 ml of trifluoroacetic acid are added dropwise over the course of 5 minutes at −20° C. to a solution of 0.041 g of the protected lactone 18 [see example (1k)] in 0.7 ml of CH$_2$Cl$_2$, and the solution is subsequently stirred for 1 hour at 0° C. The solution is then concentrated by evaporation, and the residue obtained is purified by FC in CH$_2$Cl$_2$/methanol 100/1→100/2. 0.028 g of 19 are obtained as a colourless resin.

ESI-MS: 502 (M+H)$^+$ $^1$H-NMR (CDCl$_3$, 300 MHz), δ (ppm vs. TMS): 7.99 (s, 1H); 7.80 (d, 1H); 7.36 (d, 1H); 5.92 (d,d, 1H); 5.15–5.26 (m, 1H); 4.21 (d,d, 1H); 3.75 (t, 1H); 3.1–3.23 (m, 1H); 2.84 (s, 3H); 1.70 (s, ~3H). [α]$_D$=−77.39° (c=0.115 in CHCl$_3$).

The starting materials are produced as follows:

(1a) Aldehyde 1

Formula:

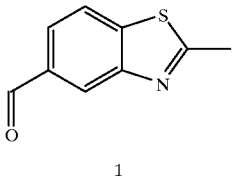

1

21.09 of N-bromosuccinimide are added to a solution of 16.07 g of 2.5-dimethylbenzo-thiazole (Fluka, Buchs, Switzerland) in 100 ml of carbon tetrachloride, and the suspension is then irradiated with a tungsten lamp and heated for 4 hours to 80°. After cooling the reaction mixture to room temperature, undissolved components are filtered off and the solvent is evaporated. The oil thus obtained is mixed with, in succession, 200 ml of 50% aqueous acetic acid and 26.8 g of hexamethylene tetramine, the mixture is subsequently heated for 80 minutes to 110° and the reaction is then stopped by adding 250 ml of water. The reaction mixture is worked up by extracting with ethyl acetate; the combined organic extracts are then back-extracted with, in succession, saturated aqueous NaHCO$_3$ solution, water and saturated aqueous NaCl solution, and finally dried over Na$_2$SO$_4$. The oil obtained after concentrating the solution by evaporation is purified by FC in hexane/EA 3/1. The crystals obtained are recrystallised from tert-butylmethylether/hexane. Compound 1 is thus obtained: M.p. 98–100° C. ESI-MS: 178 (M+H). $^1$H-NMR (CDCl$_3$, 300 MHz), δ (ppm vs. TMS): 10.11 (s, 1H); 8.39 (d, 1H); 7.95 (, 1H); 7.92 (dd, 1H); 2.88 (s, 3H).

(1b) Alcohol 2

Formula:

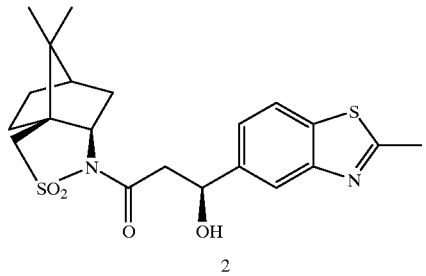

2

3.75 ml of trifluoromethanesulphonic acid are added dropwise over the course of 5 minutes at 20° C. to a solution of 6.2 ml of triethylborane in 42.5 ml of hexane, and the solution is subsequently stirred for 30 minutes at room temperature and then for a further 15 minutes at 40° C. After cooling to room temperature, 8.5 ml of CH$_2$Cl$_2$ are added, and stirring continues for 45 minutes at room temperature. Then, first of all, at 0° C. a solution of 8.4 g of (2R)-acetylbornane-10,2-sultam [see Tetrahedron Lett. 33, 2439 (1992)] in 12 ml CH$_2$Cl$_2$ is added dropwise over 45 minutes, and then at −4° C. to −2° C., a solution of 7.3 ml of Hunig's base in 7.2 ml of CH$_2$Cl$_2$ is added dropwise over 15 minutes. The reaction mixture is then cooled to −78° C., and at this temperature, a solution of 8.1 9 of 1 in 30 ml of CH$_2$Cl$_2$ is added dropwise over 30 minutes. Stirring is subsequently effected for 3 hours at −78° C. and the reaction is then stopped by adding 85 ml of saturated aqueous NH$_4$Cl solution. After heating to room temperature, the organic phase is separated, the aqueous phase then extracted with CH$_2$Cl$_2$ and the combined organic extracts dried over Na$_2$SO$_4$. The oil obtained after evaporating the solvent is purified by FC in CH$_2$Cl$_2$/ether. By subsequent crystallisation from ether, the desired diastereoisomer 2 is obtained, and also a batch of a mixture of 2 and its R-diastereoisomer. This mixture undergoes further FC in ether, which yields a further amount of 2.

Fp. 158–160° C. ESI-MS: 435 (M+H). $^1$H-NMR (CDCl$_3$, 500 MHz), δ (ppm vs. TMS): 7.87; (m, 2H); 7.37 (dd, 1H); 5.23 (t, 1H); 5.10 (d, 1H); 3.79 (t, 1H); 3.62 (d, 1H); 3.53 (d, 1H); 3.14 (dd, 1H): 2.96 (dd, 1H); 2.77 (s, 3H); 0.91 (s, 3H); 0.87 (s, 3H).

(1c) TBS-ether 3

Formula:

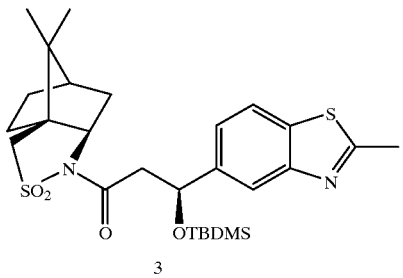

3

A solution of 7.46 g of 3 in 75 ml of DMF is mixed with 1.76 g of imidazole and 3.11 g of TBS-Cl and the mixture is stirred first of all for 30 minutes at room temperature and then for 22 hours at 35° C. Then, a further 0.6 g of imidazole and 1.06 g of TBS-Cl are added, and after a further 4 hours at 35° C., 1.17 g of imidazole and 2.04 g of TBS-Cl are added, After another 4 hours At 35° C. the reaction mixture is allowed to cool to room temperature and the solvent is evaporated. The oil thus obtained is taken up in 300 ml of CH$_2$Cl$_2$, the solution washed with water, dried over Na$_2$SO$_4$ and finally the CH$_2$Cl$_2$ is drawn off. The resulting oil is purified by FC in ether/hexane 2/1. One thereby obtains 3 as white crystals and an oil. Further FC of this oil in the same eluent system yields an additional quantity of 3 (also as white crystals). M.p. 123–126° C. ESI-MS: 549 (M+H). $^1$H-NMR (CDCl$_3$, 200 MHz), δ (ppm vs. TMS): 7.88 (d, 1H); 7.72 (d, 1H); 7.40 (dd, 1H); 5.34 (t, 1H); 3.76 (m, 1H); 3.46 (q, 1H); 3.14 (d, 2H); 2.8 (s, 3H); 0.84 (s, 3H); 0.83 (s, 9H); 0.65 (s, 3H); 0.04 (s, 3H); −0.20 s, 3H).

(4) Aldehyde 4

Formula:

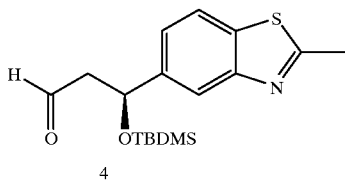

4

A 1 M solution of DIBAL-H in CH$_2$Cl$_2$ is added dropwise at −78° C. under nitrogen, over 15 minutes, to a solution of 7.97 g of 2 in 100 ml of CH$_2$Cl$_2$. The reaction mixture is then stirred for 2½ hours at −78° C., whereby after 2 hours a further 3 ml of the above DIBAL-H is added, and the reaction is then stopped by adding 6 ml of methanol. Thereafter, 100 ml of CH$_2$Cl$_2$ and 50 ml of water are added, and filtration then takes place over Celite (=®Celite, filtering assistant based on diatomaceous earth, Celite Corp.; obtainable from Fluka, Buchs, Switzerland). The organic phase is separated, washed with water, dried over Na$_2$SO$_4$, and the solvent evaporated. The oil thus obtained is purified by FC twice in hexane/ether. 4 is obtained as an oil. ESI-MS: 368 (M+H+MeOH). $^1$H-NMR (CDCl$_3$, 200 MHz), δ (ppm vs. TMS): 9.80 (d, 1H); 7.90 (d, 1H); 7.77 (d, 1H); 7.33 (dd, 1H); 5.35 (m, 1H); 2.82 (s, 3H); 0.85 (s, 9H); 0.05 (s, 3H); −0.15 (s, 3H).

(1e) Vinyl iodide 5

Formula:

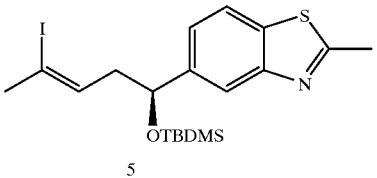

5

6 ml of a 1M solution of NaHMDS in THF are added dropwise under nitrogen, over 5 minutes, to a suspension of [Ph$_3$P-CHlCH$_3$]$^{+/-}$ cooled to −70° C. The orange-coloured suspension is stirred first of all for 15 minutes at −70° C. and then for 70 minutes at −40° C., which leads to the formation of an orange-brown solution. The mixture is then cooled again to −70° C., and at this temperature, a solution of the aldehyde 4 in 8 ml of THF is added dropwise over 10 minutes. Stirring is subsequently effected for 50 minutes at −70° C. and the reaction is then stopped by adding saturated aqueous NH4Cl solution. After dilution with 100 ml of ether and 40 ml of water, first of all filtration takes place, then the organic phase is separated, washed with water and dried over Na$_2$SO$_4$ and then the solvent is evaporated. The resulting oil is purified by FC in hexane/EA 9/1. 5 is obtained as an oil. ESI-MS: 474 (M+H). $^1$H-NMR (CDCl$_3$, 200 MHz), δ (ppm vs. TMS): 7.89 (d, 1H); 7.75 (d, 1H); 7.35 (dd, 1H); 5.23 (t, 1H); 5.45 (t, 1H); 4.87 (t, 1H); 2.83 (s, 3H); 0.88 (s, 9H); 0.04 (s, 3H); −0.12 (s, 3H)

Preparation of the 1-iodo-ethyl-phosphonium iodide [Phe$_3$P-CH(l)CH$_3$]$^+$ I$^-$ is effected by adding a 1.6 M solution of n-butyllithium in hexane dropwise to a solution of an equimolar amount of ethylphosphonium iodide (Aldrich) in THF at −78° C. and filtering the precipitate that forms. Recrystallisation from dichloromethane/THF gives 1-iodo-ethylphosphonium iodide as a yellow crystalline solid which is stable in the presence of air ($^1$H-NMR (DMSO-d$_6$: δ=8.1–7.7 m(15H); 6.3 m (1H); 2.55 dd (3H)).

(1f) Olefin 12

Formula:

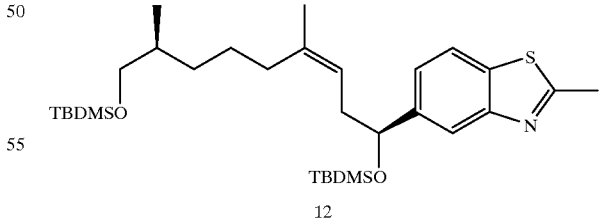

12

0.038 ml of ethylene bromide are added under nitrogen to a suspension of 0.509 g of Zn/Cu pair [Organic Synthesis 41, 72 (1966)] in benzene, and the mixture is heated to 90° C. for 30 seconds. After cooling to room temperature, 0.0375 ml of trimethylsilyl chloride are added, and stirring continues for 5 minutes at room temperature. After adding a mixture of 1.732 g of the alkyl iodide 28, for formula see below [Schinzer et al., Synlett. 1998, 861–4], 0.8 ml of dimethylacetamide and 4.3 ml of benzene, the reaction mixture is heated first of all for 2 hours 45 mins. at 60° C. and, after subsequently. adding 0.0215 ml of trimethylsilyl triflate and a further 0.8 ml of dimethylacetamide, for 1 hour at 70° C. After cooling to room temperature, first of all 0.1498 g of tetrakis(triphenylphosphine)-Pd are added, and then after stirring for 5 minutes, 1.59 g of the vinyl iodide 5 and 3 ml of benzene are added. The reaction mixture is heated for 30 minutes to 60° C., and after cooling to room temperature, 5.5 ml of saturated aqueous $NH_4Cl$ solution are added. After stirring for 5 minutes, 32 ml of tert-butylmethylether are added and the organic phase is separated and dried over $Na_2SO_4$.

The oil remaining after filtration and evaporation of the solvent is purified by FC twice, the first time with hexane/tert-butylmethylether 95/5 and the second time with hexane/EA 200/3. 12 is obtained as an oil. ESI-MS: 563 (M+H). $^1$H-NMR (CDCl$_3$, 200 MHz), δ (ppm vs. TMS): 7.85 (d, 1H); 7.73 (d, 1H); 7.32 (dd, 1H); 5.12 (t, 1H); 4.63 (t, 1H); 3.35 (m, 2H); 2.82 (s, 3H); 2.38 (m, 2H); 1.90 (t, 2H); 1.63 (s, 3H); 0.87 (s, 18H); 0.02 (s, 9H); −0.27 (s,3H).

(1g) Alcohol 13

Formula:

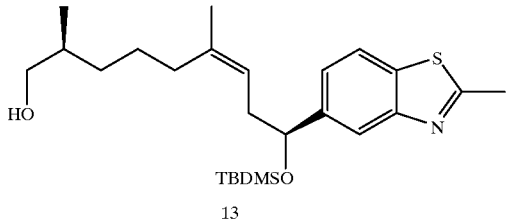

13

0.540 g of camphorsulphonic acid are added at 0° C. to a solution of 1.304 g of 12 in 40 ml of $CH_2Cl_2$/methanol 1/1, and the mixture is stirred first of all for 30 minutes at 0° C. and then for 100 minutes at room temperature. The reaction is then stopped by adding 2 ml of a saturated aqueous NaHCO$_3$ solution, and after a further 5 minutes is concentrated by evaporation. The oil thus obtained is taken up in $CH_2Cl_2$, and the solution is washed with water, dried over $Na_2SO_4$ and then concentrated by evaporation. The remaining oil is purified by FC in hexane/EA 3/1. 13 is obtained as an oil. ESI-MS: 448 (M+H). $^1$H-NMR (CDCl$_3$, 200 MHz), δ (ppm vs. TMS): 7.85 (d, 1H); 7.74 (d, 1H); 7.32 (dd, 1H); 5.15 (t, 1H); 4.74 (dt, 1H); 3.40 (t, 2H); 2.82 (s, 3H); 2.39 g (q, 2H); 1.90 (dt, 2H); 1.62 (s, 3H); 0.87 (s, 9H); 0.83 (s, 9H); 0.02 (s, 3H); −0.12 (s, 3H).

(1 h) Aldehyde 14

Formula:

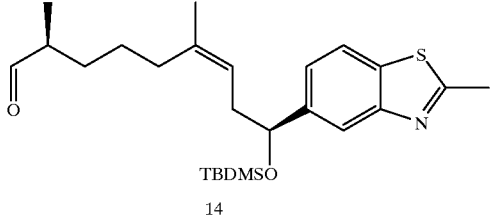

14

0.310 ml of DMSO are added to a solution of 0.172 ml of oxalyl chloride in 5 ml of $CH_2Cl_2$, which has been cooled to −78° C., and the solution is stirred for 10 minutes at −78° C. Subsequently, over 15 minutes, a solution of 0.813 g of 13 in 3 ml of $CH_2Cl_2$ is added In such a way that the temperature does not exceed −70° C. After stirring for 30 minutes at −78° C., 1.26 ml of triethylamine are added, and the solution is allowed to warm to room temperature over 45 minutes. After 2 hours at room temperature, 5 ml of water are added, the organic phase is separated and the aqueous phase is extracted 3 times with $CH_2Cl_2$. The oil remaining after drying the combined organic extracts over $Na_2SO_4$ and evaporating the solvent is purified by FC in hexane/EA 1/19→1/4. 14 is obtained as an oil. ESI-MS: 446 (M+H)$^+$. $^1$H-NMR (CDCl$_3$, 200 MHz), δ (ppm vs. TMS): 9.52 (s, 1H); 7.85 (d, 1H); 7.73 (d, 1H); 7.31 (d,d, 1H); 5.18 (t, 1H); 4.74 (t, 1H); 2.81 (s, 3H); 1.62 (s, 3H); 1.01 (d, 3H); 0.87 (s, 9H); 0.01 (s, 3H); −0.13 (s, 3H). [α]$_D$=+45.76° (c=0.295 in CHCl$_3$).

(11) Carboxylic acid 16

Formula:

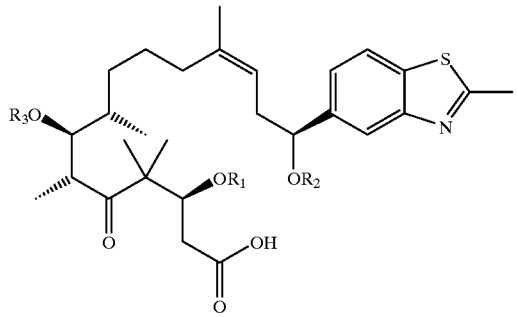

16

$R_1 = R_2 = R_3$ = TBDMS 3.41 ml of a 1.6 M solution of n-butyllithium in THF is added dropwise at 0° C. over 15 minutes to a solution of 0.771 ml of N,N-diisopropyl-ethylamine in 6 ml of THF. The solution is stirred for 10 minutes at −4° C./−5° C. and then cooled to −78° C. At this temperature, a solution of 0.660 g of the carboxylic acid 29 g is added, the solution is then allowed to warm to −40° C. for 15 minutes, and is subsequently cooled again to −78° C. 3 ml of a solution of 0.608 g of aldehyde 14 in THF are subsequently added and the solution is stirred for 30 minutes at −78° C. The reaction is stopped by adding 7 ml of saturated aqueous $NH_4Cl$ solution and, after heating to room temperature, the solution is mixed with 0.513 ml of acetic acid and extracted with EA. The combined organic extracts are dried over $Na_2SO_4$, the solvent evaporated, and the remaining oily residue purified by FC in toluene/EA 1/1. The aldol product 15 thus obtained (see below for formula) is dissolved in 40 ml of $CH_2Cl_2$ and the solution mixed with 0.435 ml of 2,6-lutidine. After cooling to 0° C., 0.720 ml of TBS triflate are added and the mixture is stirred for 2½ hours at 0° C. After adding 8 ml of 20% citric acid, the organic phase is separated, the aqueous solution back-extracted with $CH_2Cl_2$, dried over $Na_2SO_4$ and the solvent evaporated. The remaining oil is taken up in 20 ml of methanol, the solution mixed with 2.0 g of $K_2CO_3$ and 1 ml of water, and the mixture stirred for 90 minutes at room temperature. Undissolved constituents are then filtered off, the pH value of the filtrate is adjusted to 4.5 with Dowex 50W×8 ion exchanger resin (very acidic cation exchanger with sulphonic acid groups as the active group, matrix of styrene with 8% DVB as crosslinker, Dowex® is a Trademark of Dow Chemical Co.), the resin is filtered off and the new filtrate concentrated by evaporation. The residue is partitioned between 20 ml of $CH_2Cl_2$ and 20 ml of saturated aqueous $NH_4Cl$ solution, the organic phase is separated, the aqueous solution back-extracted with CH₂Cl₂ and the combined organic extracts are dried over Na₂SO₄ and concentrated by evaporation. The oil thus obtained is purified by FC in CH₂Cl₂/MeOH 99/1→99/2, but can only be obtained in a form which is contaminated with carboxylic acid 29. This material undergoes the above-described silylation/desilylation sequence a second time. Finally, pure 16 is obtained as an oil. ESI-MS: 862,4 (M+H).

Formula of 29:

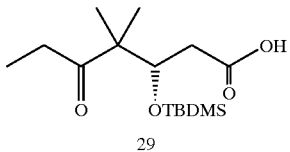

29

(see J. Am. Chem. Soc. 119, 7974 (1997); Synlett 1997, 824 (incl. Corrigendum in Synlett 1998, 328)

Formula of aldol product 15:

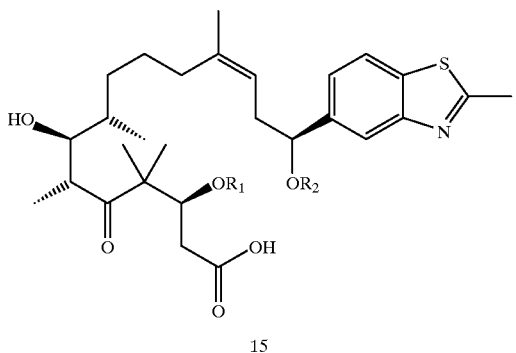

15

R₁ = R₂ = TBDMS (1j) Hydroxy acid 17

Formula:

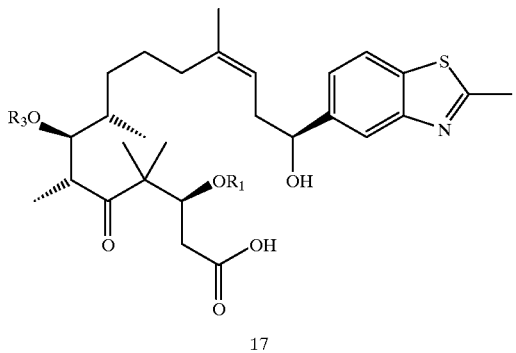

17

R₁ = R₃ = TBDMS 1.85 ml of a 1 M solution of tetrabutylammonium fluoride are added to a solution of 0.265 g of 16 in 6 ml of THF, and stirred for 6 hours at room temperature. Subsequently, 8 ml of EA and 7 ml of 20% citric acid are added, the organic phase is separated and the aqueous solution back-extracted with EA. The oily residue obtained after drying the combined organic extracts over Na₂SO₄ and evaporating the solvent is purified by FC in CH₂Cl₂/methanol 98/2→97/3. 17 is obtained as an oil.

ESI-MS: 748.3 (M+H)⁺. ¹H-NMR (CDCl₃, 200 MHz), δ (ppm vs. TMS): 8.23 (d, 1H); 7.76 (d, 1H); 7.76 (d, 1H); 7.40 (d,d, 1H); 5.24 (t, 1H); 4.73–4.84 (m, 1H); 4.45 (t, 1H); 3.67–3.74 (m, 1H); 3.10–3.22 (m, 1H); 2.82 (s, 3H); 1.75 (s, 3H); 1.14 (d, 3H); 1.08 (d, 3H); 0.80–0.95 (m, ca. 24H); 0.10 (s, 3H); 0.05 (s, 3H); 0.04 (s, 3H); 0.01 (s, 3H).

(1k) Protected lactone 18

Formula:

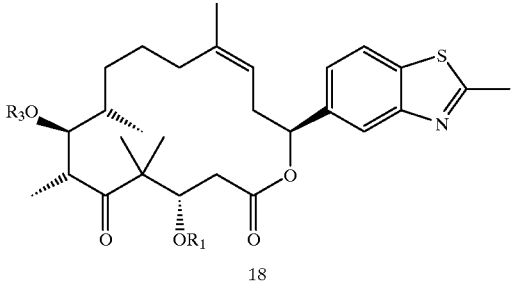

18

R₁ = R₃ = TBDMS 0.0866 ml of triethylamine and 0.0677 ml of 2,4,6-trichlorobenzoyl chloride (Aldrich, Buchs, Switzerland) are added to a solution of 0.216 g of hydroxy acid 17 in 3 ml of THF, which has been cooled to 0° C., and they are stirred for 1 hour at 0° C. The solution is subsequently added dropwise at room temperature, over 5 minutes, to a solution of 0.354 g of N,N-dimethyl-aminopyridine in toluene and then stirred for 15 hours at room temperature. The solid residue obtained after concentrating the suspension by evaporation at 35° C. is suspended in 30 ml of hexane/ether 3/2 and filtered and the residue of filtration is washed twice, each time with 15 ml of this solvent mixture. The whole filtrate is evaporated to dryness and the solid residue is purified by FC twice in toluene/acetone 100/1.25→100/5 or 100/1→100/4. 18 is obtained as a colourless resin.

ESI-MS; 730 (M+H)⁺. ¹H-NMR (CDCl₃, 200 MHz), δ (ppm vs. TMS); 7.97 (s, 1H); 7.79 g (d, 1H); 7.37 (d, 1H); 5.59 g (d, 1H); 5.25 (t, 1H); 3.93–4.0 (m, 1H); 3.90 (d, 1H); 2.85 (s, 3H); 1.71 (s, 3H). [α]_D=−60.72° (c=0.415 in CHCl₃).

EXAMPLE 2

4,8-dihydroxy-5,5,7,9,13-pentamethyl-16-(2-methyl-benzothiazol-6-yl)-oxacyclohexadec-13-en-2,6-dione (deprotected lactone 27)

Formula:

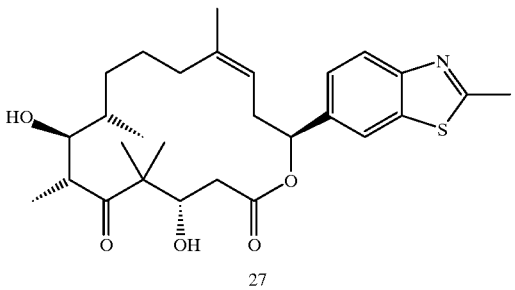

27 preparation of 27 takes place analogously to that of 19 g (example 1) from 0.144 g of 26 [example 2(m)].

ESI-MS: 502 (M+H)⁺. ¹H-NMR (CDCl₃, 200 MHz), δ (ppm vs. TMS): 7.92 (d, 1H); 7.83 (d, 1H); 7.44 (d,d, 1H); 5.86 (d,d, 1H); 5.14–5.25 (m, 1H); 4.08 (d,d, 1H); 3.74 (t, 1H); 3.16 (m, 1H); 2.82 (s, 3H); 1.67 (s, ~3H); 1.26 (s, 3H);

1.19 g (d, 3H); 1.03 (s) and 1.01 (s, together 6H). [α]$_D$=−63,75° (c=0.4 in CHCl$_3$).

The starting materials are produced as follows:

(2a) 2-bromo-4-methyl-thioacetanilide

Formula:

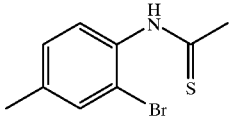

2-bromo-4-methyl-acetanilide (Maybridge) is added to a suspension of 24.74 g of P$_2$S$_5$ in 250 ml of benzene and heated under reflux for 3 hours. After cooling to room temperature, the mixture is filtered and the residue of filtration washed with ether. The combined filtrates are extracted with 10% aqueous Na$_2$CO$_3$ solution and the aqueous extract is subsequently acidified to pH 1 with conc. HCl. The resulting precipitate is filtered and recrystallised from ether/hexane. 2-bromo-4-methyl-thioacetanilide is obtained as brown crystals. ESI-MS: 244/246 (M+H). $^1$H-NMR (CDCl$_3$, 200 MHz), δ (ppm vs. TMS): Rotamer mixture in a ratio of ca. 3:1. 9.00 (s, 1/3×1H); 8.63 (s, 2/3×1H); 8.15 (d, 1H); 7.49 g (s, 1/3×1H); 7.42 (s, 2/3×1H); 7.18 (s, 1/3×1H): 7.12 (s, 2/3×1H): 2.77 (s, 3H); 2.40 (s, 1/3×3H); 2.23 (s, 2/3×1H).

(2b) Benzothiazole 6 (see Spitulnik, M. J., Synthesis 1976, 730–1)

Formula:

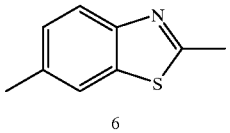

3.05 g of a 55% dispersion of NaH in oil is added in portions, under nitrogen, to a solution of 14.27 g of 20 in 72 ml of N-methyl-2-pyrrolidone in such a way that the temperature does not exceed 25° C., and the mixture is subsequently heated for 2 hours to 150° C. After cooling to room temperature, water is added and the mixture extracted with ether. The oil obtained after drying the organic phase and concentrating by evaporation is purified by FC in hexane/ether 4/1. 6 is obtained as a brown oil. ESI-MS: 164 (M+H). $^1$H-NMR (CDCl$_3$, 200 MHz), δ (ppm vs. TMS): 7,81 (d, 1H); 7,59 g (d, 1H); 7,22 (dd, 1H); 2,79 g (s, 3H); 2.46 (s, 3H).

(2c) Aldehyde 7

Formula:

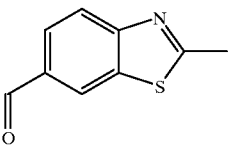

The preparation of 7 takes place analogously to that of 1 [example (1 a)] from 15.08 g of 6. M.p. 78–80° C. ESI-MS: 178 (M+H). $^1$H-NMR (CDCl$_3$, 200 MHz), δ (ppm vs. TMS): 10.08 (s, 1H); 8.38 (d, 1H); 8.06 (d, 1H); 7.96 (dd, 1H); 2.90 (s, 3H).

(2d) Alcohol 8

Formula:

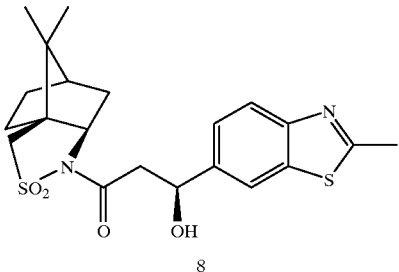

The preparation of 8 (oil) takes place analogously to that of 2 [example (1b)] from 9.03 g of 7.

ESI-MS: 435 (M+H). $^1$H-NMR (CDCl$_3$, 200 MHz), δ (ppm vs. TMS): 7.89 g (m, 2H), 7.43 (dd, 1H); 5.31 (m, 1H); 5.10 (d, 1H); 3.89 g (t, 1H); 3.51 (d, 1H); 3.45 (m, 2H); 3.45 (d, 1H); 3.16; (m, 2H); 2.72 (s, 3H); 1.07 (s, 3H); 0.95 (s, 3H).

(2e) TBS-ether 9

Formula:

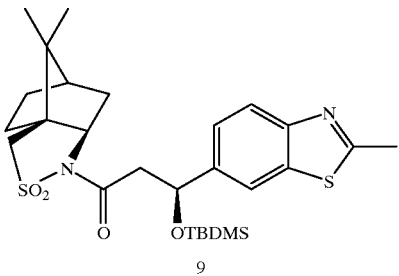

The preparation of 9 (oil) takes place analogously to that of 3 [example (1c)] from 9.03 g of 8.

M.p. 208–212° C. ESI-MS; 549 (M+H). $^1$H-NMR (CDCl$_3$, 200 MHz), δ (ppm vs. TMS): 7.85; (d, 1H); 7.81 (d, 1H); 7.41 (dd, 1H); 5.21 (t, 1H); 3.77 (m, 1H); 3.37 (s, 2H); 3.13 (m, 2H); 2.81 (s, 3H); 0.83 (s, 9H); 0.82 (s, 3H); 0.58 (s, 3H); 0.05 (s, 3H); −0.18 (s, 3H).

(2f) Aldehyde 10

Formula:

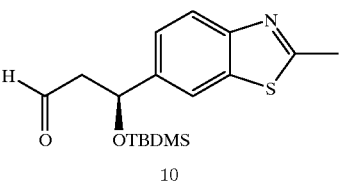

The preparation of 10 (oil) takes place analogously to that of 4 [example (1d)] from 9.11 g of 9. ESI-MS: 368 (M+H+MeOH). $^1$H-NMR (CDCl$_3$, 200 MHz), δ (ppm vs. TMS): 9.80 (d,1H); 7.91 (d, 1H); 7.81 (d, 1H); 7.40 (dd, 1H); 5.32 (m, 1H); 2.83 (s, 3H); 0.85 (s, 3H); −0.15 (s, 3H).

(2g) Vinyl iodide 11

Formula:

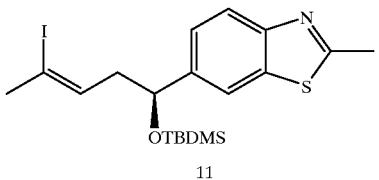

11

The preparation of 11 (oil) takes place analogously to that of 5 [example (1e)] from 4.64 g of 10. ESI-MS: 474 (M+H). ¹HNMR (CDCl$_3$, 200 MHz), δ (ppm vs. TMS): 7.87 (d, 1H); 7.78 (d, 1H); 7.39 g (dd, 1H); 5.45 (dt, 1H); 4.85 (dt, 1H); 2.82 (s, 3H); 0.88 (s, 9H); 0.03 (s, 3H); −0.12 (s, 3H).

(2h) Olefin 20

Formula:

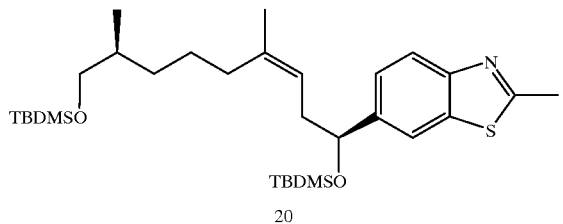

20

The preparation of 20 (oil) takes place analogously to that of 12 [example (1f)] from 3.54 g of 11. and 3.83 g of the alkyl iodide 28. ESI-MS: 563 (M+H). ¹H-NMR (CDCl$_3$, 200 MHz), δ (ppm vs. TMS): 7.84 (d, 1H); 7.73 (d, 1H); 7.35 (dd, 1H); 5.12 (dt, 1H); 4.70 (dt, 1H); 2.81 (s, 3H); 1.63 (s, 3H); 0.87 (s, 18H); 0.02 (s, 3H); 0.01 (s, 6H); −0.13 (s, 3H).

(2i) Alcohol 21

Formula:

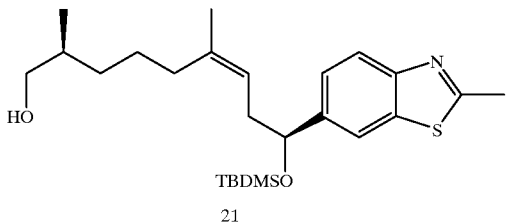

21

The preparation of 21 (oil) takes place analogously to that of 13 [example (1g)] from 3.64 g of 20. ESI-MS: 448 (M+H). ¹H-NMR (CDCl$_3$, 200 MHz), δ (ppm vs. TMS): 7.85 (d, 1H); 7.72 (d, 1H); 7.35 (dd, 1H); 5.14 (dt, 1H); 4.70 (t, 1H); 3.38 (t, 2H); 2.82 (s, 3H); 2.27 (q, 2H); 1.86 (dt, 2H); 1.63 (s, 3H); 0.86 (s, 9H); 0.02 (s, 3H); −0.13 (s, 3H).

(2j) Aldehyde 22

Formula:

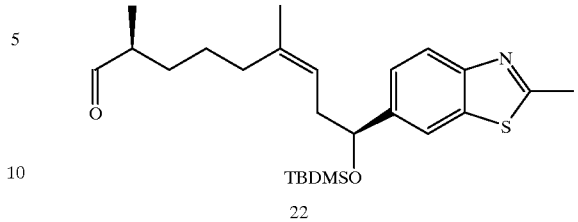

22

The preparation of 22 takes place analogously to that of 14 [example (1 h)] from 2.26 g of 21.

ESI-MS: 446 (M+H)⁺. ¹H-NMR (CDCl$_3$, 200 MHz), δ (ppm vs. TMS): 9.54 (s, 1H); 7.86 (d, 1H); 7.74 (d, 1H); 7.35 (d,d, 1H); 5.16 (t, 1H); 4.71 (t, 1H); 2.81 (s, 3H); 1.63 (s, 3H); 1.02 (d, 3H); 0.88 (s, 9H); 0.01 (s, 3H); −0.13 (s, 3H). [α]$_D$=−47.47° (c=0,99 in CHCl$_3$)

(2k) Carboxylic acid 24

Formula:

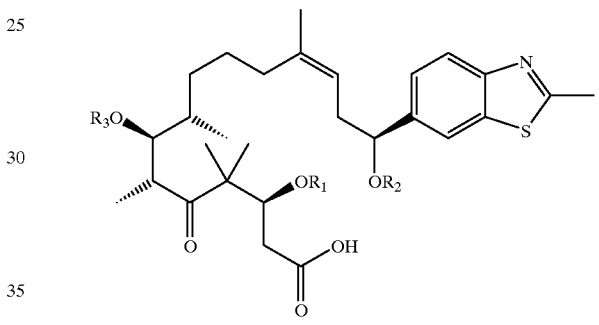

24

R$_1$ = R$_2$ = R$_3$ = TBDMS

The preparation of 24 takes place analogously to that of 16 [example (1i)] from 1.82 g of 22 and 1.98 g of carboxylic acid 29 (via the aldol product 23).

ESI-MS: 862 (M+H)⁺. ¹H-NMR (CDCl$_3$, 200 MHz), δ (ppm vs. TMS): 7.85 (d, 1H); 7.73 (d, 1H); 7.36 (d,d, 1H); 5.14 (t, 1H), 4.70 (t, 1H); 4.32–4.40 (m, 1H); 3.70–3.78 (m, 1H); 3.09 (t, 1H); 2.81 (s, 3H); 1.62 (s, 3H); 0.88 (2s, ca. 27H); 0.01–0.08 (m, 15H); −0.12 (s, 3H). [α]$_D$=+58.3° (c=0,3 in CHCl$_3$).

Formula of aldol product 23:

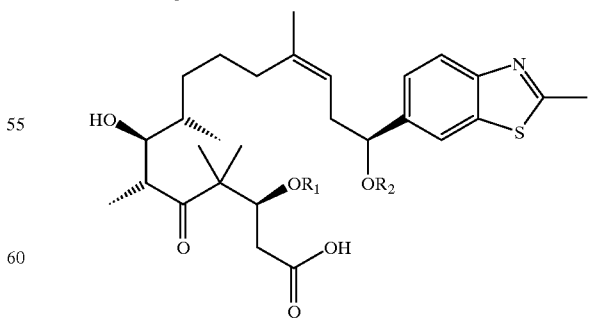

23

R$_1$ = R$_2$ = TBDMS

(21) Hydroxy acid 25

Formula:

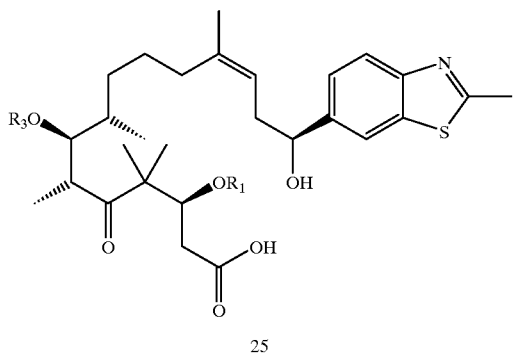

25

R₁ = R₃ = TBDMS

The preparation of 25 takes place analogously to that of 17 [example (1j)] from 1.314 g of 24.
ESI-MS: 748 (M+H)⁺. ¹H-NMR (CDCl₃, 200 MHz), δ (ppm vs. TMS): 7.79 g (d, 1H); 7.73 (d, 1H); 7.41 (d,d, 1H); 5.14 (t, 1H); 4.78 (d,d, 1H); 4.37 (d.d, 1H); 3.76 (broad d, 1H); 3.10 (t, 1H); 2.82 (s, 3H); 1.69 g (s, 3H); 0.88 (s); 0.86 (s); 0.08 (s, 3H); 0.03 (s, 9H). [α]$_D$=−162.95° (c=0,305 in CHCl₃).

(2m) Protected lactone 26

Formula:

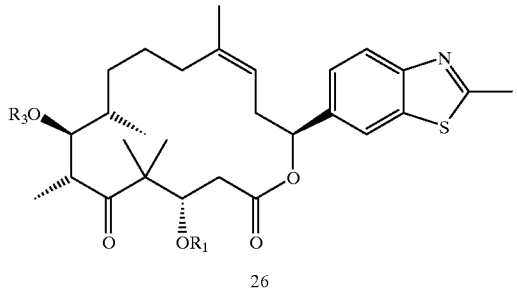

26

R₁ = R₃ = TBDMS

The preparation of 26 takes place analogously to that of 18 from 0.850 g of 25. [α]$_D$=−41.19° (c=0.415 in CHCl₃). ESI-MS: 730 (M+H)⁺. ¹H-NMR (CDCl₃, 300 MHz), δ (ppm vs. TMS): 7.93 (d, 1H); 7.85 (s, 1H); 7.48 (d, 1H); 5.59 g (d, 1H); 5.22 (t, 1H); 3.93–4.02 (m, 1H); 3.92 (d, 1H); 2.83 (s, 3H): 1.71 (s, 3H). [α]$_D$=−41.19° (c=0.415 in CHCl₃).

The following examples 3 and 4 are obtained from compounds 19 and 27 by epoxidation in accordance with the following process:

Variant A: Lactone 19 (10 mg) or compound 27 (10 mg) is taken up in 0.5 ml of methylene chloride, and at a low temperature (approximately −10° C.) 1.1 to 1.2 equivalents of metachloroperbenzoic acid (Fluka, degree of purity 90%) are added. The reaction mixture is stirred for 2 hours at −10° C. and subsequently diluted with ethyl acetate and washed with saturated aqueous. NaHCO₃ solution. The residue obtained after drying the organic phase with MgSO₄ and concentrating by evaporation (crude end product 19a or 27a) is then purified by FC in CH₂Cl₂/MeOH 100/2.

Variant B: A solution of dimethyldioxirane in acetone is added dropwise at −50° C. to a solution of 10 mg of lactone 19 or lactone 27, until the starting material can no longer be detected by thin-layer chromatography. Working up analogously to variant A yields the end products:

Variant C: The reaction is carried in analogy to that described below for the preparation of compound 72.

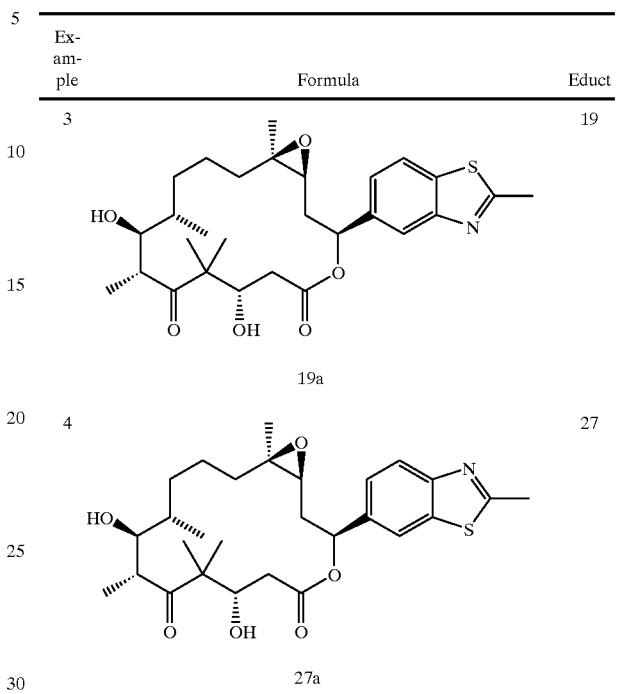

| Example | Formula | Educt |
|---|---|---|
| 3 | 19a | 19 |
| 4 | 27a | 27 |

The systematic name of compound 19 a is 7,11-dihydroxy-8,8,10,12,16-pentamethyl-3-(2-benzothiazol-5-yl)-4,17-dioxa-bicyclo[4.1.0]heptadecan-5,9-dione, and that of compound 27 a is 7,11-dihydroxy-8,8,10,12,16-pentamethyl-3-(2-methyl-benzothiazol-6-yl)-4,17-dioxa-bicyclo[14.1.0]heptadecan-5,9-dione.

EXAMPLES 1/3 ALTERNATIVE ROUTE

Compound 30

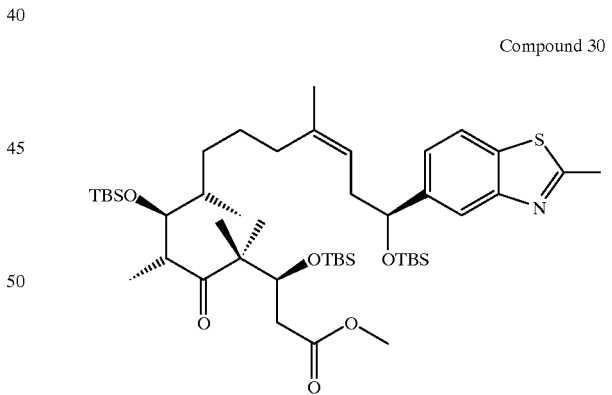

To a solution of 1.001 g of 96 in 10 ml of THF were added 4.2 ml of a 0.5M solution of BBN in THF (Aldrich) under Ar and the mixture was stirred at RT for 4 h (solution A). In a separate flask 0.679 g of vinyl iodide 5 were added to a mixture of 0.934 g Of CS₂CO₃, 0.117 g of Ph₃As, 0.140 g of PdCl₂(dppf), and 0.310 ml of water in 10 ml of DMF (solution B). Solution B was cooled to −10° C. and then solution A was added. Tho reaction mixture was allowed to warm to RT and stirred at RT for 21h, when 50 ml of water were added. The aqueous solution was then extracted three times with 50 ml of AcOEt each and the combined organic extracts were once washed with 50 ml of water. After drying over Na$_2$SO$_4$ and evaporation of solvent the residue was purified by FC in hexane/AcOEt 9/1 (2 runs) to provide 1.137 g of 30.

ESI-MS: 876 (M+H). $^1$H-NMR (CDCl$_3$, 500 MHz): δ (ppm vs. TMS )=7.86 (s, 1H); 7.73 (d, 1H); 7.32 (dd, 1H); 5.16 (t, 1H); 4.73 (t, 1H); 4.37 (dd, 1H); 3.74 (dd, 1H); 3.66 (s, 3H); 3.11 (m, 1H); 2.83 (s, 3H); 2.45–2.20 (m, 3H); 1.90 (m, 2H); 1.62 (s, 3H); 1.30 (m, 4H); 1.19 (s, 3H).

Compound 16 (alternative procedure)

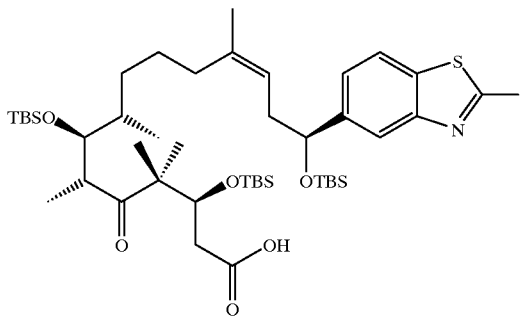

To a solution of 0.910 g of compound 30 in iso-propanol/water 4/1 were added 0.262 g of LiOHxH$_2$O and the mixture was heated to 50° C. for 5 h. The reaction mixture was then evaporated to dryness, 10 ml of water were added to the residue and the pH was adjusted to ca. 4.5 with 0.1N HCl. The aqueous solution was then extracted three times with 150 ml of CH$_2$Cl$_2$ each, the combined organic extracts were dried over Na$_2$SO$_4$, and the solvent was evaporated. The residue was purified by FC in hexane/AcOEt 6/4 (2 runs) to provide 0.768 g of 16.

18 (alternative procedure)

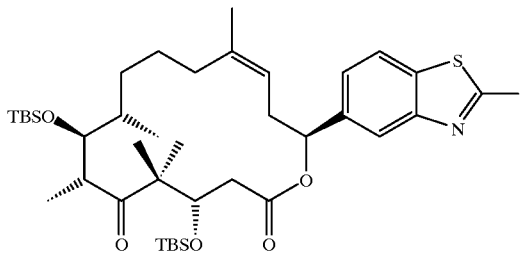

To a solution of 0.709 g of hydroxy acid 17 in 25 ml of THF at 0° C. were added 0.792 ml of Et$_3$N and 0.783 ml of 2,4,6-trichlorobenzoyl chloride and the mixture was stirred at this temperature for 15 min. It was then diluted with additional 115 ml of THF and added dropwise to a solution of 1.157 g of dimethylamino-pyridine in 840 ml of toluene, which was kept at 75° C., over a period of three hours. After complete addition the mixture was stirred at RT for additional two hours. It was then filtered and the filtrate was evaporated to dryness. The residue was distributed between 200 ml of AcOEt and 150 ml of sat. aqu. NaHCO$_3$ and the organic layer was separated. The aqueous layer was additionally extracted with two 200 ml portions of AcOEt and the combined organic extracts were washed with 150 ml of water. After drying over Na$_2$SO$_4$ and evaporation of solvent, the residue was purified by FC in hexane/AcOEt 9/1 to provide 0.425 g of 18.

Compound 19 (alternative procedure)

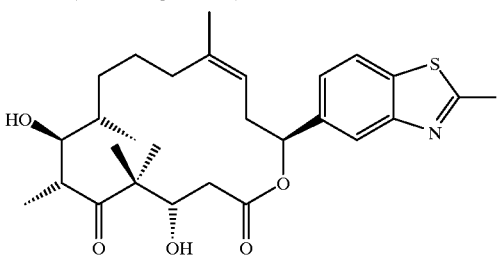

To a solution of 0.487 mg of compound 18 in 75 ml of THF were added 27 ml of HF-pyridine at 0° C. The reaction mixture was stirred at RT for 20 h, at which point it was cooled to 0° C. and 300 ml of sat. aqu. NaHCO$_3$ were added. After stirring for 30 min the solution was three times extracted with 250 ml of AcOEt each and the combined organic extracts were once washed with 250 ml of water. After drying over Na$_2$SO$_4$ and evaporation of solvent, the residue was purified by FC in hexane/AcOEt 6/4 and 7/3 (two runs) to provide 0.276 mg of 19.

Compound 19a

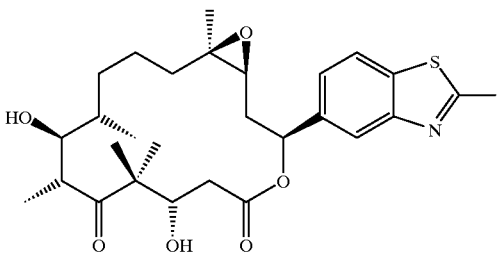

To a solution of 0.100 g of 19 in 5 ml of CH$_2$Cl$_2$ were added dropwise 15 ml of a ca. 0.044M solution of dimethyldioxirane in acetone (DMDO; prepared according to: Organic Synthesis 1997, 74, 91) under Ar at −78° C. The mixture was stirred at −50° C. for 2 h, when additional 5 ml of the DMDO solution were added at this temperature. Two further portions of the DMDO solutions were added 4 h (10 ml) and 6h (5 ml) after the first addition. After 6.5 h the solvent was removed in vacuo at −50° C. and the residue was purified by FC AcOEt/hexane 3/2, CH$_2$Cl$_2$/acetone 8/1, and CH$_2$Cl$_2$/acetone 8/1 (3 runs) to provide 0.0477 g of stereochemically homogeneous 19a.

ESI-MS: 518.1 (M+H). $^1$H-NMR (CDCl$_3$, 400 MHz): δ (ppm vs. TMS)=7.6 (s, 1H); 7.83 (d, 1H); 7.3 (dd, 1H); 6.35 (m, 1H); 4.10 (m, 1H); 3.79 (m, 2H); 3.38 (m, 1H); 2.86 (s, 3H); 2.75; (t, 1H); 1.30 (s, 3H); 1.25 (s, 3H); 1.19 (d, 3H); 1.08 (s, 3H); 1.04 (d, 3H).

The following further compounds are produced analogously to the processes described in this disclosure, specifically by the processes as provided in detail below:

| Example | compound | starting material |
|---------|----------|-------------------|
| 5 | | (1″) (compound 35) |
| 6 | | (example 5) |
| 7 | | (2″) |
| 8 | | (example 7) |
| 9 | | (3″) |
| 10 | | (example 9) |

-continued

| Example | compound | starting material |
|---|---|---|
| 11 | | (4″) benzothiazole-6-carbaldehyde |
| 12 | | (example 11) |
| 13 | | (5″) (compound 40) 2-methyl-1H-benzimidazole-5-carbaldehyde |
| 14 | | (example 13) |
| 15 | | (6″) (compound 49) 1-methyl-1H-benzimidazole-6-carbaldehyde |
| 16 | | (example 15) |

-continued

| Example | compound | starting material |
|---|---|---|
| 17 | | (7″) (compound 62) |
| 18 | | (example 17) |
| 19 | | (8″) |
| 20 | | (example 19) |
| 21 | | (9″) |
| 22 | | (example 21) |

-continued

| Example | compound | starting material |
|---|---|---|
| 23 | (structure) | (10″) 2-methylquinoline-7-carbaldehyde |
| 24 | (structure) | (example 23) |
| 25 | (structure) | (11″) 4-methylquinoline-7-carbaldehyde |
| 26 | (structure) | (example 25) |
| 27 | (structure) | (12″) quinoline-6-carbaldehyde |
| 28 | (structure) | (example 27) |

-continued

| Example | compound | starting material |
|---|---|---|
| 29 | (structure) | (13″) |
| 30 | (structure) | (example 29) |
| 31 | (structure) | (14″) |
| 32 | (structure) | (example 31) |
| 33 | (structure) | (15″) |
| 34 | (structure) | (example 33) |

Starting materials:

(1"): see compound 35 below)
(2") 2,6-dimethyl-benzoate [see J. Org. Chem. 46, 3256 (1981)].
(5") 2-methyl-(1H)-benzimidazole-5-carbaldehyde—see compound 40 below
(6") 1-methyl-(1H)-benzimidazole-5-carbaldehyde—see compound 49 below
(7") 1,2,5-trimethyl-(1H)-benzimidazole-5-carbaldehyde—see compound 62 below.
(8") 3-methyl-(3H)-benzimidazole-5-carbaldehyde
(9") quinoline-7-carbaldehyde (see J. Med. Chem., 36, 3308 (1993), Aldrich) (10") 2,7-dimethyl-quinoline (Aldrich).
(11") 4-methyl-quinoline-7-carbaldehyde (obtainable by means of DIBAL-H reduction of 4-methyl-quinoline-7-carboxylic acid methylester (Bull. Soc. Chim. Fr., S. 789 (1996)).
(12") quinoline-6-carbaldehyde (see Liebigs Ann. Chem., 699, 98, (1966)).
(13") 2,6-dimethyl-quinoline (Aldrich).
(14") 2-tert-butyl-dimethylsilyloxy)-methyl-benzothiazol-5-carbaldehyde
(15") 2-fluoromethyl-benzothiazole-5-carbaldehyde EXAMPLES 5/6—Precursors Compound 31

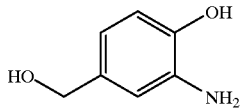

49 g of 4-hydroxy-3-nitro-benzyl alcohol are hydrogenated over 10% Pd-C in EtOH (1000 ml) at RT and atmospheric pressure. After 2 h the catalyst is removed by filtration and the solvent evaporated. Recrystallization of the residue from acetone/hexane 15/6 gives 31 as very light red crystals. 142–43° C.ESI-MS: 139.9 (M+H). $^1$H-NMR (DMSO-d$_6$, 400 MHz): δ (ppm vs. TMS)=8.80 (s, br, 1H); 6.53 (m, 2H); 6.30 (dd, 1H); 4.79 (t, 1H); 4.42 (s, br, 2H); 2.22 (d, 2H).

Compound 32

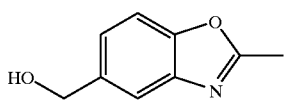

A solution of 10.0 g of compound 31, 19.7 ml of triethyl-orthoacetate, and 0.15 ml of conc. HCl in 40 ml of MeOH is heated to reflux for 3 h. After cooling to RT the solvent is evaporated and the residue re-dissolved in 250 ml of AcOEt. This solution is extracted once with 80 ml of 1N NaOH and 80 ml of water each. The combined aqueous extracts are re-extracted with 250 ml of AcOEt. The combined organic extracts are dried over Na$_2$SO$_4$ and the solvent evaporated. The residue is purified by FC in CH$_2$Cl$_2$/MeOH 95/5 (twice) and subsequently CH$_2$Cl$_2$ 98/2 to provide the title compound. M.p. 96–98° C. ESI-MS: 167.9 (M+H). $^1$H-NMR (DMSO-d$_6$, 300 MHz): δ (ppm vs. TMS)=7.33 (s, 1H); 7.10 (dd, 1H); 6.70 (d, 1H); 3.73 (s, 3H).

Compound 33

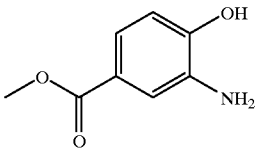

A solution of 20.0 g of 4-hydroxy-3-amino-benzoic acid (FLUKA) in 700 ml MeOH is saturated with HCl gas and then heated to reflux for 16 h. Water (200 ml) is then added to the mixture and the pH adjusted to ca. 7 by addition of 310 ml of 4N NaOH. The solution is then saturated with NaCl and extracted with three portions of 400 ml of AcOEt each. The combined organic extracts are dried over Na$_2$SO$_4$ and the solvent is evaporated. Recrystallization of the residue from AcOEt/hexane 1/1 gives 33 as crystalline solid. M.p. ≅205° C. (dec.) ESI-MS: 167.9 (M+H). $^1$H-NMR (DMSO-d$_6$, 300 MHz): δ (ppm vs. TMS)=7.33 (s, 1H); 7.10 (dd, 1H); 6.70 (d, 1H); 3.73 (s, 3H).

Compound 34

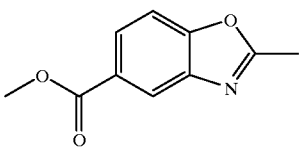

A mixture of 7.0 g of 33, 11.5 ml of triethyl-orthoacetate, 13 ml of MeOH, and 0.103 ml of conc. is heated to reflux for 5 h. The reaction mixture is them evaporated to dryness, the residue taken up in 100 ml of ether and this solution washed with 50 ml of NaOH and 50 ml of water. The combined aqueous extracts are re-extracted with 100 ml of ether. The combined organic extracts are dried over Na2SO4 and the solvent is evaporated to provide 34 as a solid. M.p. 68–69° C. ESI-MS: 191.9 (M+H). $^1$H-NMR (DMSO-d$_6$, 300 MHz): δ (ppm vs. TMS)=8.19 (s, 1H); 7.99 (d, 1H); 7.79 (d, 1H); 3.87 (s, 3H); 2.76 (s, 3H).

Compound 32

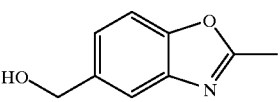

To a solution of 9.0 g of compound 33 in 100 ml of THF are added 141 ml of a 1M solution of DIBAL-H in THF at a temperature between −78° C. and −68° C. over a period of 25 min. The solution is then stirred for 3 h at a temperature between −10° C. and 0° C., at which point additional 40 ml of the DIBAL-H solution are added. After further 4 h in the same temperature range the mixture is Pooled to −40° C. and 250 ml of water are added carefully. After addition of 500 ml of CH$_2$Cl$_2$ the mixture is filtered, the residue washed 3× with 250 ml of CH$_2$Cl$_2$ each and water is added to the combined filtrates. After addition of solid NaCl the layers are separated and the organic solution is washed with 250 ml of water. The combined aqueous extracts are re-extracted twice with 250 ml of CH$_2$Cl$_2$ each, the combined organic extracts are dried over Na$_2$SO$_4$, and the solvent is evaporated. The residue is purified by FC in CH$_2$Cl$_2$/MeOH 95/5 to provide 32 as an oil.

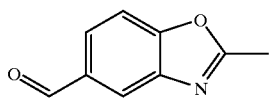

Compound 35

To a solution of 1.87 ml of oxalyl chloride in 50 ml of CH$_2$Cl$_2$ s added a solution of 3.21 ml of DMSO in 10 ml of CH$_2$Cl$_2$ at −78° C. over a period of 15 min. The solution is stirred at this temperature for 10 min. A solution of 2.69 of compound 32 is then added at −20° C. dropwise within 20 min and the mixture is stirred at this temperature for 2 h, 16 ml of Et$_3$N are then added dropwise over 10 min and the reaction mixture is allowed to warm to RT within 1 h. 100 ml of water are added followed by 100 ml of CH$_2$Cl$_2$ and another 100 ml of water. The layers are separated and the organic solution is washed with 100 ml of brine. The combined aqueous solutions are extracted with 100 ml of CH$_2$Cl$_2$. The combined organic extracts are dried over Na$_2$SO$_4$ and the solvent is evaporated. Purification of the residue by FC with CH$_2$Cl$_2$/MeOH 95/5 as eluent gives the title compound as an oil. M.p. 78–81° C. ESI-MS: 161.9 (M+H). $^1$H-NMR (CDCl$_3$, 300 MHz): δ (ppm vs. TMS)= 10.10 (s, 1H); 8.18 (s, 1H); 7.91 (d, 1H); 7.61 (d, 1H); 2.70 (s, 3H).

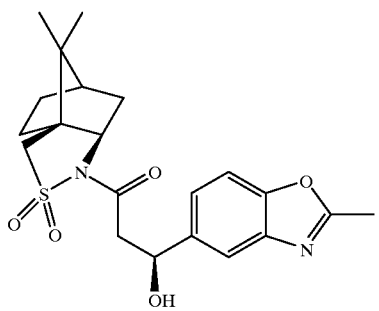

Compound 36

Compound 36 is prepared in analogy to alcohol 2 from 0.439 of compound 35 and 0.500 g of (2R)-acetylbornane-10,2-sultam. Purification is effected by FC inAcOEt/hexane 1/1 to provide a ca. 2/1 mixture of compound 36 and its 2-R-diastereoisomer. ESI-MS: 419.1 (M+H). $^1$H-NMR (CDCl$_3$, 300 MHz): δ (ppm vs. TMS)=7.69 (s, 1H); 7.44 (d, 1H); 7.36 (d, 1H); 5.30 (m, 1H); 3.48 (q, 2H); 3.15 (m, 2H); 2.63 (s, 3H); 2.20–2.05 (m, 2H); 1.90 (m, 2H); 1.40 (m, 2H); 1.10 (2xs (ca. 2/1), 3H); 0.98 (s, 3H).

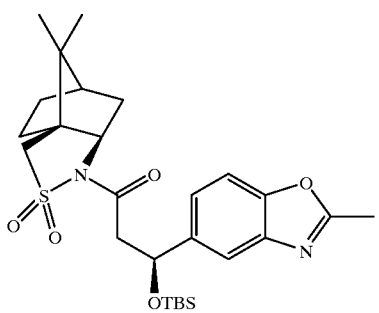

Compound 37

Compound 37 is prepared in analogy to TBS-ether 3 from 0.100 g of compound 36 and 0.056 g of TBS-Cl, except that the reaction is conducted at 45° C. throughout. Purification is effected by FC in AcOEt/hexane 7/3 and AcOEt/hexane 8/2 (two runs) to provide 0.060 g of compound 37. ESI-MS: 533.1 (M+H). $^1$H-NMR (CDCl$_3$, 400 MHz): δ (ppm vs. TMS)=7.82 (s, 1H); 7.59 (d, 1H): 7.54 (d, 1H); 5.52 (m, 1H); 3.98 (m, 1H): 3.56 (q, 2H): 3.32 (d, 2H); 2.82 (s, 3H); 2.18 (m, 1H); 2.02 (m, 3H); 1.94 (m, 1H); 1.50 (m, 2H); 1.06 (s, 3H); 1.02 (s, 9H); 0.92 (s, 3H); 0.25 (s, 3H); 0.22 (s, 3H).

EXAMPLES 13/14—PRECURSORS

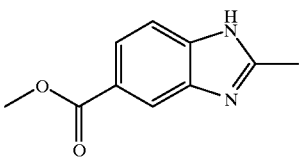

Compound 38

A solution of 10.4 g of 2-methyl-1H-benzimidazole-5-carboxylic acid (ACROS) and 10 ml of conc. sulfuric acid in 600 ml of MeOH are heated to reflux for 12 h. After cooling to RT the solvent is evaporated and 300 ml of ice-water are added to the residue followed by addition of 50 ml of 4N NaOH. From the resulting suspension (ca. pH 9) the product is isolated by filtration, washed with 200 ml of water and dried in vacuo to give 38 as a white crystalline powder.M.p. 181–182° C. ESI-MS: 191.0 (M+H). $^1$H-NMR (CDCl$_3$, 300 MHz): δ (ppm vs. TMS)=8.28 (s, 1H); 7.96 (d, 1H); 7.55 (d, 1H); 5.3 (s, br); 3.95 (s, 3H); 2.68 (s, 3H).

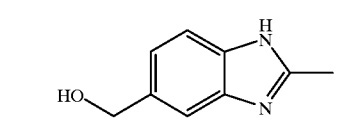

Compound 39

To a solution of 8.00 g of compound 38 in 200 ml of THF are added 100 ml of a 1M solution of DIBAL-H in THF at −78° C. over a period of 20 min. The solution is allowed too warm up to RT over a period of 4 h and then stirred at RT for an additional 4 h. After this period it is again cooled to −78° C., additional 50 ml of the DIBAL-H solution are added, and the reaction mixture is allowed to re-warm to RT. After 10 h of stirring at RT the reaction mixture is cooled to 0° C. and 100 ml of MeOH are added dropwise. To this mixture are added 80 g of silica gel and the solvents are evaporated. After drying, the silica gel with the adsorbed material is put on top of a flash column and the product eluted and purified by FC with CH$_2$Cl$_2$/MeOH 4/1 as eluent. This procedure gives the title compound as white crystals. M.p. 191–193° C. ESI-MS: 163.0 (M+H). $^1$H-NMR (CD$_3$OD, 400 MHz): δ (ppm vs. TMS)=7.48 (s, 1H); 7.42 (d, 1H); 7.19 (d, 1H); 4.68 (s, 2H); 2.53 (s, 3H).

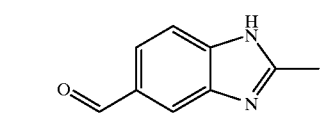

Compound 40

To a solution of 3.52 ml of oxalyl chloride in 90 ml of CH$_2$Cl$_2$ is added a solution of 5.9 ml of DMSO in 18 ml of CH$_2$Cl$_2$ at −75° C. over a period of 5 min. The solution is stirred at this temperature for 10 min, when 20 ml of CH2Cl2 (dropwise), 4.9 g of compound 39 (solid)) and in 160 ml of $CH_2Cl_2$ (dropwise) are added, The mixture is stirred at −78° C. for 20 h, when a uniform suspension has formed. 28.4 ml of $Et_3N$ are then added dropwise at the same temperature over a period of 10 min, resulting in the formation of an almost clear solution. The cooling bath is removed and the mixture allowed to a temperature of −10° C., when 150 ml of water are added. After addition of 200 ml of $CH_2Cl_2$ the layers are separated and the aqueous solution is extracted 4× with 200 ml of $CH_2Cl_2$ each. The combined organic extracts are dried over $MgSO_4$ and the solvent is evaporated. The residue is briefly dried in vacuo and then purified by FC with $CH_2Cl_2$/MeOH 9/1 as eluent to give compound 40. M.p. 228–230° C. ESI-MS: 161.1 (M+H). $^1$H-NMR ($CD_3OD$, 400 MHz): δ (ppm vs. TMS)= 10.00 (s, 1H); 8.05 (s, 1H); 7.80 (d, 1H); 7.61 (s, 1H); 2.61 (s, 3H).

Compound 41

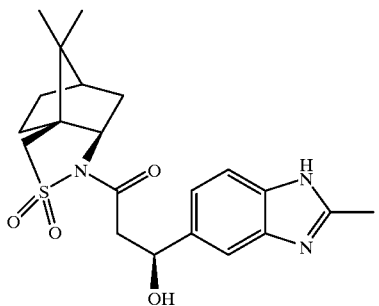

Compound 41 is prepared in analogy to alcohol 2 from 4.75 g of compound 4 g and 4.91 g of sultam 1, except that 49 is added as a solid and additional $CH_2Cl_2$ is added to the reaction mixture separately. The reaction mixture after addition of the aldehyde becomes a suspension and remains so until quenching. Purification is effected by FC in 7% MeOH/$CH_2Cl_2$ to provide a ca. 3/1 mixture of compound 41 and its 2-R-diastereoisomer, which is also slightly contaminated with 49. M.p. ° C. ESI-MS: 418.1 (M+H). $^1$H-NMR ($CDCl_3$, 400 MHz, major isomer): δ (ppm vs. TMS)=7.50 (m, 2H); 7.22 (d, 1H); 5.51 (m, 1H); 3.88 (m, 1H); 3.45 (m, 2H); 3.18 (m, 2H); 2.60 (s, 3H); 2.08 (m, 2H); 1.90 (m, 3H); 1.08 (s, 3H); 0.97 (s, 3H).

Compound 42

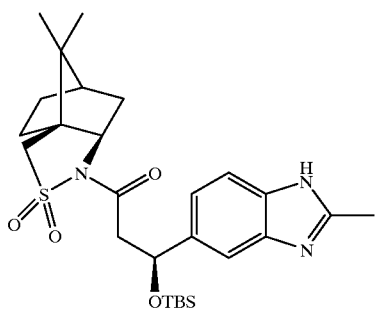

Compound 42 is prepared in analogy to TBS-ether 3 from 3.0 g of compound 41 and 1.62 g of TBS-Cl, except that the reaction is conducted at 45° C. throughout. Purification is effected by FC in $CH_2Cl_2$/acetone/MeOH 70/30/2 (two runs) to provide 42 with a diastereomeric purity of >95%. M.p. ° C. ESI-MS: 532.1 (M+H). $^1$H-NMR ($CDCl_3$, 400 MHz, major isomer): δ (ppm vs. TMS)=7.50 (m, very broad, 2H); 7.22 (d, broad, 1H); 5.32 (t, 1H); 3.77 (m, 1H); 3.47 (dd, 2H); 3.13 (d, 2H); 2.61 (s, 3H); 1.96 (m, 1H); 1.83 (m, 2H); 1.25 (m, 1H); 0.85 (s, 3H); 0.83 (s, 9H); 0.6 (s, br, 3H); 0.03 (s, 3H); −0.19 (s, 3H)

Compound 43

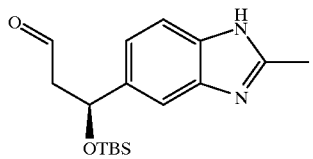

Compound 43 is prepared in Analogy to aldehyde 4 from 1.64 g of compound 42 and 7.5 ml of a 1M DIBAL-H solution in $CH_2Cl_2$, except that the reaction is quenched with water rather than MeOH and that the filtration step in the work-up can be omitted.

EXAMPLES 15/16—PRECURSORS

Compound 44

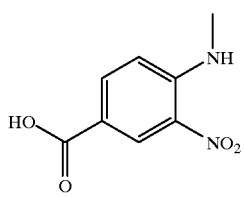

A mixture of 15 g of 4-fluoro-3-nitro-benzoic acid (ALDRICH), 150 ml of a 33% solution of methyl amine in EtOH and 400 ml of EtOH is stirred at RT for 18 h. The mixture is then evaporated to dryness, 500 ml of water are added to the residue, and the product is precipitated by addition 43 ml of 2N HCl to the orange-red solution. Filtration, washing with 400 ml of water, and drying in vacuo gives 44 as a yellow powder. M.p. >290° C. ESI-MS: 197.1 (M+H). $^1$H-NMR (DMSO-$d_6$, 300 MHz): δ (ppm vs. TMS)=8.60 (d, 1H); 8.55 (q, 1H); 7.98 (dd, 1H); 7.03 (d, 1H); 3.00 (d, 3H).

Compound 45

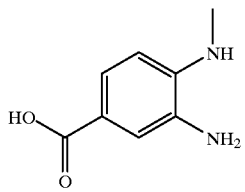

Compound 44 (9.37 g) is hygrogenated over Ra-Ni in EtOH/THF 1/2 at RT and atmospheric pressure. After. 17 h the catalyst is removed by filtration and the filtrate is evaporated to provide 45 as a grey powder. ESI-MS (negative mode): 165.2 (M−H). $^1$H-NMR (DMSO-$d_6$, 300 MHz): δ (ppm vs. TMS)=7.41 (d, 1H); 7.13 (d, 1H); 6.47 (d, 1H); 5.32 ("d", br, 1H); ≅4.65 (s, very broad); 2.77 (d, 3H).

Compound 46

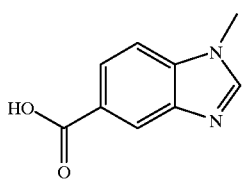

A solution of 12.95 g of compound 45 and 80 ml triethyl-orthoformate in 400 ml of EtOH are heated to reflux for 3 h. After cooling to RT the product is isolated by filtration, washed with 100 ml of EtOH and dried in vacuo. Evaporation of the combined filtrates provides additional 46. M.p. >280° C. (dec,). ESI-MS; 177.0 (M+H). $^1$HNMR (DMSO-$d_6$, 300 MHz): δ (ppm vs. TMS)=8.32 (s, 1H); 8.23 (s, 1H); 7.90 (d, 1H); 7.65 (d, 1H); 3.88 (s, 3H).

Compound 47

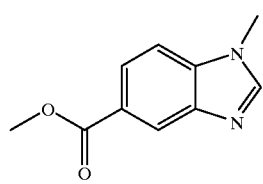

A solution of 13.2 g of compound 46 and 12.5 ml of conc. sulfuric acid in 750 ml of MeOH are heated to reflux for 7 h. After cooling to RT 250 ml of ice-water are added to the residue followed by addition of 63 ml of 4N NaOH. The aqueous solution is extracted twice with 400 ml of $CH_2Cl_2$ each and the combined organic extracts are washed with 200 ml of water. The pH of the wash extract is then adjusted to 10 and it is re-extracted with $CH_2Cl_2$. The combined organic extracts are dried over $MgSO_4$ and the solvent is evaporated to give 47 as a dark-brown crystalline powder. ESI-MS; 191.1 (M+H). $^1$HNMR (DMSO $d_6$, 300 MHz): δ (ppm vs. TMS)=8.35 (s, 1H); 8.26 (s, 1H); 7.90 (d, 1H); 7.68 (d, 1H); 3.88 (2×s, 6H).

Compound 48

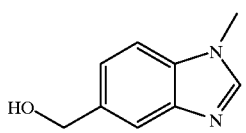

To a solution of 1.00 g of compound 47 in 25 ml of THF are added 12.6 ml of a 1M solution of DIBAL-H in THF at −78° C. over a period of 10 min. The solution 13 allowed too warm up to RT over a period of 5 h, cooled to −30° C., and 15 ml of MeOH are added. To this mixture are added 10 g of silica gel and the solvents are evaporated. After drying, the silica gel with the adsorbed material is put on top of a flash column and the product eluted and purified by FC with $CH_2Cl_2$/MeOH 9/1 as eluent. This procedure gives 0.678 g of the title compound as beige-orange crystals. M.p. 151–152° C. ESI-MS: 163.0 (M+H). $^1$H-NMR (DMSO-$d_6$, 300 MHz): δ (ppm vs. TMS)=7.90 (s, 1H); 7.76 (s, 1H); 7.37 (s, 2H); 4.80 (s, 2H); 3.84 (s, 3H).

Compound 49

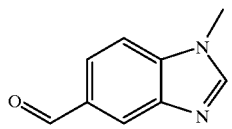

To a solution of 4.54 ml of oxalyl chloride in 120 ml of $CH_2Cl_2$ is added a solution of 7.6 ml of DMSO in 25 ml of $CH_2Cl_2$ at −75° C. over a period of 5 min. The solution is stirred at this temperature for 10 min, when a mixture of 6.32 g of compound 48 and 240 ml of $CH_2Cl_2$ is added in portions over a 15 min period. The mixture is stirred at −78° C. for 4 h, when a uniform yellow suspension has formed. 36.5 ml of $Et_3N$ are then added dropwise at the same temperature over a period of 10 min, resultin in the formation of a clear yellow solution. The cooling bath is removed and the mixture allowed to a temperature of −10° C., when 150 ml of water are added. After addition of 200 ml of $CH_2Cl_2$ and 50 ml of water the layers are separated and the aqueous solution is extracted with 200 ml $CH_2Cl_2$. The combined organic extracts are washed with 100 ml of water, dried over $MgSO_4$, and the solvent is evaporated. The residue is briefly dried in vacuo and then purified by FC with $CH_2Cl_2$/MeOH 95/5 as eluent to give 49 as white crystals. ESI-MS: 160.9 (M+H). $^1$H-NMR (CDCl$_3$, 400 MHz): δ (ppm vs. TMS)=10.10 (s, 1H); 8.31 (s, 1H); 8.00 (s, 1H); 3.91 (s, 3H).

Compound 50

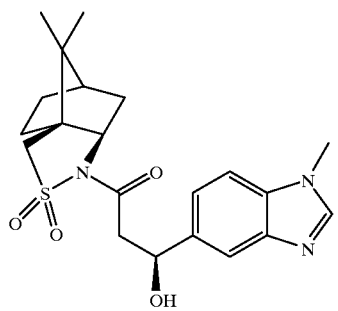

Compound 50 is prepared in analogy to alcohol 2 from 3.0 g of compound 49 and 4.91 g of sultam 1, except that 49 is added as a solid and additional $CH_2Cl_2$ is added to the reaction mixture separately. Purification is effected by FC in acetone/ACOET 1/1→3/2 to provide compound 50, which appears to be slightly contaminated by its R-diastereoisomer. ESI-MS: 418.2 (M+H). $^1$H-NMR (CDCl$_3$, 400 MHz, major isomer): δ (ppm vs. TMS)=8.05; (s, 1H); 8.00 (s, 1H); 7.41 (d, 1H); 7.37 (d, 1H); 5.35 (m, 1H); 3.95 (m, 1H); 3.92 (s, 3H); 3.45 (q, 2H); 3.17 (m, 2H); 1.10 (s, 3H); 0.96 (s, 3H).

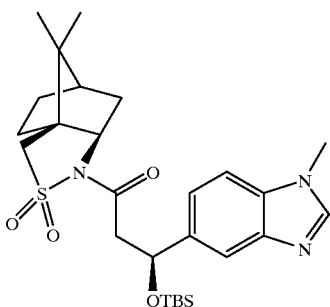

Compound 51

Compound 51 is prepared in analogy to TBS-ether 3 from 2.31 g of compound 50 and 1.24 g of TBS-Cl, except that the reaction is conducted at 45° C. throughout. Purification is effected by FC in CH$_2$Cl$_2$/acetone 7/3 (two runs) to provide 51. M.p. 90–93° C. ESI-MS: 532.1 (M+H). $^1$H-NMR (CDCl$_3$, 400 MH2). δ (ppm vs. TMS)=7.84 (s, 1H); 7.70 (s, 1H); 7.43 (d, 1H); 7.33 (d, 1H); 5.38 (t, 1H); 3.82 (s, 3H); 3.79 (m, 1H); 3.38 (s, 2H); 3.15 (m, 2H); 1.30 (m, 2H); 0.85 (s, 3H); 0.86 (s, 9H); 0.65 (s, 3H); 0.05 (s, 3H); −0.19 (s, 3H).

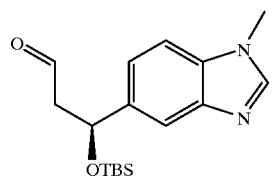

Compound 52

Compound 52 is prepared in analogy to aldehyde 4 from 1.96 g of compound 51 and 9 ml of a 1M DIBAL-H solution in CH$_2$Cl$_2$, except that the reaction is quenched with water rather than MeOH and that the filtration step in the work-up can be omitted. Purification is effected by FC in CH$_2$Cl$_2$/acetone 7/3 to provide 1 52 as a yellow oil. ESI-MS: 319.2 (M+H). $^1$H-NMR (CDCl$_3$, 400 MHz): δ (ppm vs. TMS)= 9.80 (s, 1H); 7.87 (s, 1H); 7.77 (s, 1H); 7.38 (d, 1H); 7.34 (d, 1H); 5.35 (m, 1H); 3.82 (s, 3H); 3.79 (m, 1H); 2.95 (dd, 1H); 1.30 (m, 2H); 0.86 (s, 9H); 0.65 (s, 3H); 0.05 (s, 3H); −0.18 (s, 3H).

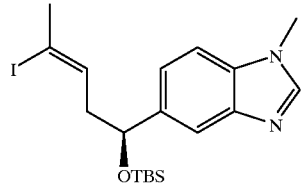

Compound 53

Compound 53 is prepared in analogy to vinyl iodide 5 from 1.12 g of compound 52 and 2.4 g of [Ph$_3$P-ChlCH$_3$]$^+$I$^-$, except that stirring at −78° C. after addition of NaHMDS to the suspension of [Ph$_3$P-ChlCH$_3$]$^+$I$^-$ is performed for 30 min and that the temperature is raised to −15° C. for 20 min before recoiling to −78° C. and addition of the aldehyde. Purification is effected by FC in CH$_2$Cl$_2$/acetone 4/1 to provide 53 as a viscous yellow oil, which crystallizes upon standing. M.p. 64–65° C. ESI-MS: 457 (M+H). $^1$H-NMR (CDCl$_3$, 400 MHz): δ (ppm vs. TMS)=7.85 (s, 1H); 7.74 (s, 1H); 7.35 (s, 2H); 5.46 (t, 1H); 4.90 (m, 1H); 3.83 (s, 3H); 2.55 (m, 1H); 2.46 (overlapping s and m, 4H); 0.89 (s, 9H); 0.65 (s, 3H); 0.04 (s, 3H); −0.13 (s, 3H).

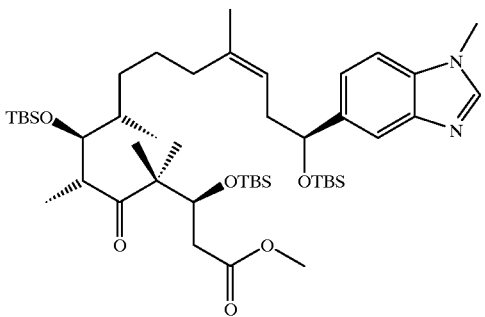

Compound 54

Compound 54 is prepared in analogy to compound 30 from 0.871 g of 96 and 0.563 g of compound 53. Purification is effected by FC in 3% MeOH/CH$_2$Cl$_2$ and 7% acetone/CH$_2$Cl$_2$ (2 runs) to provide 54 as a light orange oil. $^1$H-NMR (CDCl$_3$, 400 MHz): δ (ppm vs. TMS)=7.84 (s, 1H); 7.70 (s, 1H); 7.32 (s, 2H); 5.16 (t, 1H); 4.72 (dd, 1H); 4.38 (m, 1H); 3.83 (s, 3H); 3.75 (dd, 1H); 3.65 (s, 3H); 3.12 (m, 1H); 2.50–2.25 (m, 4H); 1.93 (m, 2H); 1.62 (s, 3H).

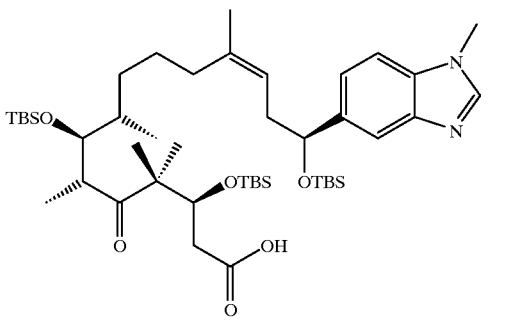

Compound 55

Compound 55 is prepared in analogy to compound 54 from 0.840 g of 54. Purification is effected by FC in 5% MeOH/CH$_2$Cl$_2$ (2 runs) to provide 55 as a white foam. ESI-MS: 845.2 (M+H). $^1$H-NMR (CDCl$_3$, 400 MHz): δ (ppm vs. TMS)=8.05 (s, 1H); 7.90 (s, 1H); 7.45 (s, 1H); 7.35 (d, 1H); 5.30 (t, 1H); 4.80 (dd, 1H); 4.55 (m, 1H); 3.83 (s, 3H); 3.68 (m, 1H); 3.22 (m, 1H); 2.42–2.20 (m, 4H); 1.73 (s, 3H).

Compound 56

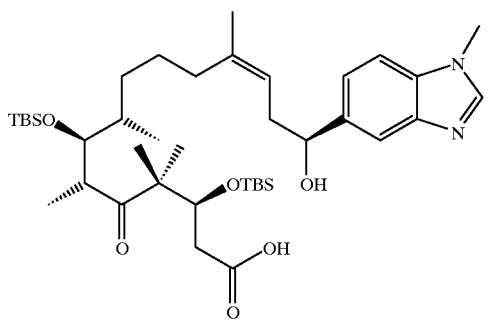

Compound 56 is prepared in analogy to hydroxy acid 17 from 0.738 g of 55. Purification is effected by FC in 8% MeOH/CH$_2$Cl$_2$ to provide 56 as a white foam ESI-MS: 845.2 (M+H). $^1$H-NMR (CDCl$_3$, 400 MHz): δ (ppm vs. TMS)=8.14 (s, 1H); 7.93 (s, 1H); 7.41 (d, 1H); 7.33 (d, 1H); 5.30 (t, 1H); 4.81 (dd, 1H); 4.55 (m, 1H); 3.85 (s, 3H); 3.63 (m, 1H); 3.22 (m, 1H); 2.99–2.40 (m, 3H); 2.35 (m, 1H); 1.90 (m, 1H); 1.77 (s, 3H); 1.70–1.50 (m, 3H); 1.20 (s, 3H); 1.13 (s, 3H); 1.10 (d, 3H); 0.95 (d, 3H); 0.90 (s, 9H); 0.87 (s, 9H).

Compound 57

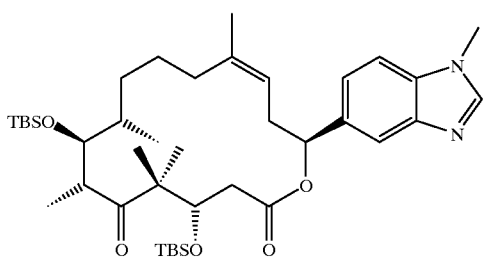

Compound 57 is prepared in analogy to 18 (lactone 18; "alternative procedure") from 0.470 g of 56. Purification is effected by FC in 15% acetone/CH$_2$Cl$_2$ and 2% MeOH/CH$_2$Cl$_2$ (two runs) to provide 57 as an oil, which was not entirely pure.

ESI-MS: 713.1 (M+H). $^1$H-NMR (CDCl$_3$, 400 MHz): δ (ppm vs. TMS)=7.87 (s, 1H); 7.82 (s, 1H); 7.38 (s, 1H); 7.23 (s, 1H); 5.61 (d, 1H); 5.25 (t, 1H); 3.95 (t, 1H); 3.90 (d, 1H); 3.83 (s, 3H); 1.71 (s, 3H).

Compound 58

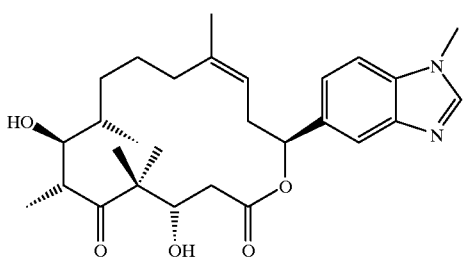

Compound 58 is prepared in analogy to 19 (lactone 19; "alternative procedure") from 0.084 g of 57. Purification is effected by FC in 5% MeOH/CH$_2$Cl$_2$ and subsequent recrystallization from CH$_2$Cl$_2$/hexane to provide 58 as a white crystalline solid. ESI-MS: 485.1 (M+H). $^1$H-NMR (CDCl$_3$, 500 MHz): δ (ppm vs. TMS)=7.87 (s, 1H); 7.84 (s, 1H); 7.37 (d, 1H); 7.33 (d, 1H); 5.95 (d, 1H); 5.22 (m, 1H); 4.18 (d, 1H); 3.84 (s, 3H); 3.74 (q, 1H); 3.18 (dq, 1H); 2.96 (m, 1H); 2.91 (s, br, OH); 2.52 (s, br, OH); 2.45 (m, 2H); 2.31 (dd, 2H); 1.91 (m, 2H); 1.68 (s, 3H); 1.27 (s overlapping with m); 1.20 (d, 3H); 1.05 (d, 3H); 1.02 (s, 3H).

EXAMPLES 17/18—PRECURSORS

Compound 59

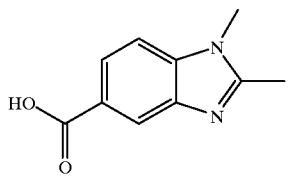

A solution of 8.78 g of compound 45 and 80 ml triethylorthoacetate in 100 ml of EtOH is heated to reflux for 7 h. After cooling to RT the product is isolated by filtration, washed with 25 ml of EtOH and dried in vacuo. Evaporation of the combined filtrates provides additional 59. M.p. >290° C. (dec.). ESI-MS (negative mode): 189.0 (M−H). $^1$H-NMR (DMSO-d$_6$, 300 MHz): δ (ppm vs. TMS)=12.70 (s, br, 1H); 8.10 (s, 1H); 7.82 (d, 1H); 7.55 (d, 1H); 3.75 (s, 3H); 2.55 (s, 3H).

Compound 60

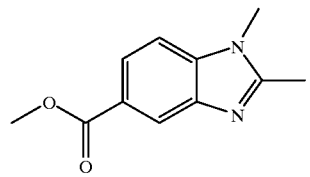

A solution of 8.23 g of compound 5 g and 7.5 ml of conc. sulfuric acid in 450 ml of MeOH are heated to reflux for 7 h. After cooling to RT 250 ml of ice-water are added to the residue followed by addition of 75 ml of 2N NaOH. From the resulting suspension (ca. pH 9) the product is isolated by filtration, washed with 200 ml of water and dried in vacuo to give 60 as a grey powder. M.p. 161–162° C. ESI-MS: 205.1 (M+H). $^1$H-NMR (CDCl$_3$, 300 MHz): δ (ppm vs. TMS)=8.39 (s, 1H); 7.98 (d, 1H); 7.29 (d, 1H); 3.95 (s, 3H); 3.75 (s, 3H); 2.63 (s, 3H).

Compound 61

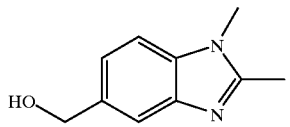

To a solution of 4.28 g of compound 60 in 110 ml of THF are added 50 ml of a 1M solution of DIBAL-H in THF at −78° C. over a period of 15 min. The solution is stirred over night when it has reached a temperature of 10° C. It is then allowed to warm to RT, cooled to 0° C., and 30 ml of MeOH are added dropwise. The mixture is evaporated to dryness and 500 ml of CH$_2$Cl$_2$ and 500 ml of water are added to the residue. After addition of 100 ml of 1N NaOH the layers are separated and the aqueous solution is extracted 5× with 300 ml CH₂Cl₂ each. The combined organic extracts are dried over MgSO₄, the solvent is evaporated and the residue briefly dried in vacuo. Purification by FC with CH₂Cl₂/MeOH 9/1 as eluent gives 61 as a beige crystalline powder. M.p. 165–166° C. ESI-MS: 177.0 (M+H). ¹H-NMR (CDCl₃, 300 MHz): δ (ppm vs. TMS)=7.63 (s, 1H); 7.25 ("m", 2H); 4.78 (s, 2H); 3.70 (s, 3H); 2.80 (s, br, 1H); 2.59 (s, 3H).

Compound 62

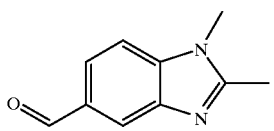

To a solution of 2.32 ml of oxalyl chloride in 60 ml of CH₂Cl₂ is added a solution of 4 ml of DMSO in 12 ml of CH₂Cl₂ at −75° C. over a period of 5 min. The solution is stirred at this temperature for 10 min, when a suspension of 3.52 g of compound 61 is added in portions over a 15 min period. The mixture is stirred at −78° C. for 2 h and then 18.8 ml of Et₃N are added dropwise at the same temperature over a period of 10 min. The cooling bath is removed and the mixture allowed to warm to a temperature of −10° C., when 120 ml of water are added. After addition of 150 ml of CH₂Cl₂ and 150 ml of water the layers are separated and the organic layer is washed with 150 ml of brine. The combined aqueous solutions are extracted with 200 ml CH₂Cl₂. The combined organic extracts are dried over MgSO₄, the solvent is evaporated and the residue briefly dried in vacuo. Purification by FC with AcOEt/acetone 1/1 as eluent gives 62 as white crystals. ESI-MS: 175.0 (M+H). ¹H-NMR (CDCl₃, 300 MHz): δ (ppm vs. TMS)=10.06 (s, 1H); 8.17 (s, 1H); 7.85 (d, 1H); 7.39 (d, 1H); 3.80 (s, 3H); 2.65 (s, 3H).

Compound 63

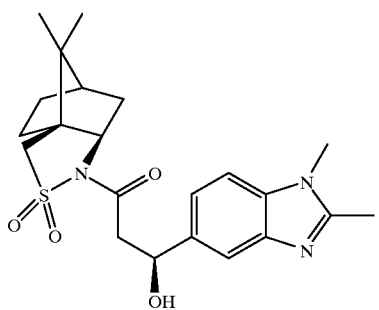

Compound 63 is prepared in analogy to alcohol 2 from 3.9 of compound 62 and 4.11 g of sultam 1, except that after complete addition of the solution of 62 the temperature of the reaction mixture is briefly raised to −60° C., in order to generate a clear solution. Purification was effected by FC in CH₂Cl₂/MeOH 9/1 to provide 63. ESI-MS: 432.0 (M+H.) ¹H-NMR (CDCl₃, 300 MHz): δ (ppm vs. TMS)=7.68 (s, 1H); 7.32 (t, 1H); 7.25 (d, 1H); 5.31 (m, 1H); 3.89 (m, 1H); 3.72 (s, 3H); 3.45 (m, 3H); 3.15 (m, 2H); 2.60 (s, 3H); 2.25–2.05 (m, 2H); 1.40 (m, 2H); 1.11 (s, 3H); 0.97 (s, 3H).

Compound 64

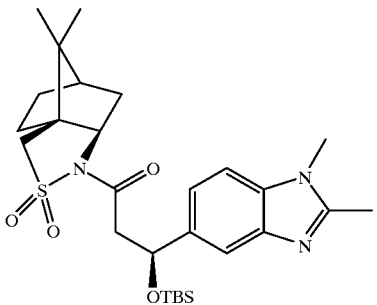

Compound 64 is prepared in analogy to TBS-ether 3 from 5.03 g of compound 63 and 2.63 g of TBS-Cl, except that the reaction is conducted at 45° C. throughout. Purification is effected by FC in CH₂Cl₂/acetone 7/3 to provide 63. M.p. 90–93° C. ESI-MS: 546.0 (M+H). ¹H-NMR (CDCl₃, 300 MHz): δ (ppm vs. TMS)=7.63 (s, 1H); 7.39 (d, 1H); 7.25 (overlapping with solvent signal, 1H); 5.35 (t, 1H); 3.80 (m, 1H); 3.75 (s, 3H); 3.39 (s, 2H); (m, 3H); 3.19 (dd, 1H); 3.07 (dd, 1H); 2.65 (s, 3H); 2.05–1.75 (m, 5H); 0.89 (s, 3H); 0.83 (s, 9H); 0.78 (s, 3H); 0.05 (s, 3H); −0.2 (s, 3H).

Compound 65

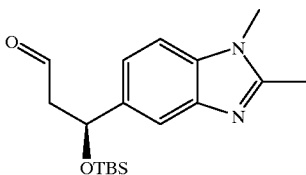

Compound 65 is prepared in analogy to aldehyde 4 from 3.4 g of compound 64 and 15 ml of a 1M DIBAL-H solution in CH₂Cl₂, except that the reaction is quenched with water rather than MeOH and that the filtration step in the work-up can be omitted. Purification is effected by FC in CH₂Cl₂/acetone 7/3 to provide 65. M.p. 83–85° C. ESI-MS: 365.2 (M+Na). ¹H-NMR (CDCl₃, 400 MHz): δ (ppm vs. TMS)= 9.96 (s, 1H); 7.86 (s, 1H); 7.46 (s, 2H); 5.50 (m, 1H); 3.86 (s, 3H); 3,07 (m, 1H); 2.82 (m, 2H); 2.81 (s, 3H); 1.03 (s, 9H); 0.22 (s, 3H); 0 (s, 3H).

Compound 66

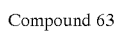

Compound 66 is prepared in analogy to vinyl iodide 5 from 1.65 g of compound 65 and 3.41 g of [Ph₃P-ClCH₃]⁺ I⁻, except that stirring at −78° C. after addition of NaHMDS to the suspension of [Ph₃P-ClCH₃]⁺I⁻, is performed for 30 min and that the temperature is raised to −15° C. for 20 min before re cooling to −78° C. and addition of the aldehyde. Purification is effected by FC in CH₂Cl₂/acetone 4/1 to provide 66. M.p. 71–72° C. ESI-MS: 471.0 (M+H).

¹H-NMR (CDCl₃, 400 MHz): δ (ppm vs. TMS)=7.61 (s, 1H); 7.22 (m, 2H); 5.45 (t, 1H); 4.85 (m, 1H); 3.71 (s, 3H); 2.60 (s, 3H); 2.55 (m, 1H); 2.45 (overlapping m and s, 4H); 0.87 (s, 9H); 0.02 (s, 3H); −0.12 (s, 3H).

Compound 67

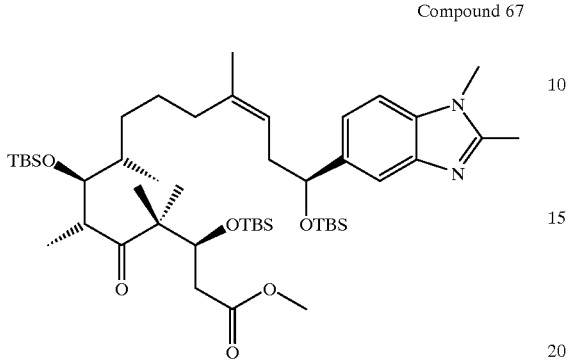

Compound 67 is prepared in analogy to compound 30 from 1.5 g of 96 and 0.620 g of compound 66. Purification is effected by FC in 3% MeOH/CH₂Cl₂ and 2% MeOH/CH₂Cl₂ (2 runs) to provide 67 as a orange-coloured oil. ESI-MS: 873.1 (M+H). ¹H-NMR (CDCl₃, 400 MHz): δ (ppm vs. TMS)=7.59 (s, 1H); 7.21 (m, 2H); 5.15 (t, 1H); 4.70 (dd, 1H); 4.38 (m, 1H); 3.75 (d, 1H); 3.71 (s, 3H); 3.67 (s, 3H); 3.05 (m, 1H); 2.59 (s, 3H); 2.42 (dd, 2H); 2.30 (m, 2H); 1.90 (m, 2H); 1.62 (s, 3H).

Compound 68

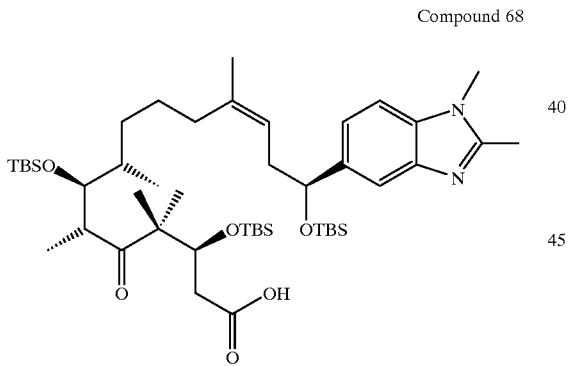

Compound 68 is prepared in analogy to compound 16 from 1.48 g of 67. Purification is effected by FC in 3% MeOH/CH₂Cl₂ to provide 68 as a white foam. ESI-MS: 859.2 (M+H). ¹H-NMR (CDCl₃, 400 MHz): δ (ppm vs. TMS)=7.96 (s, 1H); 7.38 (d, 1H); 7.21 (d, 1H); 5.30 (t, 1H); 4.78 (dd, 1H); 4.58 (m, 1H); 3.72 (s, 3H); 3.71 (m, 1H); 3.22 (m, 1H); 2.59 (s, 3H); 2.45–2.20 (m, 5H); 1.71 (s, 3H); 1.22 (s, 3H); 1.10 (overlapping s and d, 6H); 0.95 (d, 3H); ca. 0.88 (3×s, 27H).

Compound 69

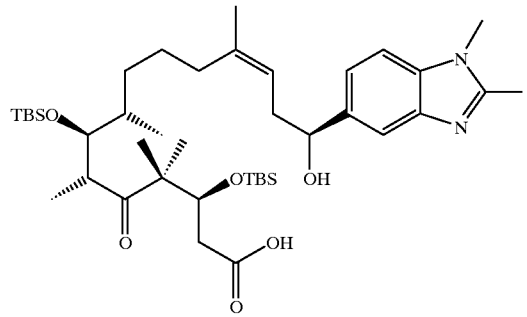

Compound 69 is prepared in analogy to hydroxy acid 17 from 1.23 g of 68. Purification is effected by FC in 5% MeOH/CH₂Cl₂ to provide 69 as a white foam. ESI-MS: 745.3 (M+H). ¹H-NMR (CDCl₃, 400 MHz): δ (ppm vs. TMS)=8.02 (s, 1H); 7.32 (d, 1H); 7.20 (d, 1H); 5.30 (t, 1H, overlapping with traces of CH₂Cl₂); 4.78 (dd, 1H); 4.56 (t, 1H); 3.72 (overlapping is and m, 4H); 2.61 (s, 3H); 2.52–2.30 (m, 5H); 1.85 (m, 1H); 1.78 (s, 3H); 1.21 (s, 3H); 1.12 (s, 3H); 1.10 (d, 3H); 0.93 (d, 3H); o.90 (s, 9H); 0.88 (s, 9H).

Compound 70

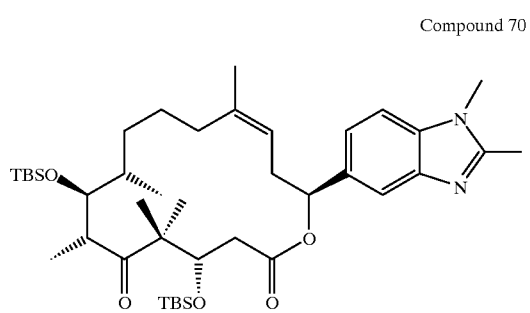

Compound 70 is prepared in analogy to 18 lactone 18; "alternative procedure") from 0.730 g of 69. Purification is effected by FC in CH₂Cl₂/acetone 9/1 to provide 70 as a white foam. ESI-MS: 727.1 (M+H). ¹H-NMR (CDCl₃, 400 MHz): δ (ppm vs. TMS)=7.70 (s, 1H); 7.25 ("m", 2H); 5.59 (d, 1H)); 5.25 (t, 1H); 3.95 (t, 1H); 3.90 (d, 1H); 3.72 (s, 3H); 3.10–290 (m, 2H); 2.60 (s, 3H); 2.15 (m, 1H); 1.78 (m, 2H); 1.62 (s, 3H); 1.00 (d, 3H); (0.98 (s, 9H); 0.85 (s, 9H).

Compound 71

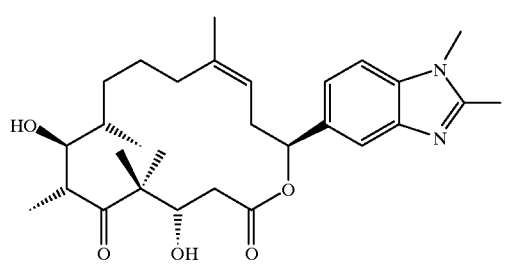

Compound 71 is prepared in analogy to 19 (lactone 19; "alternative procedure") from 0.290 g of 70. Purification is effected by FC in CH$_2$Cl$_2$)acetone 1/1 to provide 71 as a white crystalline solid. ESI-MS: 499.1 (M+H). $^1$H-NMR (CDCl$_3$, 400 MHz): δ (ppm vs. TMS)=7.70 (s, 1H); 7.23 (s, 2H); 5.93 (dd, 1H)); 5.23 (m, 1H); 4.20 (m, 1H); 3.75 (m, 1H); 3.72 (s, 3H); 3.18 (m, 1H); 2.92 (m, 1H); 2.60 (s, 3H); 2.42 (m, 2H); 2.30 (m, 2H); 1.90 (m, 1H); 1.75 (m, 2H); 1.68 (s, 3H); 1.35 (m, 3H); 1.28 (s, 3H); 1.21 (d, 2H); 1.03 (d, 3H); 1.01 (s, 3H).

Compound 72

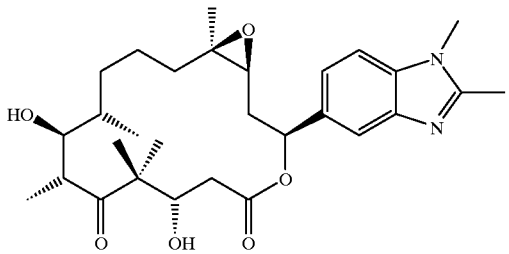

Compound 72 is prepared in analogy to 82 from 0.030 g of 71. Purification is effected by FC in 4% MeOH/CH$_2$Cl$_2$ and 3% MeOH/CH$_2$Cl$_2$ (2 runs) to provide 72 as a white solid.

ESI-MS: 515.2 (M+H). $^1$H-NMR (CDCl$_3$, 500 MHz): δ (ppm vs. TMS)=7.68 (s, 1H); 7.27 (s, 2H): 6.13 (m, 1H)): 5.23 (m, 1H); 4.08 (m, 1H); 3.80 (m, 1H); 3.73 (s, 3H); 3.47 (d, br, OH); 3.33 (m, 1H); 2.79 (dd, 1H); 2.54 (br, OH); 2.54 (dd, 1H); 2.38 (dd, 1H); 2.24 (dd, 1H); 2.14; (dd, 1H); 1.27 (s, 3H); 1.28 (s, 3H); 1.18 (d, 2H); 1.04 (overlapping s and d, 6H).

EXAMPLES 21/22—PRECURSORS

Compound 73

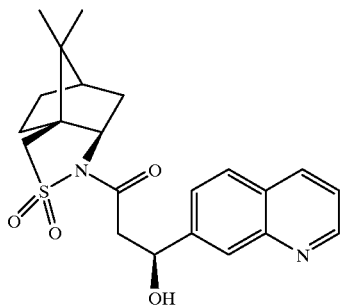

Compound 73 is prepared in analogy to alcohol 2 from 5.5 g of chinoline-7-carbaldehyde (prepared from 7-methyl chinoline (commercial form ACRO) according to W. D. Kingsburry et al., *J. Med. Chem.* 1993, 36, 3308–3320) and 6.43 g of sultam 1. Purification is effected by FC in CH$_2$Cl$_2$/MeOH 9/1 to provide a ca. 5/1 mixture of compound 73 and its R-diastereoisomer. ESI-MS: 415.1 (M+H). $^1$H-NMR (CDCl$_3$, 300 MHz, major isomer): δ (ppm vs. TMS)=8.91 (dd, 1H); 8.165 (d, 1H); 8.12 (s, 1H); 7.83 (d, 1H); 7.65 (d, 1H); 7.40 (dd, 1H); 5.42 (m, 1H); 3.90 (t, 1H); 3.75 (s, br); 3.48 (dd, 2H); 3.24 (m, 2H); 2.25–200 (m, 2H); 190; (m, 3H); 1.40 (m, 2H); 1.111 (s, 3H); 0.97 (s, 3H).

Compound 74

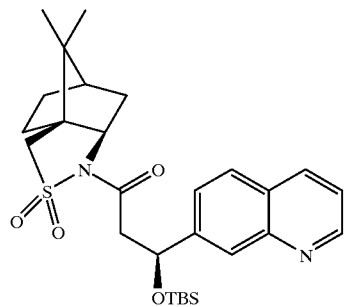

Compound 74 is prepared in analogy to TBS-ether 3 from 8.48 g of compound 73 (mixture of disteoroisomers, s. above) and 4.6 g of TBS-Cl, except that the reaction is conducted at 45° C. throughout. Purification is effected by repeated FC in AcOEt/hexane mixtures (2/3–1/2) to provide 63 as a single diastereoisomer. ESI-MS: 529.0 (M+H). $^1$H-NMR (CDCl$_3$, 300 MHz): δ (ppm vs. TMS)=8.90 (dd, 1H); 8.12 (d, 1H); 7.97 (s, 1H); 7.80 (d, 1H); 7.69 (d, 1H); 7.38 (dd, 1H); 5.45 (t, 1H); 3.80 (m, 1H); 3.37 (s, 2H); 3.19 (d, 2H); 200 (m, 1H); 1.83 (m, 3H); 1.69 (m, 1H); 0.86 (s, 9H); 0.83 (s, 3H); 0.52 (s, 3H).

Compound 75

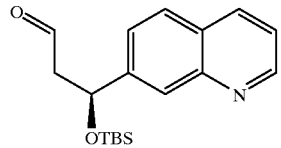

Compound 75 is prepared in analogy to aldehyde 4 from 4.0 g of compound 74 and 18 ml of a 1M DIBAL-H solution in CH$_2$Cl$_2$, except the reaction is quenched with water rather than MeOH and that the filtration step in the work-up can be omitted. Purification is effected by FC in AcOEt/hexane 1/1 to provide 75. ESI-MS: 348.2 (M+Na). $^1$H-NMR (CDCl$_3$, 300 MHZ): δ (ppm vs. TMS)=9.85 (s, 1H); 8.95 (d, 1H); 8.17 (d, 1H); 8.06 (s, 1H); 7.84 (d, 1H); 7.60; (d, 1H); 7.42 (dd, 1H); 5.45 (dd, 1H); 2.95 (m, 1H); 2.72 (dd, 1H); 0.89 (s, 9H); 0.10 (s, 3H); −0.10 (s, 3H).

Compound 76

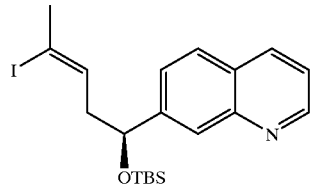

Compound 76 is prepared in analogy to vinyl iodide 5 from 1.86 g of compound 75 and 4.04 g of [Ph$_3$P-ChlCH$_3$]$^+$ I$^-$, except that stirring at. −78° C. after addition of NaHMDS to the suspension of [Ph$_3$PChlCH$_3$]$^+$I$^-$, is performed for 30 min and that the temperature is raised to −15° C. for 20 min before re-cooling to −78° C. and addition of the aldehyde. Purification is effected by FC in hexane/ether 1/1 to provide 76. ESI-MS: 453.9 (M+H). $^1$H-NMR (CDCl$_3$, 300 MHz): δ (ppm vs. TMS)=8.92 (dd, 1H); 8.17 (d, 1H); 8.03 (s, 1H); 7.81 (d, 1H); 7.61 (d, 1H); 7.40 (dd, 1H); 5.50 (t, 1H); 5.50 (t, 1H); 2.55 (m, 2H); 2.50 (s, 3H); 0.90 (s, 9H); 0.10 (s, 3H);

−0.08 (s, 3H).

Compound 77

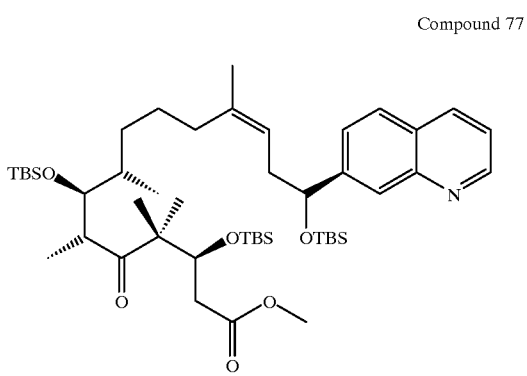

Compound 77 is prepared in analogy to compound 30 from 1.772 g of 96 and 1.104 g of compound 76. Purification is effected by FC in hexane/ether 3/2 to provide 77 as a orange-coloured oil. ESI-MS: 856.1 (M+H). $^1$H-NMR (DMSO-$d_6$, 400 MHz): δ (ppm vs. TMS)=8.85 (dd, 1H); 8.31 (d, 1H); 7.93 (d, 1H); 7.91 (s, 1H), 7.55 (d, 1H); 7.50 (dd, 1H); 5.16 (t, 1H); 4.89 (t, 1H); 4.22 (m, 1H); 3.62 (m, 1H); 3.10 (m, 1H); 2.35 (m, 2H); 2.15 (dd, 1H); 1.87 (m, 2H); 1.59 (s, 3H); 1.15 (s, 3H); 0.98 (s, 3H); 0.95 (d, 3H); 0.87 (s, 9H); 083 (s, 9H); 0.81 (s, 9H).

Compound 78

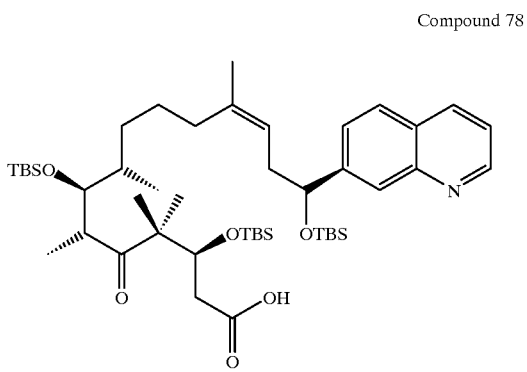

Compound 78 is prepared in analogy to compound 16 from 2.033 g of 77. Purification is effected by FC in 3% MeOH/CH$_2$Cl$_2$ to provide 78 as a light beige crystalline residue.

ESl-MS: 842.0 (M+H). $^1$H-NMR (DMSO-$d_6$, 400 MHz); δ (ppm vs. TMS)=8.85 (dd, 1H); 8.31 (d, 1H); 7.91 (d, 1H); 7.89 (s, 1H); 7.55 (d, 1H); 7.47 (dd, 1H); 5.16 (t, 1H); 4.87 (t, 1H); 4.20 (m, 1H); 3.62 (m, 1H); 3.13 (m, 1H); 2.35 (m, 2H); 2.28 (dd, 1H); 2.02 (dd, 1H); 1.87; (m, 2H); 1.59 (s, 3H); 1.13 (s, 3H); 0.97 (s, 3H); 0.95 (d, 3H); 0.85 (s, 9H); 0.81 (s, 9H); 0.79 (s, 9H).

Compound 79

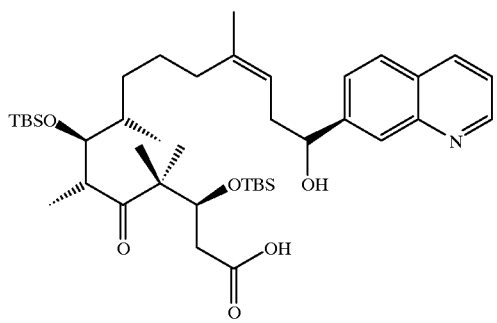

Compound 79 is prepared in analogy to hydroxy acid 17 from 1.35 g of 78, except that only 3 equiv. of TBAF are used. Purification is effected by FC in 6% MeOH/CH$_2$Cl$_2$ to provide 79 as a white foam. ESI-MS: 728.1 (M+H). $^1$H-NMR (DMSO-$d_6$, 500 MHz): δ (ppm vs. TMS)=8.85 (dd, 1H); 8.29 (d, 1H); 7.89 (s, 1H); 7.87 (d, 1H); 7.55 (dd, 1H); 7.46 (dd, 1H); 5.20 (t, 1H); 4.70 (t, 1H); 4.18 (dd, 1H); 3.61 (dd, 1H); 3.11 (m, 1H); 2.37 (m, 2H); 2.28 (dd, 1H); 2.03 (dd, 1H); 1.85 (m, 2H); 1.58 (s, 3H); 1.11 (s, 3H); 0.95 (s, 3H); 0.93 (d, 3H); 0.82 (s, 9H); 0.78 (d, 3H); 0.77 (s, 9H).

Compound 80

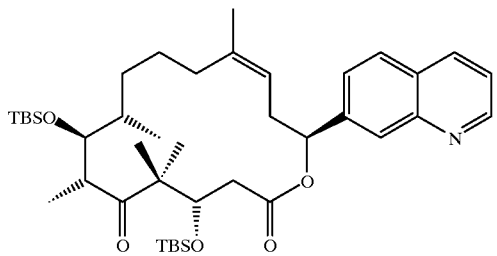

Compound 80 is prepared in analogy to 18 (lactone 18; "alterative procedure") from 0.826 g of 79. Purification is effected by FC in AcOEt/hexane 1/4 to provide 0.45 g of 80 as a white amorphous powder. ESI-MS: 710.2 (M+H). $^1$H-NMR (CDCl$_3$, 400 MHz): δ (ppm vs. TMS)=8.92 (dd, 1H); 8.16 (d, 1H); 8.10 (s, 1H); 7.82 (d, 1H); 7.57 (d, 1H); (d, 1H); 7.41 (dd, 1H); 5.65 (d, 1H); 5.27 (t, 1H); 3.97 (dd, 1H); 3.91 (d, 1H); 3.05 (m, 1H); 2.94 (m, 1H); 2.37 (m, 2H); 2.80 (m, 2H); 2.62 (m, 1H); 2.20 (m, 1H); 1.80 (m, 2H); 1.73 (s, 3H); 1.17 (s, 3H); 1.13 (s, 3H); 1.10 (d, 3H); 1.00 (d, 3H); 0.98 (s, 9H); 0.83 (s, 9H).

Compound 81

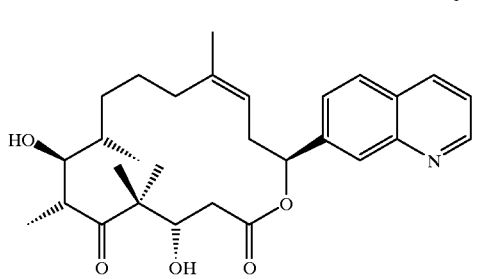

Compound 81 is prepared in analogy to 19 (lactone 19; "alternative procedure") from 0.567 g of 80. Purification is effected by FC in 2% MeOH/CH$_2$Cl$_2$ to provide 0.365 g of 81 as a white amorphous powder, which contained pyridine. Crystallization from CH$_2$Cl$_2$/hexane gives pure 81. ESI-MS: 482.2 (M+H). $^1$H-NMR (CDCl$_3$, 500 MHz): δ (ppm vs. TMS)=8.87 (dd, 1H); 8.18 (d, 1H); 8.15 (s, 1H); 7.82 (d, 1H); 7.51 (d, 1H); 7.41 (dd, 1H); 6.01 (d, 1H); 5.22 (t, 1H); 4.39 (d, 1H); 3.75 (s, br, 1H); 3.67 (s, H); 3.20 (dq, 1H); 3.03 (s, 1H); 2.28 (m, 1H); 2.51 (dd, 1H); 2.45–2.30 (m, 3H); 1.77 (m, 2H); 1.70 (s, 3H); 1.35 (s, 3H); 1.23 (d, 3H); 1.07 (s, 3H); 1.06 (d, 3H).

Compound 82

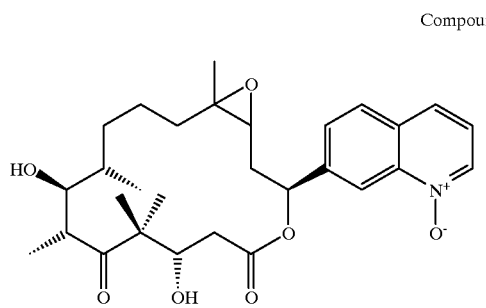

To a solution of 0.024 g of compound 82 in 0.250 ml of CH$_2$Cl$_2$ are added 0.075 ml of mixture of 6.84 ml of water, 0.760 ml of 30% H$_2$O$_2$ and 0.048 ml of pyridine (solution A), followed by 0.001 g of methyltrioxo rhenium. After 2 h at RT additional 0.075 ml of solution A and 0.001 g of methyltrioxo rhenium are added and stirring at RT is continued for 15 h. After addition of a few mg of MnO$_2$ the mixture is stirred for 1 h and 20 ml of water and CH$_2$Cl$_2$ each are then added. The organic layer is separated, dried over MgSO$_4$ and the solvent evaporated. FC in CH$_2$Cl$_2$/acetone 1/1 provides 82. ESI-MS: 514.3 (M+H). $^1$H-NMR (CDCl$_3$, 400 MHz): δ (ppm vs. TMS)=8.62 (s, 1H); 8.57 (d, 1H); 7.92 (d, 1H); (d, 1H); 7.87 (d, 1H); 7.59 (dd, 1H); 7.37 (dd, 1H);6.17 (d, 1H); 5.50 (d, 1H); 4.78 (d, 1H); 3.78 (m, 1H); 3.40 (m, 1H); 3.18 (s, br): 2.92 (dd, 1H); 2.55 (t, 1H); 2.40 (dd, 1H); 2.30 (dd, 1H); 2.05 (m, 1H); 1.82 (m, 2H); 1.50 (s, 3H); 1.33 (s, 3H); 1.1 (d, 3H); 1.05 (s, 3H); 1.02 (d, 3H).

Compound 83

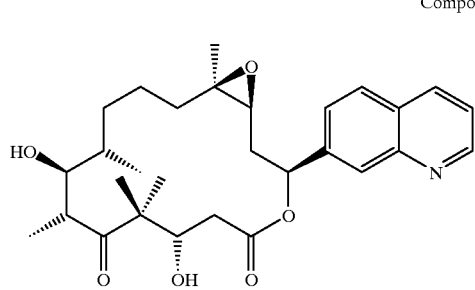

82 (0.0127 g) is hydrogenated over Ra-Ni in 2 ml of ETOH at RT and atmospheric pressure. After 70 min the catalyst is removed by filtration and the filtrate is evaporated. FC in CH$_2$Cl$_2$/acetone 3/1 gives 0.078 g of 83 as a white solid. ESI-MS: 498.1 (M+H). $^1$H-NMR (DMSO-d$_6$, 500 MHz): δ (ppm vs. TMS)=8.90 (dd, 1H); 8.34 (d, 1H); 8.07 (s, 1H); 7.96 (d, 1H); 7.70 (dd, 1H); 7.52 (d, 1H); 7.41 (dd, 1H); 6.03 (dd, 1H); 5.13 (d, 1H); 4.50 (d, 1H); 4.16 (m, 1H); 3.51 (t, 1H); 3.20 (m, 1H); 2.97 (dd, 1H); 2.49 (m, 1H); 2.40 (dd, 1H); 2.20 (m, 1H); 2.09 (m0, 1H); 1.22 (s, 3H); 1.16 (s, 3H); 1.07 (d, 3H); 0.93 (d, 3H); 0.90 (s, 3H).

The (α,β-unsaturated lactones of the compounds of examples 1 to 34 can be produced in a 3-stage process starting with, the above-described compounds:

1. Bis-formylation of the free OH groups at C-3 and C-7 with the aid of the mixed anhydride of formic acid and acetic acid (where present, also simultaneous formylation of further hydroxy groups, such as the 21-hydroxymethyl group).
2. Treatment of the bis-formyl derivative with DBU (1,8-diazabicyclo[2.2.2]undec-7-en (1,5-5)) in dichloroethane, which leads to elimination of formic acid and the formation of a double bond between C-2 and C-3.
3. Removal of the formyl protecting group from the OH-group at C-7 and optionally of further hydroxy groups with NH$_3$/methanol.

In this way, the corresponding compounds of formula (A) are obtained from the compounds of examples 1, 2, 5, 7, 9, 11, 13, 15, 17, 19, 21, 23, 25, 27, 29, 31 and 33

(A)

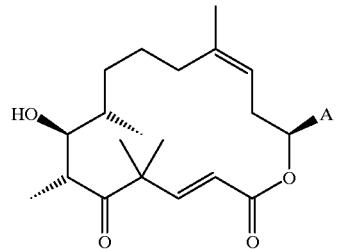

(the following examples with d numbers);
or the corresponding compounds of formula (B) are obtained from the compounds of examples 3, 4, 6, 8, 10, 12, 14, 16, 18, 20, 22, 24, 26, 28, 30, 32 and 34

(B)

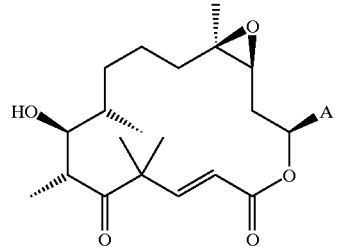

(the following examples with numbers)
wherein A respectively has the following meanings:

| Example | —A |
|---|---|
| 35, 36 | 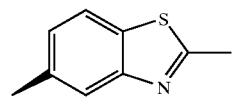 |

-continued

| Example | A |
|---|---|
| 37, 38 | 2-methylbenzothiazol-6-yl |
| 39, 40 | 2-methylbenzoxazol-4-yl |
| 41, 42 | 2-methylbenzoxazol-6-yl |
| 43, 44 | benzothiazol-5-yl |
| 45, 46 | benzothiazol-6-yl |
| 47, 48 | 1H-benzimidazol-5-yl |
| 49, 50 | 1-methylbenzimidazol-5-yl |
| 51, 52 | 1,2-dimethylbenzimidazol-5-yl |
| 53, 54 | 3-methylbenzimidazol-5-yl |
| 55, 56 | quinolin-7-yl |
| 57, 58 | 2-methylquinolin-7-yl |
| 59, 60 | 4-methylquinolin-7-yl |
| 61, 62 | quinolin-6-yl |
| 63, 64 | 2-methylquinolin-6-yl |
| 65, 66 | 2-(hydroxymethyl)benzothiazol-5-yl |
| 67, 68 | 2-(fluoromethyl)benzothiazol-5-yl |

The following examples are produced analogously to the above examples, methods and processes:

| Example | Compound |
|---|---|
| 69 | (epothilone analog with 2-(hydroxymethyl)benzoxazol-5-yl side chain) |
| 70 | (epoxide epothilone analog with 2-(hydroxymethyl)benzoxazol-5-yl side chain) |
| 71 | (epothilone analog with 2-(aminomethyl)benzoxazol-5-yl side chain) |

-continued
| Example | Compound |
|---|---|
| 72 | 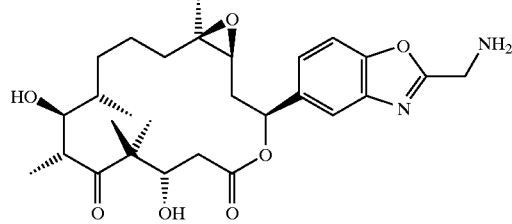 |
| 73 | 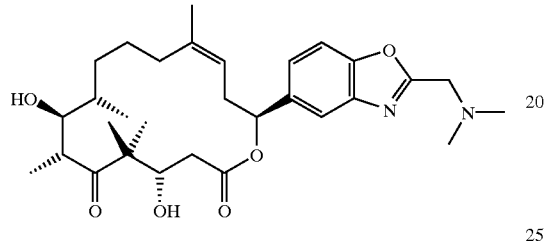 |
| 74 | 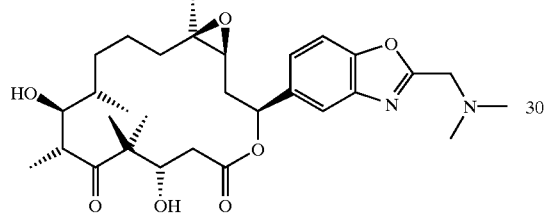 |
| 75 | 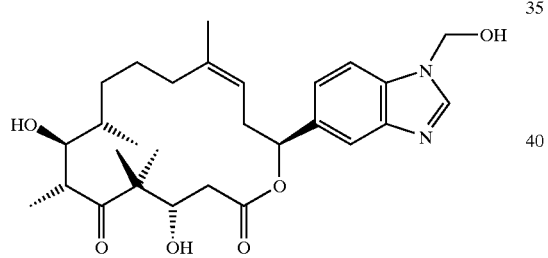 |
| 76 | 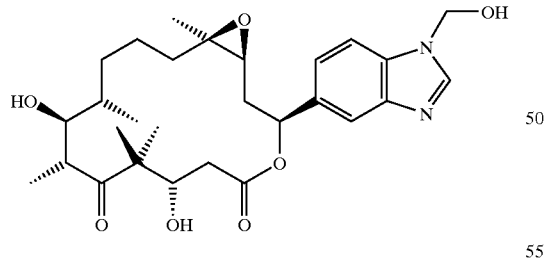 |
| 77 | 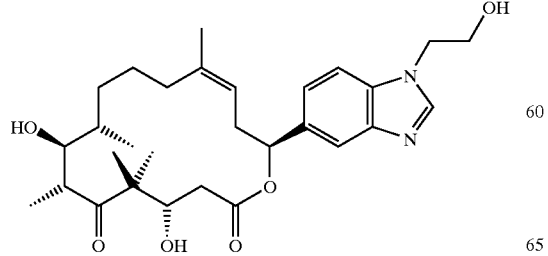 |
-continued
| Example | Compound |
|---|---|
| 78 | 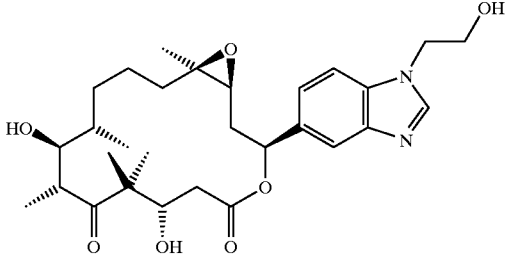 |
| 79 | 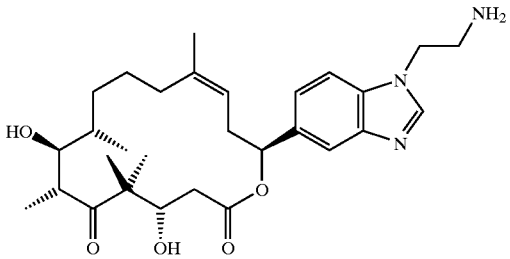 |
| 80 | 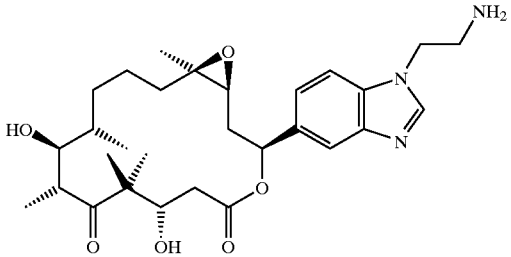 |
| 81 | 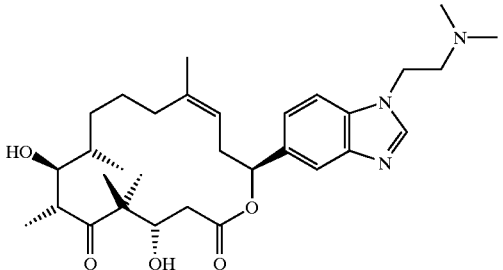 |
| 82 | 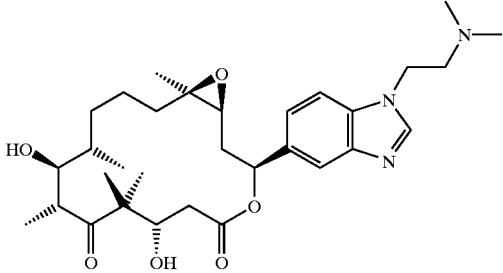 |

-continued
| Example | Compound |
|---|---|
| 83 | 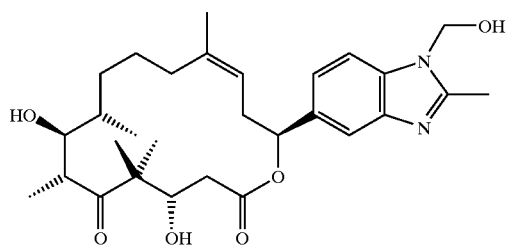 |
| 84 | 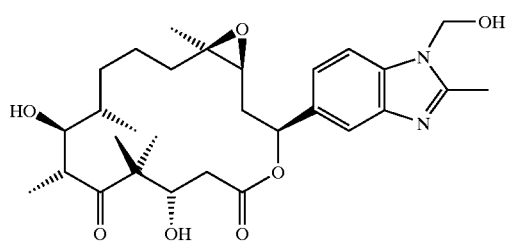 |
| 85 | 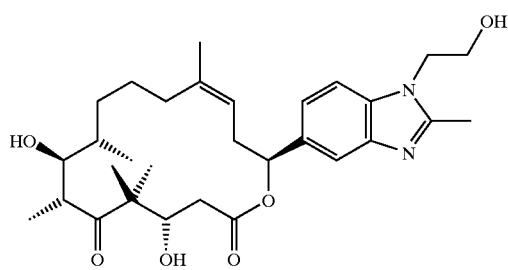 |
| 86 | 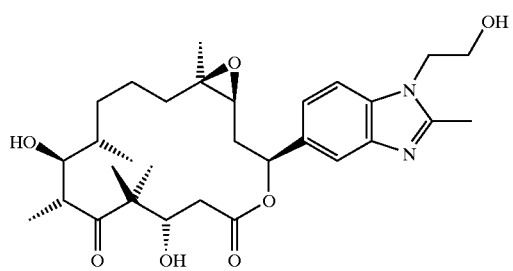 |
| 87 | 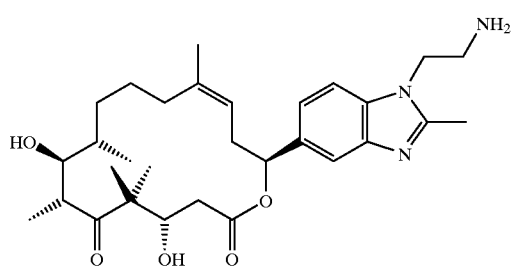 |
-continued
| Example | Compound |
|---|---|
| 88 | 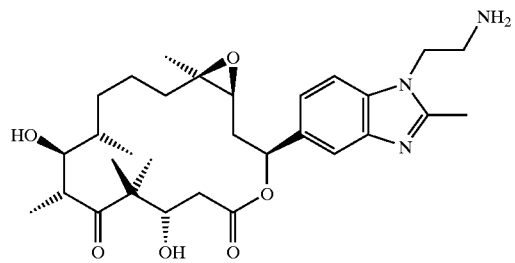 |
| 89 | 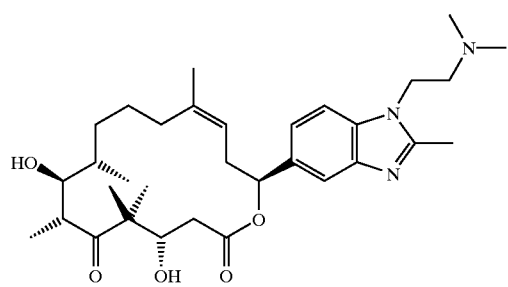 |
| 90 | 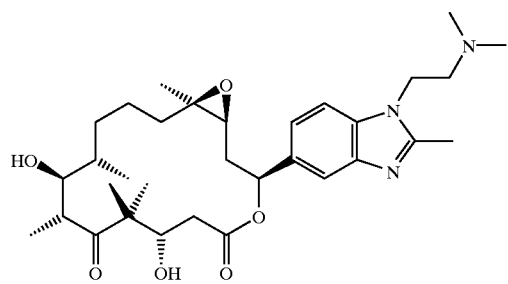 |
| 91 | 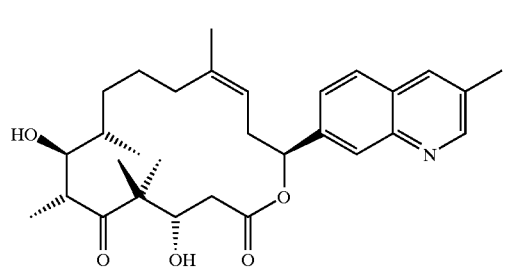 |
| 92 | 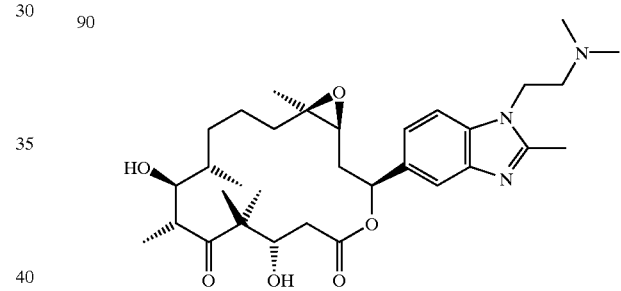 |

-continued

| Example | Compound |
|---|---|
| 93 | 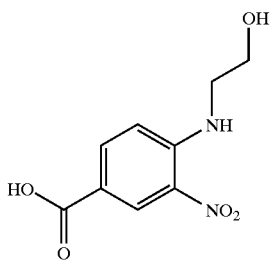 |
| 94 | |
| 95 | |
| 96 | |

PRECURSORS FOR EXAMPLES 77 to 83

Compound 84

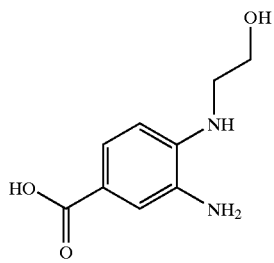

A solution of 14.5 g of 4-fluoro-3-nitro-benzoic acid and 94 ml of ethanolamine in 435 ml of EtOH is stirred at RT for 4 h. The mixture is then evaporated to dryness, 500 ml of water are added to the residue, and the pH adjusted to ca. 4 with 1N HCl. the resulting precipitate is isolated by filtration, washed with 200 ml of water, and dried in vacuo to give 84 as a yellow powder. M.p. 211–212° C. ESI-MS (negative mode): 225.2 (M−H). $^1$H-NMR (DMSO-$d_6$, 400 MHz); δ (ppm vs. TMS)=8.60 (s, 1H); 8.58 (t, 1H); 7.94 (d, 1H); 7.14 (d, 1H); 3.65 (t, 2H); 3.45 (q, 2H).

Compound 85

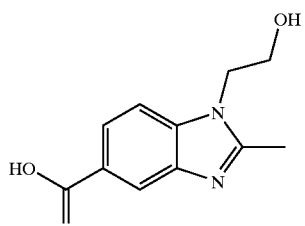

Compound 84 (17.94 g) is hydrogenated over Ra-Ni in EtOH/THF 1/2 at RT and atmospheric pressure. After 17 h the[1] catalyst is removed by filtration and extensively washed with THF/EtOH 2/1 (ca. 1 L). The filtrate is evaporated to dryness and the residue triturated with 200 ml of ether for 30 min. Filtration gives 85 as a grey powder M.p. 210–220° C. (dec.).

ESI-MS: 197.1 (M+H). $^1$H-NMR (DMSO-$d_6$, 400 MHz): δ (ppm vs. TMS)=7.18 (d, 1H); 7.13; (s, 1H); 6.41 (d, 1H); 5.10 (s, br, 1H); 3.59 (t, 2H); 3.18 (m, 2H).

Compound 86

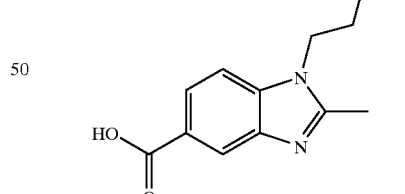

A solution of 14.5 g of compound 85 and 34 ml triethyl-orthoacetate in 170 ml of EtOH is heated to reflux for 4 h. After cooling to RT the product is isolated by filtration, washed with 30 ml of EtOH and dried in vacuo to give 86 as a white powder). M.p. 267–270° C. (dec.). ESI-MS (negative mode): 219.2 (M−H). $^1$H-NMR (DMSO-d6, 400 MHz): δ (ppm vs. TMS)=8.07 (s, 1H); 7.79 (d, 1H); 7.55 (d, 1H); 4.23 (t, 2H); 3.70 (m, 2H); 2.57 (s, 3H).

Compound 87

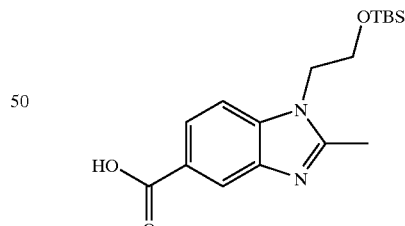

To a solution of 8.5 g of compound 86 in 120 ml of DMF are added 6.57 g of TBS-Cl and 5.78 g of imidazole and the mixture is stirred at 45° C. for 18 h. At this point additional imidazole (1.73 g) and TBS-Cl (1.97 g) are added and stirring continued at the same temperature for 6 more hours. Additional imidazole (1.16 g) and TBS-Cl (1.31 g) are then added and stirring continued for 18 more hours. The reaction mixture is then evaporated to dryness in vacuo and 300 ml of AcOEt and 500 ml of a 5% KHSO$_4$ solution are added to the residue. Insoluble material is isolated by filtration, washed with AcOEt and water and dried in vacuo to provide.

The layers of the combined filtrates are then separated and the aqueous solution is twice extracted with 300 ml of AcOEt each. The combined organic extracts are washed with 100ml of water, dried over $MgSO_4$, and the solvent evaporated to give a ca. 4/1 mixture of the desired acid and its TBS-ester. From the combined aqueous extracts additional 87 precipitates after the extraction and is isolated by filtration. The above mixture of acid and TBS-ester is dissolved in 100 ml of MeOH, 1.38 of $K_2CO_3$ are added and the mixture is stirred at RT for 3 h. It is then evaporated to dryness and 20 ml of AcOEt and 150 ml of water are added to the residue. Addition of 2.3 ml of AcOH and isolation of the precipitate by filtration provides additional 87 as a white powder. M.p. 218–219° C. ESI-MS (negative mode): 333.3 (M–H). $^1$H-NMR ($CD_3OD$, 400 MHz): δ (ppm vs. TMS)= 8.25 (s, 1H); 7.95 (d, 1H); 7.55 (d, 1H); 4.41 (t, 2H); 4.00 (t, 2H); 2.65 (s, 3H); 0.85 (s, 9H); –0.3 (s, 6H).

PREPARATION OF KEY INTERMEDIATE 96— ROUTE 1

Compound 107

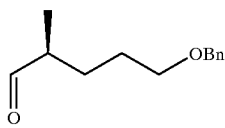

To a solution of 10.71 g of oxalyl chloride in 170 ml of $CH_2Cl_2$ is added a solution of 13.19 g of DMSO in 15 ml of $CH_2Cl_2$ at –78° C. over a period of 15 min. The solution is stirred at this temperature for 15 min, when a solution of 8.79 g of compound KH-1952 (cf. Schinzer et al. *Synlett* 1998, 861–864) in 35 ml of $CH_2Cl_2$ is added dropwise over a 15 min period. The mixture is stirred at –78° C. for 45 min and then 25.62 g of $Et_3N$ are added dropwise at the same temperature over a period of 15 min. The cooling bath is removed and the mixture allowed to warm to RT (suspension). It is then re-cooled to –30° C. and 110 ml of sat. aqu. $NH_4Cl$ are added. Subsequently water is added at RT until a clear biphasic solution has formed, and the layers are separated. The organic solution is washed with 75 ml of 2% $KHSO_4$, 75 ml of sat. $NaHCO_3$, and 75 ml of brine, dried over $MgSO_4$, and the solvent is evaporated. The residue is purified by FC with AcOEt/hexane 3/7 as eluent to give 107 as an oil. ESI-MS: 207 (M+H). $^1$H-NMR ($CDCl_3$, 300 MHz): δ (ppm vs. TMS)=9.62 (d, 1H); 7.32 (m, 5H); 4,50 (s, 2H); 3.50 (t, 2H); 2.35 (m, 1H); 1.82 (m, 1H); 1.65 (m, 2H); 1.60 (m, 1H); 1.11 (d, 3H).

Compound 109

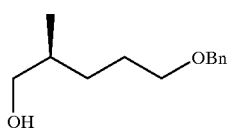

Compound 88

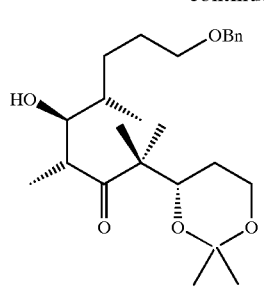

To a solution of 9.6 ml of $(i-C_3H_7)_2NH$ in 100 ml of THF are added dropwise 42.46 ml a 1.6 M solution of n-BuLi in hexane at –5° C. –0° C. over a period of 10 min. The yellow solution is stirred at 0° C. for 30 min, cooled to –78° C., and a solution of 14.83 g of 108 (cf. Schinzer et al. *Chem. Eur. J.* 1996, 2, 1477–1481) in 100 ml of THF is added dropwise at the same temperature within 20 min. After 1 additional hour at –78° C. a solution of 107 in 125 ml of THF is added dropwise over i5 min. The mixture is then stirred at –78° C. for 1 h, when 150 ml of sat. aqu. $NH_4Cl$ are added. The mixture is then allowed to warm to RT and 600 ml of ether are added followed by water until a clear biphasic solution has formed. The layers are separated and the aqueous solution is twice extracted with 600 ml of ether. The combined organic extracts are dried over $MgSO_4$ and the solvent is evaporated. Purification of the residue by FC in hexane/AcOEt 3/2 (three runs) gives 88 as a single diastereoisomer (by NMR). ESI-MS: 421.4 (M+H). $^1$H-NMR ($CDCl_3$, 300 MHz): δ (ppm vs. TMS)=7.32 (m, 5H); 4.50 (s, 2H); 4.20–3.80 (m, 3H); 3.55–3.25 (m, 5H); 1.40 (s, 3H); 1.32 (s, 3H); 1.20 (s, 3H); 1.09 (s, 3H); 1.02 (d, 3H); 0.88 (d, 3H).

Compound 108

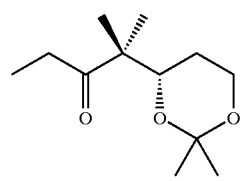

Compound 89

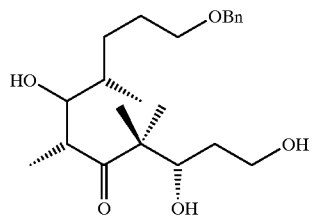

To a solution of 11.96 g of compound 88 in 360 ml of MeOH are added 7.15 g of pyridinium-p-toluene sulfonate and the mixture is stirred at RT for 24 h. The solvent is then evaporated and the residue purified by FC in ether to provide 89. ESI-MS: 403.0 (M+Na). $^1$H-NMR ($CDCl_3$, 300 MHz): δ (ppm vs. TMS)=7.32 (m, 5H); 4.50 (s, 2H); 4.03 (m, 1H); 3.85 (m, 2H); 3.49 (m, 2H); 3.32 (m, 4H); 1.20 (s, 3H); 1.15 (s, 3H); 1.07 (d, 3H); 0.88 (d, 3H).

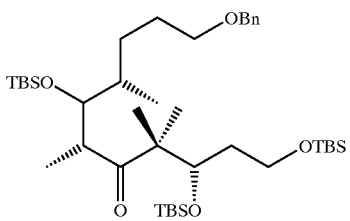

Compound 90

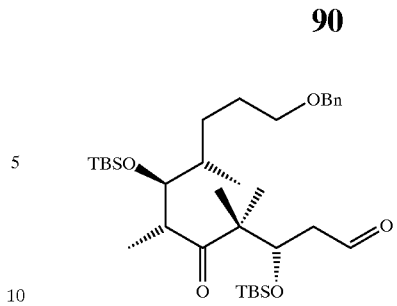

Compound 92

To a solution of 8.75 g of compound 89 in 300 ml of CH$_2$Cl$_2$ are added 12.3 g of 2,6-lutidine followed by dropwise addition of 24.3 g of TBS-OTf at a temperature between 0° C. and 5° C. over 10 min. The mixture is stirred at RT for 20 h, concentrated to about 50% of its original volume and then poured on a mixture of 800 ml of AcOEt and 500 ml of sat. aqu. NaHCO$_3$. The layers are separated and the aqueous solution is extracted with 300 ml of AcOEt. The combined organic extracts are then successively washed with water, 5% KHSO$_4$ (2×), brine (2×), and water. After drying over MgSO$_4$ and evaporation of solvent the residue is purified by FC in 30% hexane/ether to provide the title compound.

ESI-MS: 723.0 (M+H). $^1$H-NMR (CDCl$_3$, 500 MHz): δ (ppm vs. TMS)=7.32 (m, 4H); 7.28; (m, 1H); 4.50 (s, 2H); 3.89 (dd, 1H); 3.78 (dd, 1H); 3.66 (m, 1H); 3.58 (m, 1H); 3.46 (t, 2H); 3.15 (m, 1H); 1.22 (s, 3H); 1.05 (d, 3H); 1.02 (s, 3H); 0.94 (d, 3H).

To a solution of 1.5 of oxalyl chloride in 45 ml of CH$_2$Cl$_2$ are added 2.7 ml of DMSO at −75° C. over a period of 5 min. The solution is stirred at this temperature for 10 min, when a solution of 9.25 g of compound 91 in 45 ml of CH$_2$Cl$_2$ is added dropwise over a 20 min period. The mixture is stirred at −75° C. for 30 min and then 12.0 ml of ETSN are added dropwise at the same temperature over a period of 10 min. The mixture is allowed to warm to −10° C., followed by addition of 200 ml of water and 300 ml of CH$_2$Cl$_2$. The layers are separated and the organic solution is twice washed with 300 ml of brine. The combined aqueous extracts are once re-extracted with 200 ml of CH$_2$Cl$_2$. Drying of the combined organic extracts over MgSO$_4$, evaporation of solvent and purification of the residue by FC in hexane/ether 4/1 gives 92. E SI-MS: 607.3 (M+H). $^1$H-NMR (CDCl$_3$, 300 MHz): δ (ppm vs. TMS)=7.30 (m, 5H); 4.50 (overlapping s and m, 3H); 3.79 (d, 1H); 3.47 (t, 2H); 3.12 (m, 1H); 2.50 (dd, 1H); 2.40 (dd, 3H); 1.72 (m, 1H); 1.22 (s, 3H); 1.08 (s, 3H); 1.05 (d, 3H); 0.93 (d, 3H); 0.90 (s, 9H); 0.88 (s, 6H).

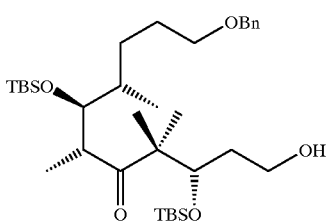

Compound 91

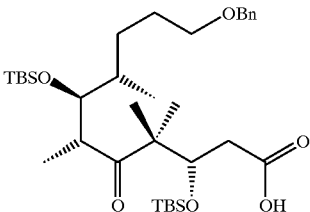

Compound 93

To a solution of 12.8 g of compound 90 in 700 ml of CH$_2$Cl$_2$/MeOH 1/1 at 0° C. are added 4.18 g of camphorsulfonic acid portionwise over 5 min. The mixture is stirred at 0° C. for 1 h, when 2.5 ml of Et$_3$N are added. The bulk of the CH$_2$Cl$_2$ is then removed by rotary evaporation and 300 ml of AcOEt are added to the remaining solution. This is followed by removal of the bulk of MeOH by rotary evaporation (no heating) and subsequent addition of an additional 200 ml of AcOEt. This solution is extracted with 400 ml of sat. aqu. NaHCO$_3$ and water (2×) and the combined aqueous extracts are once re-extracted with 300 ml of CH$_2$Cl$_2$. The CH$_2$Cl$_2$ solution is washed several times with 100 ml portions of water. The organic extracts are then combined, tried over MgSO$_4$ and the solvents evaporated. Purification of the residue by FC in hexane/ether 2/1 gives 91. ESI-MS: 631.3 (M+Na). $^1$H-NMR (DMSO-d$_6$, 500 MHz): δ (ppm vs. TM;)=7.30 (m, 5H); 4.42 (s, 2H); 4.38 (t, 1H); 3.79 (dd, 1H); 3.68 (m, 1H); 3.46 (m, 1H); 3.39 (t, 2H); 3.35 (m, 1H); 3.17 (m, 1H); 1.62 (m, 1H); 1.48 (m, 2H); 1.32 (m, 3H); 1.15 (s, 3H); 0.98 (d, 3H); 0.97 (s, 3H).

To a solution of ca. 7 g of iso-butene in 40 ml of THF at 0° C. is added a solution of 8.5 g of 92 in 70 ml of tert.-butanol dropwise over a period of 15 min followed by the dropwise addition of 14 ml of water at the same temperature. 4.8 g of NaClO$_2$ (80%) and 2.9 g of NaH$_2$PO$_4$xH$_2$O are then added and the mixture is stirred at RT for 4 h. The reaction mixture is then evaporated to dryness, the residue distributed between water and CH$_2$Cl$_2$ (500 ml each) and the layers are separated. The pH of the aqueous solution is adjusted to 4.5 with 1N HCl and it is then recombined with the CH$_2$Cl$_2$ extract. After extraction the layers are again separated and the aqueous solution is twice extracted with 250 ml of CH$_2$Cl$_2$ each. The combined organic extracts are washed with 400 ml of water, dried, and the solvent is evaporated. Purification of the residue by FC with hexane/acetone 1/1 as eluent gives 93 as an oil. ESI-MS (negative mode): 621.5 (M−H). $^1$H-NMR (CDCl$_3$, 300 MHz): δ (ppm vs. TMS)=7.30 (m, 5H); 4.50 (s, 2H); 4.39 (m, 1H); 3.80 (d, 1H); 3.45 (m, 2H); 3.15 (m, 1H); 2.48 (dd, 1H); 2.31 (dd, 1H); 1.72 (m, 1H); 1.21 (s, 3H); 1.10 (s, 3H); 1.06 (d, 3H); 0.92 (d, 3H); 0.90 (s, 9H); 0.88 (s, 9H).

Compound 94

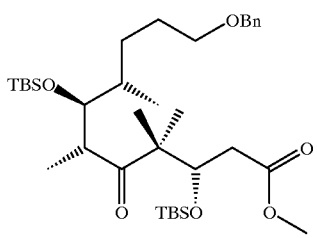

To a solution of 3.27 g of 93 in 90 ml of $CH_2Cl_2$, cooled to −20° C., and 1.2 of dicyclohexyl carbodiimide, 3.5 ml of MeOH, and 0.647 mg of dimethylamino pyridine are added. The mixture is allowed to warm to RT and after 4.5 h it is diluted with 400 ml of $CH_2Cl_2$. This solution is twice extracted with 200 ml of water each and the combined aqueous extracts are twice re-extracted with $CH_2Cl_2$. The combined organic extracts are dried over $MgSO_4$, the solvent evaporated and the residue purified by FC in hexane/ether 9/1 to provide 94. ESI-MS: 659.2 (M+Na). $^1$H-NMR ($CDCl_3$, 300 MHz): δ (ppm vs. TMS)=7.30 (m, 5H); 4.50 (s, 2H); 4.40 (m, 1H); 3.80 (d, 1H); 3.67 (s, 3H); 3.47 (m, 2H); 3.15 (m, 1H); 2.42 (dd, 1H); 2.28 (dd, 1H); 1.72 (m, 1H); 1.20 (s, 3H); 1.06 (s, 3H); 1.05 (d, 3H); 0.91 (d, 3H); 0.89 (s, 9H); 0.87 (s, 9H).

Compound 95

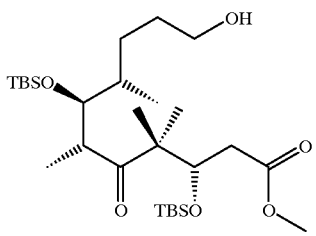

94 (1.25 g) is hydrogenated over 150 mg 5% Pd-C in 50 ml of MeOH at RT and atmospheric pressure. After 4 h the catalyst is removed by filtration, the filtrate evaporated and the residue purified by FC in hexane/ether 1/1 to give 95 as an oil. ESI-MS: 569.3 (M+Na). $^1$H-NMR ($CDCl_3$, 300 MHz): δ (ppm vs. TMS)=4.41 (m, 1H); 3.80 (dd, 1H); 3.68 (s, 3H); 3.64 (m, 2H); 3.17 (m, 1H); 2.43 (dd, 1H); 2.29 (dd, 1H); 1.22 (s, 3H); 1.10 (s, 3H); 1.07 (d, 3H); 0.95 (d, 3H); 0.91 (s, 9H); 0.88 (s, 9H).

Compound 96

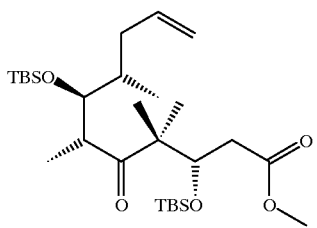

To solution of 5.0 g of 95 and 6.44 g of 2-nitrophenylseleno cyanate in 50 ml of THF are added 7.13 ml of tributyl phosphine dropwise over a period of 15 min such that the temperature does not exceed 35° C. The mixture is stirred at RT for 1 h at which point 23 g of solid $NaHCO_3$ are added followed by dropwise addition of 31.2 ml of 30% aqu. $H_2O_2$, again such that the temperature did not exceed 35° C. After 16 h at RT 185 ml of 5% $KHSO_4$ are added to the reaction mixture, which is then twice extracted with 400 ml of ether each. The combined organic extracts are washed with 200 ml of water, dried over $MgSO_4$, and the solvent is evaporated. Purification of the residue by FC in hexane/AcOEt 95/5 gives 96 as a yellow oil. ESI-MS: 529.1 (M+H). $^1$H-NMR ($CDCl_3$, 300 MHz): δ (ppm. vs. TMS)=5.73 (m, 1H); 5.02 (d, 1H); 4.98 (s, 1H); 4.41 (m, 1H); 3.81 (d, 1H); 3.68 (s, 3H); 3.17 (m, 1H); 2.43 (dd, 1H); 2.29 (dd, 1H); 1.85 (m, 1H); 1.40 (m, 1H); 1.26 (s, 3H); 1.10 (s, 3H); 1.08 (d, 3H); 0.96 (overlapping d and s, 12H); 0.94 (s, 9H).

PREPARATION OF KEY INTERMEDIATE 96—
ROUTE 2

Compound 97

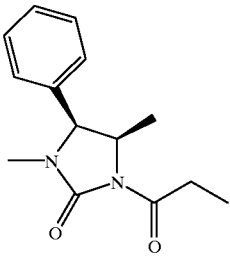

To a solution of 46.70 g of (4S, 5R)-1,4-Dimethyl-5-phenyl-imidazolidin-2-one (ALDRICH) in 450 ml of THF are added 162 ml of a 1.6 M solution of n-BuLi in hexane at −78° C. and the mixture is stirred for 1 h at this temperature. Propionylchloride (24.99 g) is then added to the solution and the mixture is allowed to warm to RT over night. After addition of 150 ml of 1N NaOH the layers are separated and the organic solution is washed with 1N NaOH and saline. Drying over $MgSO_4$ and evaporation of solvent gives crude 97, which is recrystallized from AcOEt to give pure 97 as white crystals. M.p. 104–106° C. ESI-MS: 247.1 (M+H).

Compound 98

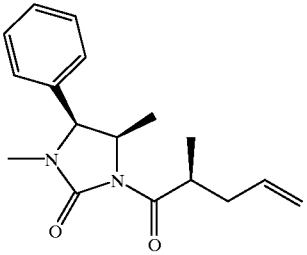

To a solution of 16.93 g of (i-$C_3H_7$)$_2$NH in 100 ml of THF are added dropwise 104 ml a 1.6 M solution of n-BuLi in hexane at 0° C. The solution is stirred at 0° C. for 10 min, cooled to −78° C., and a solution of 41.36 g of 97 in 150 ml of THF is added dropwise at the same temperature. After 3 additional hours at −78° C. 28.9 g of allyl iodide and 150 ml of THF are added. The mixture is then stirred overnight at −78° C. and poured into when 200 ml of 2N HCl. After stirring for 45 min the layers are separated and the aqueous solution is twice extracted with 150 ml ether. The combined organic extracts are washed with saline dried over $MgSO_4$ and the solvent is evaporated. Flash filtration with hexane/

AcOEt 1/1 gives a solid residue, whose recrystallization from hexane (2×) gives 98 as a single diastereoisomer (white crystals). M.p. 58–61° C. ESI-MS: 287.2 (M+H).

Compound 99

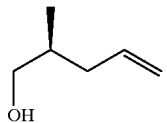

To a suspension of 27.90 g of 98 in 400 ml THF are added 6.20 g of LiAlH$_4$ and the mixture is stirred at 0° C. for 1 h. WHAT??? is then added, the solid material is removed by filtration, and the solvent evaporated. FC in hexane/ether 7/3 gives crude 99 (contains still solvent; evaporation of solvents after FC is carried out at a pressure above 500 mbar, in order to avoid loss of product). $^1$H-NMR (CDCl$_3$, 300 MHz): δ (ppm vs. TMS)=5.80 (m, 1H); 5.01 (m, 2H); 3.48 (m, 2H); 2.16 (m, 1H); 1.93 (m, 1H); 1,72 (m, 1H); 0.91 (d, 3H).

Compound 100

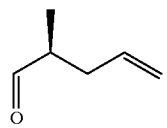

Compound 100 is obtained in analogy to 107 from 14.22 g of crude 99 (s. above). FC in pentane/ether 9/1 gives crude 100 (ca. 70%; contains still solvent), which is directly used in the next step (evaporation of solvents after FC was carried out at a pressure above 500 mbar, in order to avoid loss of product).).

$^1$H-NMR (CDCl$_3$, 300 MHz): δ (ppm vs. TMS)=9.65 (s, 1H); 5.73 (m, 1H); 5.10 (dd, 1H); 5.05 (s, 1H); 2.43 (m, 2H); 2.15 (m, 1H); 1.10 (d, 3H).

Compound 101

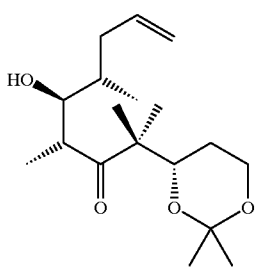

Compound 101 is prepared in analogy to compound 88 from 14.67 g of 108 and 3.36 g of KH-2115. Purification is effected by FC in 5% ether/CH$_2$Cl$_2$ and 2.5% ether/CH$_2$Cl$_2$ (3 runs) to provide 101 as an oil. ESI-MS: 313.3 (M+H). $^1$H-NMR (DMSO-d$_6$, 500 MHz): δ (ppm vs. TMS)=5.73 (m, 1H); 4.98 (s, 1H); 4.96 (m, 1H); 4.27 (d, 1H); 4.13 (dd, 1H); 3.89 (dt, 1H); 3.72 (dd, 1H); 3.53 (m, 1H); 3.46 (m, 1H); 3.40 (m, 1H); 3.16 (m, 1H); 2.30 (m, 1H); 1.76 (m, 1H); 1.41 (m, 2H); 1.29 (m, 2H); 1.00 (s, 6H); 0.95 (d, 3H); 0.80 (d, 3H).

Compound 102

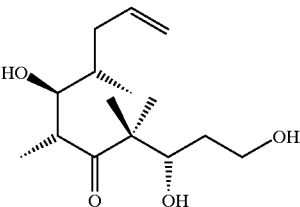

Compound 102 is prepared in analogy to compound 89 from 7.732 g of 101. Purification is effected by FC in 1% MeOH/CH$_2$Cl$_2$→10% MeOH/CH$_2$Cl$_2$ to provide 102 as an oil. ESI-MS: 252 (M−OH). $^1$H-NMR (DMSO-d$_6$, 500 MHz): δ (ppm vs. TMS)=5.72 (m, 1H); 4.98 (s, 1H); 4.95 (m, 1H); 4.58 (d, 1H); 4.38 (t, 1H); 4.25 (d, 1H); 3.74 (dd, 1H); 2.29 (m, 1H); 1.79 (m, 1H); 1.35 (s, 3H); 1.19 (s, 3H); 1.03 (s, 3H); 1.02 (s, 3H), 0.94 (d, 3H); 0.81 (d, 3H).

Compound 103

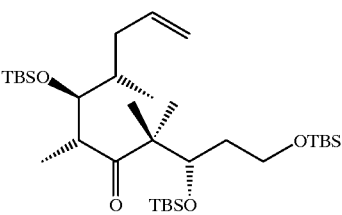

Compound 103 is prepared in analogy to compound 90 from 6.373 g of 102 and 20.8 ml of TBS-OTF. The crude product obtained after extraction is directly used in the next step. ESI-MS: 615.1 (M+H). $^1$H-NMR (CDCl$_3$, 500 MHz): δ (ppm vs. TMS)=5.73 (m, 1H); 4.98 (m, 2H); 3.90 (dd, 1H); 3.82 (dd, 1H): 3.68 (m, 1H): 3.58 (m, 1H); 3.37 (m, 1H); 2.24 (m, 1H); 1.85 (m, 1H); 1.23 (s, 3H); 1.07 (d, 3H); 1.05 (s, 3H).

Compound 104

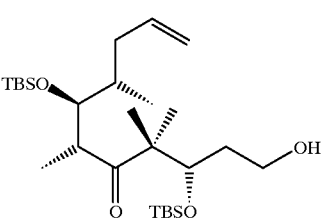

Compound 104 is prepared in analogy to compound 91 from 13.824 g of crude of 103 and 5.221 g of camphorsulfonic acid. Purification is effected by FC in hexane/ether 3/1 to pro vide 104 as a light yellow resin. ESI-MS: 483.1 (M−OH). $^1$H-NMR (DMSO-d$_6$, 500 MHz): δ (ppm vs. TMS)=5.72 (m, 1H); 4.98 (m, 2H); 4.39 (t, 1H); 3.82 (dd, 1H); 3.72 (dd, 1H); 3.45 (m, 1H); 3.34 (m, 1H); 3.22 (m, 1H); 2.24 (m, 1H); 1.79 (m, 1H); 1.49 (m, 1H); 1.41 (m, 1H); 1.33 (m, 1H); 1.17 (s, 3H); 0.98 (overlapping s and d, 6H).

Compound 105

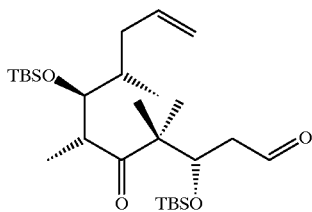

Compound 105 is prepared in analogy to compound 92 from 8.445 g of 104. The crude product obtained after extraction is directly used in the next step. ESI-MS: 499.0 (M+H). $^1$H-NMR (CDCl$_3$, 500 MHz): δ (ppm vs. TMS)= 9.77 (t, 1H); 5.72 (m, 1H); 5.00 (m, 2H); 4.49 (t, 1H); 3.81 (dd, 1H); 3.72 (dd, 1H); 3.16 (m, 2H); 2.51 (dd, 1H); 2.42 (dd, 1H); 2.22 (m, 1H); 1.24 (s, 3H); 1.10 (s, 3H); 1.05 (d, 3H).

Compound 106

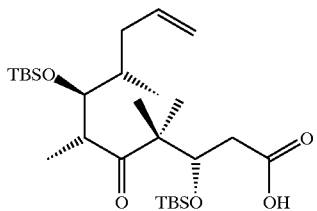

Compound 106 is prepared in analogy to compound 93 from 9.310 g of crude of 105. The crude product obtained after extraction is directly used in the next step. M.p. ° C. ESI-MS: 178 (M+H).

Compound 96

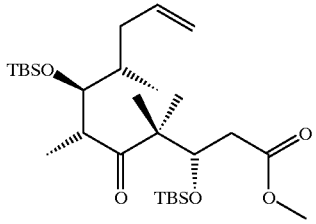

The preparation of compound 96 from 106 is performed in analogy to the preparation of 94 from 93, starting from 8.1 g of crude 106. Purification by FC in hexane/ether 8/2 gives 96 as an oil. ESI-MS: 515 (M+H). $^1$H-NMR (CDCl$_3$, 500 MHz): δ (ppm vs. TMS)=5.72 (m, 1H); 5.00 (m, 2H); 4.41 (dd, 1H); 3.82 (dd, 1H); 3.48 (dd, 1H); 3.38 (m, 2H); 2.5 (dd, 1H); 2.32 (dd, 1H); 1.87 (m, 1H); 1.40 (m, 1H); 1.25 (s, 3H); 1.10 (s, 3H); 1.08 (d, 3H).

Examples 79 and 81 can be obtained from Example 77 via activation of the primary hydroxyl group (e.g. as tosylate, mesylate or triflate) and subsequent displacement with N$_3$- (followed by reduction). Likewise Examples 87 and 89 can be obtained from Example 85.

EXAMPLE 97: SOFT CAPSULES 5000 soft gelatin capsules, each containing as active ingredient 0.05 g of one of the compounds of formula I named in the preceding examples, e.g. the compounds of example 2, 3 or 4, are prepared as follows:

| composition | |
|---|---|
| active ingredient | 250 g |
| Lauroglykol | 2 liters |

Preparation process: The pulverised active ingredient is suspended in Lauroglykol® (propylene glycol laurate, Gattefossé S.A., Saint Priest, France) and ground in a wet pulverizer to a grain size of approximately 1 to 3 µm. Portions each containing 0.419 g of the mixture are then filled into soft gelatin capsules by a capsule filling machine.

EXAMPLE 98: INFUSION SOLUTION

The compound of example 1, 2, 3 or 4 is dissolved at a concentration of 1 mg/ml in polyethylene glycol 300 (PEG 300) and filled into 2 ml vials. For infusion, this solution is diluted with 50 to 100 ml of 0.9% saline according to US Pharmacopoeia.

What is claimed is:

1. A compound of formula I

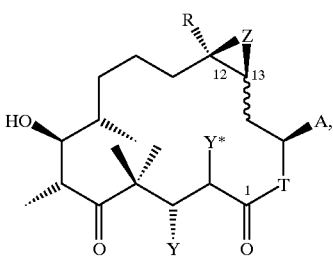

wherein

T is O, NH or N(alkyl), wherein alkyl is alkyl;

A is a radical of formula Ia

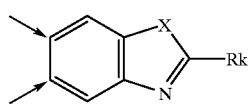

which is bonded to the radical of the molecule according to formula I by one of the two carbon atoms marked with an arrow, and wherein X is S; O; NH; N(alk); wherein alk is alkyl, hydroxy-lower alkyl, unsubstituted or substituted amino-lower alkyl or carbamoyl-lower alkyl; N(ar), wherein ar is aryl; C(Rk*)=N, N=C(Rk*) or C(Rk*)=C(Rk**), wherein Rk* and Rk**, independently of one another, are H, alkyl, unsubstituted or substituted amino-lower alkyl, carbamoyl-lower alkyl, halogen-lower alkyl or hydroxy-lower alkyl; and Rk is H, alkyl, unsubstituted or substituted amino-lower alkyl, carbamoyl-lower alkyl, halogen-lower alkyl or hydroxy-lower alkyl;

either Y is OH and Y* is hydrogen, or —Y and —Y* together form a bond (so that they form a double bond together with the adjoining bond connecting the two —Y and —Y* bearing carbon atoms);

R is hydrogen, lower alkyl or halogen-lower alkyl;

and Z is O, or —Z— is a bond between the two binding carbon atoms;

or salts thereof.

2. A compound of formula I* according to claim 1,

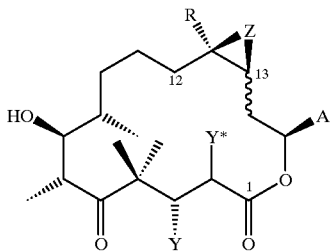

(I*)

wherein

A is a radical of formula Ia

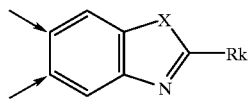

(Ia)

which is bonded to the radical of the molecule according to formula I by one of the two carbon atoms marked with an arrow, and wherein X is S; O; NH; N(alk); wherein alk is alkyl; N(ar), wherein ar is aryl; C(Rk*)=N, N=C(Rk*) or C(Rk*)=C(Rkt*), wherein Rk* and Rk**, independently of one another, are H, alkyl, halogen-lower alkyl or hydroxy-lower alkyl; and Rk is H, alkyl, halogen-lower alkyl or hydroxy-lower alkyl;

either Y is OH and Y* is hydrogen, or —Y and —Y* together form a bond (so that they form a double bond together with the adjoining bond connecting the two —Y and —Y* bearing carbon atoms);

R is hydrogen, lower alkyl or halogen lower alkyl; and Z is O, or —Z— is a bond between the two binding carbon atoms; or a salt thereof.

3. A compound of formula I* according to claim 2, wherein

A is a radical of formula Ia which is bonded to the radical of the molecule of formula I by one of the two carbon atoms marked by an arrow; and wherein X is S; O; NH; N(alk); C(Rk*)=N, N=C(Rk*) or C(Rk*)=C(Rk**), wherein Rk* and Rk**, independently of one another, are H, lower alkyl, halogen-lower alkyl or hydroxy-lower alkyl;

and

Rk is H, lower alkyl, halogen-lower alkyl or hydroxy-lower alkyl;

either Y is OH and Y* is hydrogen, or —Y and —Y* together form a bond;

R is hydrogen, lower alkyl or halogen-lower alkyl;

and Z is O, or —Z— is a bond between the two binding carbon atoms;

or salts thereof.

4. A compound of formula I according to claim 1, wherein T is O or NH;

A is a radical of formula Ia, Which is bonded to the radical of the molecule according to formula I by one of the two carbon atoms marked with an arrow, and wherein X is S; O; NH; N(alk); wherein alk is alkyl, hydroxy-lower alkyl, unsubstituted or substituted amino-lower alkyl or carbamoyl-lower alkyl; C(Rk*)=N, N=C(Rk*) or C(Rk*)=C(Rk**), wherein Rk* and Rk**, independently of one another, are H, alkyl, halogen-lower alkyl or hydroxy-lower alkyl, substituted or unsubstituted amino-lower alkyl or carbamoyl-lower alkyl; and Rk is H, lower alkyl, halogen-lower alkyl or hydroxy-lower alkyl, unsubstituted or substituted amino-lower alkyl or carbamoyl-lower alkyl;

either Y is OH and Y* is hydrogen, or —Y and —Y* together form a bond;

R is hydrogen, lower alkyl or halogen-lower alkyl;

and Z is O, or —Z— is a bond between the two binding carbon atoms; or salts thereof.

5. A compound of formula I according to claim 1, wherein T is O;

A is a radical of formula Ia

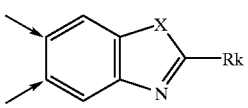

(Ia)

which is bonded to the radical of the molecule according to formula I by one of the two carbon atoms marked with an arrow, and wherein X is S; O; NH; N(alk); wherein alk is alkyl; N(ar), wherein ar is aryl; C(Rk*)=N, N=C(Rk*) or C(Rk*)=C(Rk**), wherein Rk* and Rk**, independently of one another, are H, alkyl, halogen-lower alkyl or hydroxy-lower alkyl, or amino lower alkyl: and Rk is H, alkyl, halogen-lower alkyl or hydroxy-lower alkyl;

either Y is OH and Y* is hydrogen, or —Y and —Y* together form a bond (so that they form a double bond together with the adjoining bond connecting the two —Y and —Y* bearing carbon atoms);

R is hydrogen, lower alkyl or halogen-lower alkyl;

and Z is O, or —Z— is a bond between the two binding carbon atoms;

or salts thereof.

6. A compound of formula I according to claim 1, wherein T is NH or O;

A is a radical of formula Ia, which is bonded to the radical of the molecule according to formula I by one of the two carbon atoms marked with an arrow, and wherein X is S, O, NH, N(CH$_3$), N(CH$_2$CH$_2$OH), N(CH$_2$CH$_2$NH$_2$), N(CH$_2$CH$_2$N(CH$_3$)$_2$), N(CH$_2$C(O)NH$_2$), C(Rk*)=N or CH=C(Rk*), wherein Rk* is H, methyl, hydroxymethyl, (CH$_2$CH$_2$OH), (CH$_2$CH$_2$NH$_2$), (CH$_2$CH$_2$N(CH$_3$)$_2$), (CH$_2$C(O)NH$_2$), or fluormethyl and Rk is hydrogen, methyl, ethyl, hydroxymethyl, hydroxyethyl, aminomethyl, aminoethyl, dimethylaminomethyl, carbamoylmethyl or fluormethyl R is hydrogen, methyl, ethyl or fluoromethyl; and Z is O, or —Z— is a bond between the two binding carbon atoms;

or salts thereof; whereby the bond characterised by a wavy line means that the compound of formula I is present in cis- or trans-form, preferably in cis-form.

7. A compound of formula I according to claim 1, wherein

T is O;

A is a radical of formula Ia, which is bonded to the radical of the molecule according to formula I by one of the two carbon atom is marked with an arrow, and wherein X is S, O, NH, N(CH$_3$), N(HC$_2$CH$_2$OH), C(Rk*)=N or CH=C(Rk*), wherein Rk* is H, methyl or hydroxymethyl;

and

Rk is hydrogen, methyl, e or hydroxymethyl;

R is hydrogen, methyl, ethyl or fluoromethyl; and

Z is O, or —Z— is a bond between the two binding carbon atoms;

or a salt thereof; whereby the bond characterised by a wavy line is present to show that the compound of formula I exists in cis- or trans-form, preferably in cis-form.

8. A compound of formula I according to claim 1, wherein

A means a radical of formula Ia, which is bonded to the radical of the molecule according to formula I by one of the two carbon atoms marked with an arrow, and wherein X is S, N(CH$_3$) or CH=CH;

and

Rk is H, methyl or hydroxymethyl, preferably methyl;

R is hydrogen, lower alkyl or halogen lower alkyl; and

Z is O, or (preferably) —Z— is a bond between the two binding carbon atoms, or a salt thereof.

9. A compound of formula I, wherein ◄A means a radical selected from the radicals of formulae

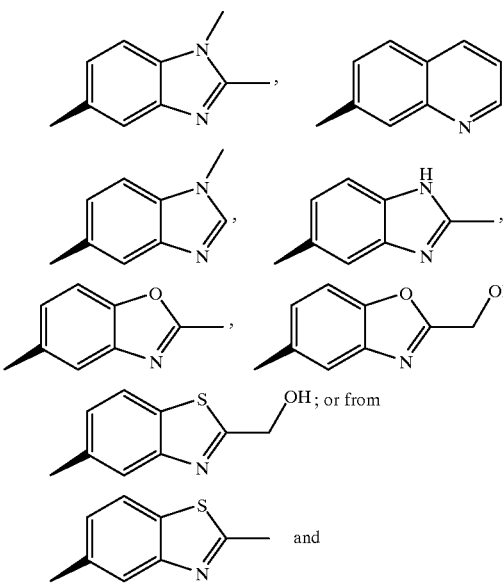

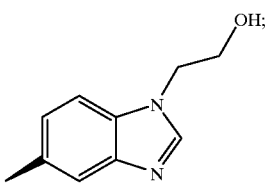

R hydrogen, methyl or ethyl; is O, or —Z— is a bond between the two binding carbon atoms; Y is hydroxy; Y* is hydrogen; and T is O; and the bond indicated by a wavy line is such that the compound of the formula I is present in the cis-form; or a pharmaceutically acceptable salt thereof.

10. A compound according to claim 1, of the formula:

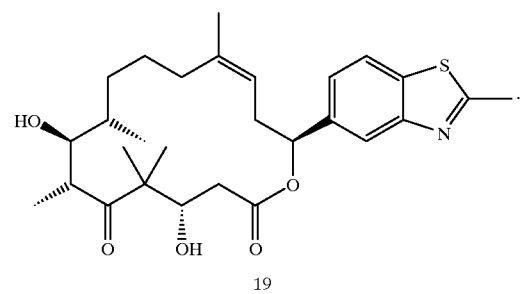

11. A compound according to claim 1, of the formula:

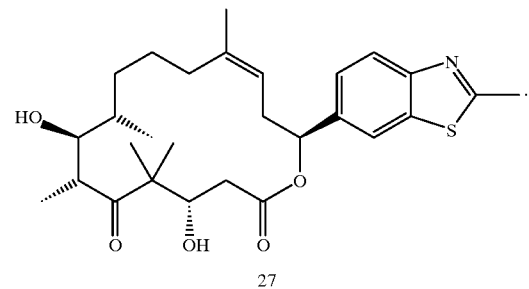

12. A compound according to claim 1, of the formula

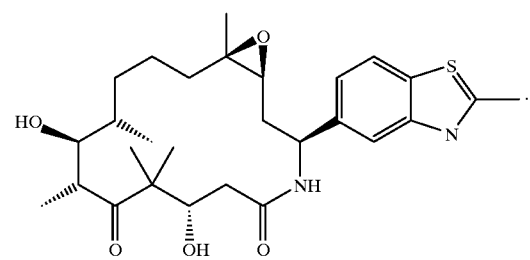

13. A pharmaceutical composition, comprising a compound of formula I, or a salt thereof, provided that salt-forming groups are present, according to claim 1, and one or more pharmaceutically acceptable carriers.

14. A process for the preparation of a compound of formula I according to claim 1, wherein a) an acid of formula II,

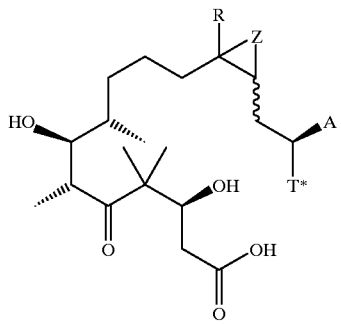

(II)

wherein T* is hydroxy, $NH_2$, NH(alkyl) or $N_3$ and (alkyl), A, Z and R have the meanings given for compounds of formula I, and wherein functional groups that should not participate in the reaction are present if necessary in protected form, is cyclised, if T*=$N_3$, this taking place after reduction of the azide group, and if necessary any protecting groups are removed, and, if desired, an obtainable compound of formula I is converted into a different compound of formula I; an obtainable free compound of formula I is converted into a salt; an obtainable salt of a compound of formula I is converted into another salt or the free compound of formula I; and/or obtainable isomeric mixtures of compounds of formula I are separated into the isomers.

15. A method of treating a warm-blooded animal having a tumor disease, which comprises administering to the animal a therapeutically effective amount of a compound of formula I according to claim 1 or a pharmaceutically acceptable salt thereof.

16. A method of claim 15 wherein the animal is a human.

* * * * *

UNITED STATES PATENT AND TRADEMARK OFFICE
CERTIFICATE OF CORRECTION

PATENT NO. : 6,387,927 B1
DATED : May 14, 2002
INVENTOR(S) : Altmann et al.

It is certified that error appears in the above-identified patent and that said Letters Patent is hereby corrected as shown below:

<u>Column 97,</u>
Line 35, delete "C(Rk*)=C(Rkt*)" and replace with -- C(Rk*)=C(Rkt**) --.

<u>Column 98,</u>
Line 1, delete "Which" and replace with -- which --.

<u>Column 99,</u>
Line 12, delete "atom is" and replace with -- atoms --.
Line 18, after the word "methyl", delete "e".

<u>Column 100,</u>
Line 11, after the word "ethyl"; insert the letter "Z" before the word "is".

Signed and Sealed this

Nineteenth Day of November, 2002

*Attest:*

*Attesting Officer*

JAMES E. ROGAN
*Director of the United States Patent and Trademark Office*